United States Patent [19]

Monkovic et al.

[11] Patent Number: 4,820,715

[45] Date of Patent: Apr. 11, 1989

[54] ANTI-EMETIC QUINUCLIDINYL BENZAMIDES

[75] Inventors: Ivo Monkovic, Fayetteville; David Willner, Dewitt, both of N.Y.

[73] Assignee: Bristol-Myers Company, New York, N.Y.

[21] Appl. No.: 51,880

[22] Filed: May 18, 1987

Related U.S. Application Data

[63] Continuation-in-part of Ser. No. 876,020, Jun. 19, 1986, which is a continuation-in-part of Ser. No. 729,513, May 6, 1985, which is a continuation-in-part of Ser. No. 625,742, Jun. 28, 1984, abandoned.

[51] Int. Cl.⁴ .................. A61K 31/445; C07D 453/02
[52] U.S. Cl. .................................... 514/305; 546/133
[58] Field of Search ........................ 546/133; 514/305

[56] References Cited

U.S. PATENT DOCUMENTS

| | | | |
|---|---|---|---|
| 3,219,528 | 11/1965 | Thominet | 564/162 X |
| 3,966,957 | 6/1976 | Cole, Jr. et al. | 514/426 |
| 4,039,672 | 8/1977 | Bulteau et al. | 514/359 |
| 4,093,734 | 6/1978 | Krueger et al. | 546/133 X |
| 4,127,666 | 11/1978 | Buzas et al. | 514/408 |
| 4,138,492 | 2/1979 | Noverola et al. | 514/316 |
| 4,189,495 | 2/1980 | Kaplan et al. | 546/230 X |
| 4,197,243 | 4/1980 | Murakami et al. | 548/557 |
| 4,207,327 | 6/1980 | Lunsford et al. | 548/356 X |
| 4,593,034 | 6/1986 | Munson et al. | 514/305 |
| 4,605,652 | 8/1986 | Welstead | 514/214 |
| 4,717,563 | 1/1988 | Alphin et al. | 424/10 |

FOREIGN PATENT DOCUMENTS

| | | | |
|---|---|---|---|
| 67615 | 12/1982 | European Pat. Off. | 546/124 |
| 76530 | 4/1983 | European Pat. Off. | 546/224 |
| 158532 | 10/1985 | European Pat. Off. | 546/133 |
| 1500105 | 2/1978 | United Kingdom | 564/162 |
| 1574418 | 9/1980 | United Kingdom | 546/233 |

OTHER PUBLICATIONS

Derwent Abstract of Japan 52 097,968, 8/17/77.

*Primary Examiner*—Richard A. Schwartz
*Attorney, Agent, or Firm*—Richard P. Ryan

[57] ABSTRACT

Novel substituted benzamides of the formula

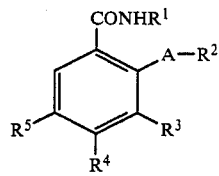

wherein $R^1$, $R^2$, $R^3$, $R^4$, $R^5$ and A are as defined herein are useful in the treatment of emesis, and particularly chemotherapy-induced emesis in cancer patients. Some of the compounds are also useful in disorders relating to impaired gastric motility.

14 Claims, No Drawings

ANTI-EMETIC QUINUCLIDINYL BENZAMIDES

CROSS-REFERENCE TO RELATED APPLICATION

This is a continuation-in-part of application Ser. No. 876,020 filed June 19, 1986, which is a continuation-in-part of application Ser. No. 729,513 filed May 6, 1985, which is a continuation-in-part of application Ser No. 625,742 filed June 28, 1984, now abandoned.

SUMMARY OF THE INVENTION

This invention relates to novel substituted benzamides of the formula

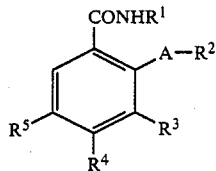

wherein $R^1$, $R^2$, $R^3$, $R^4$, $R^5$ and A are as defined below, which are useful in the treatment of emesis, particularly chemotherapy-induced emesis, such as cisplatin treatment of cancer patients, and/or in treatment of disorders related to impaired gastric motility, such as retarded gastric emptying, dyspepsia, flatulence, esophageal reflux and the like.

BACKGROUND AND PRIOR ART

Emesis is a common and serious problem in patients receiving cancer chemotherapeutic agents. In a significant number of patients, nausea and vomiting is so servere that they discontinue their course of chemotherapeutic treatment prior to its completion. Although no known antiemetic agent is totally effective in alleviating the emesis associated with chemotherapy, there are a large number of compounds (many based on the substituted benzamide structure) which have good antiemetic activity.

Although the complete mechanism of action of antiemetic agents is not known, the effective antiemetic agents are generally dopaminergic antagonists. Indeed, screening for potential antiemetic agents typically is conducted via tests designed to determine dopaminergic blockage, e.g. spiperone binding tests in vitro and apomorphine emesis tests in dogs. As a result of their dopaminergic antagonism and/or central nervous system depression, known antiemetic agents have undesirable side effects such as sedation, dystonic reactions, diarrhea and akathisia.

We have surprisingly found a group of substituted benzamide antiemetic agents with a high specificity of action, which are not dopaminergic antagonists and which are free of the undesirable side effects of the presently known antiemetic agents.

An excellent, modern review article on the variously substituted benzamides and their pharmacological activities is found in "Chemical Regulation of Biological Mechanisms", A. M. Creighton and S. Turner, editors, Royal Society of London (1982), in the chapter entitled "Substituted Benzamides as Dopamine Antagonists", by M. S. Hadley (Pages 140-153). It states that this class of compounds is defined by the formulae

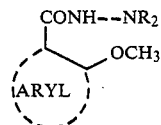

and

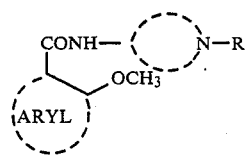

in which the aryl ring is most commonly the phenyl ring and where "a methoxy group ortho to the benzamide moiety is almost invariably present." It points out that the diverse actions of the substituted benzamides can be considered as being a consequence of the compounds being dopamine antagonists.

Representative prior art patents disclosing N-substituted benzamides, having various substituents on the phenyl ring, include the following.

U.S. Pat. No. 3,219,528, issued Nov. 23, 1965 to M. L. Thominet, discloses substituted benzamides of the formula

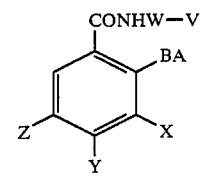

wherein V is

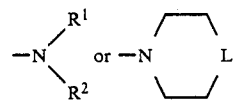

in which $R^1$ and $R^2$ are alkyl, L is oxygen, methylene or NR in which R is hydrogen, alkyl or alkylsulfamoyl; W is alkylene; A is alkyl; B is sulfur or oxygen; and X, Y and Z are hydrogen, halogen, alkoxy, nitro, amino, alkylamino, dialkylamino, (lower)acyl, (lower)acylamino, cyano, alkylmercapto, sulfamoyl, alkylsulfamoyl, dialkylsulfamoyl or halomethyl. The compounds are apomorphine antagonists and are stated to be antiematic agents. U.S. Pat. Nos. 3,177,252, issued Apr. 6, 1965, and 3,312,739, issued Apr. 4, 1967, are related and have similar disclosures.

U.K. Pat. No. 1,500,105, published Feb. 8, 1978, discloses substituted benzamides of the formula

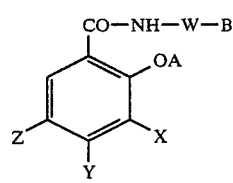

wherein A is hydrogen, $C_{1-5}$ alkyl or $C_{2-5}$ alkenyl; X is hydrogen, $C_{1-5}$ alkoxy, $C_{2-5}$ alkyl, $C_{2-5}$ alkenyloxy or $C_{2-5}$ alkenyl; Y is hydrogen, halogen, nitro, $C_{1-5}$ alkyl, $C_{1-5}$ alkoxy, amino or substituted amino; Z is hydrogen, halogen, $C_{1-5}$ alkoxy, $C_{1-5}$ alkylsulfonyl or a group of the formula $—SO_2NR^1R^2$ in which $R^1$ and $R^2$ are the same or different and are hydrogen or a $C_{1-5}$ alkyl group, or $—NR^1R^2$ is a heterocyclic ring optionally containing another heteroatom; W is a $C_{1-5}$ straight or branched chain alkylene group; B is $—NR^3R^4$ in which $R^3$ is $C_{1-5}$ alkyl and $R^4$ is $C_{1-5}$ hydroxyalkyl, or B is a nitrogen-attached heterocyclic ring optionally containing a second nitrogen atom and optionally having a substituent, or B is a racemic, dextrorotatory or levorotatory heterocyclic ring of the formula

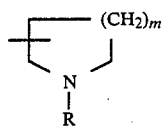

in which R is $C_{1-5}$ alkyl containing a reactive function such as hydroxy, mercapto, oxo, thioxo, oxa or thia; and m is 1, 2 or 3; and acid addition salts, oxides and quaternary ammonium salts thereof. The compounds are stated to be apomorphine antagonists and to have valuable therapeutic properties, particularly as antiemetics.

U.S. Pat. No. 4,207,327, issued June 10, 1980 to C. D. Lunsford et al., discloses compounds of the formula

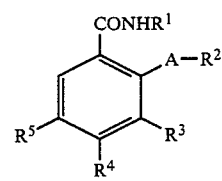

wherein R is alkyl, cycloalkyl or phenylalkyl; $R^1$ is alkyl, cycloalkyl or phenylalkyl; $R^2$ is hydrogen, alkyl or phenyl; and $R^3$ is hydroxy, cyano, nitro, amino, fluoro, chloro, bromo, trifluoromethyl, alkyl, alkoxy, sulfamoyl or acetamido, and each $R^3$ may be the same or different. The compounds are stated to have antiemetic and gastric emptying properties.

U.S. Pat. No. 3,966,957, issued June 29, 1976 to Cale, Jr., et al., discloses substituted benzamides of the formula

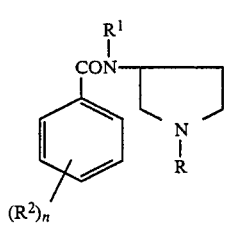

wherein R is cycloalkyl, phenyl or phenylalkyl; $R^1$ is hydrogen, $C_{1-8}$ alkyl or phenyl; $R^2$ is halogen, alkyl, alkoxy, amino, nitro, alkylamino, dialkylamino, mercaptomethyl, acetamido, sulfamoyl, cyano, hydroxy, benzyloxy or trifluoromethyl; and n is 0–3; and substituted thiobenzamides of the formula

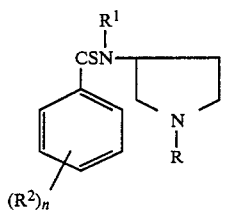

wherein R is cycloalkyl; $R^1$ is hydrogen; or $C_{1-8}$ alkyl; $R^2$ is nitro, amino, halogen, sulfamoyl or alkoxy; and n is 0–3; and pharmaceutically acceptable acid addition salts thereof. U.S. Pat. No. 3,963,745 is related and has a substantially identical disclosure. The compounds are stated to be apomorphine antagonists and to be useful as antiemetics. Certain of the compounds were stated to reduce catalepsy in rats.

COMPLETE DISCLOSURE

This invention relates to compounds of the formula

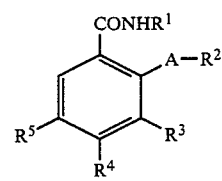
                                                                I wherein:

$R^3$ is hydrogen or, when $R^4$ and $R^5$ are each hydrogen, $R^3$ may be (lower)alkoxy;

$R^4$ is hydrogen, amino or (lower)alkoxy;

$R^5$ is hydrogen, chloro, bromo, fluoro, trifluoromethyl, (lower)alkylthio, (lower)alkanesulfinyl, (lower)alkanesulfonyl, sulfamyl or

or $R^4$ and $R^5$, taken together, may be $—HN—N\!=\!\!N—$;

$R^6$ is (lower)alkyl, (lower)alkenyl or (lower)alkynyl;

$R^1$ is

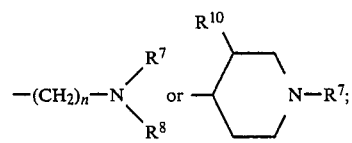

n is an integer of from 1 to 4, inclusive;

$R^7$ and $R^8$ are the same or different and are (lower)alkyl, (lower)alkenyl, (lower)alkynyl,

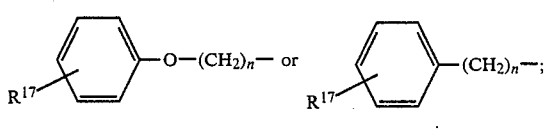

$R^{10}$ is hydrogen or (lower)alkoxy;

$R^{17}$ is hydrogen, halogen, hydroxy, (lower)alkyl or (lower)alkoxy;

A is oxygen or

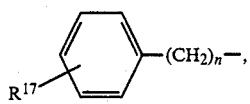

R² is

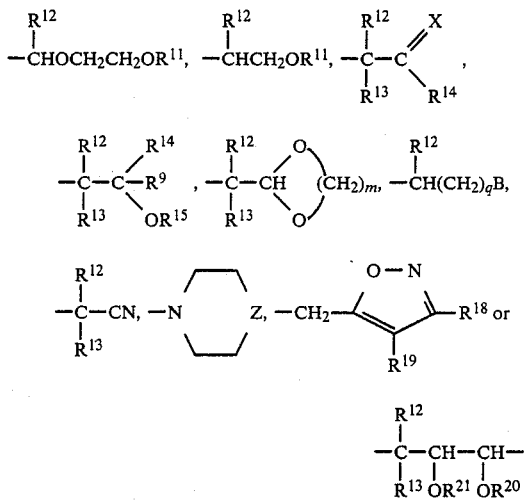

X is oxygen, sulfur or =NR¹⁶;
Z is —(CH₂)ₚ—, O, N or

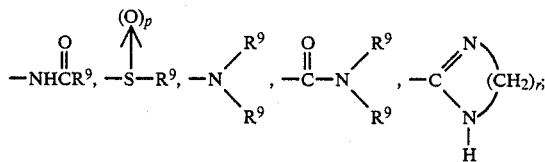

B is

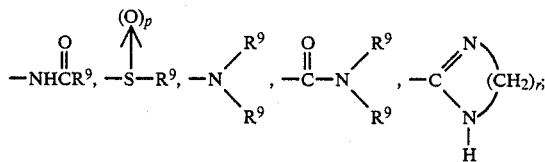

pyridyl or oxazolidinyl;
m is 2 or 3;
p is 0, 1 or 2;
q is an integer of from 0 to 4, inclusive;
r is 2 or 3;
R⁹ is hydrogen or (lower)alkyl;
R¹¹, R¹², R¹³, R¹⁵ and R¹⁶ are the same or different, and are hydrogen, (lower)alkyl, (lower)alkenyl, (lower)alkynyl, (lower)alkoxy(lower)alkyl, cycloalkyl containing from 5 to 7 carbon atoms, inclusive, or

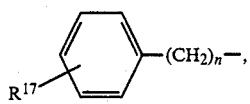

provided that, when R¹¹, R¹⁵ or R¹⁶ is (lower)alkenyl or (lower)alkynyl, the unsaturated carbon atom may not be directly attached to an oxygen or nitrogen atom;
R¹⁴ is hydrogen, halogen, (lower)alkyl, (lower)alkenyl, (lower)alkynyl,cycloalkyl containing from 5 to 7 carbon atoms, inclusive, hydroxy, (lower)alkoxy, (lower)alkenyloxy, (lower)alkoxycarbonyl(lower)alkenyl, hydrazino, acetylhydrazino, thienyl, phenyl,

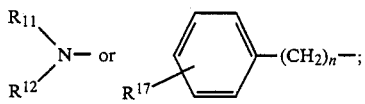

R¹⁸ and R¹⁹ are the same or different and are hydrogen or (lower)alkyl;
R²⁰ and R²¹ are each hydrogen or, taken together, represent

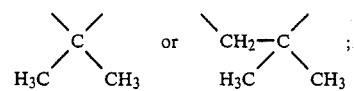

or R¹² and R¹³, taken together with the carbon atom to which they are attached, may form a saturated ring of from 5 to 7 atoms, inclusive, optionally containing at least one heteroatom selected from oxygen, sulfur and nitrogen;
or R¹² and R¹⁴, taken together with the carbon atoms to which they are attached, may form a saturated or unsaturated ring of from 5 to 7 atoms, inclusive, optionally containing at least one heteroatom selected from oxygen, sulfur and nitrogen;
or R¹⁴ and R¹⁵, taken together with the carbon and oxygen atoms to which they are attached, may form a 3 to 7 membered saturated oxygen-containing ring;
or nontoxic pharmaceutically acceptable salts, hydrates, solvates or quaternary ammonium salts thereof.
A more preferred group of the compounds of Formula I are those of the formula

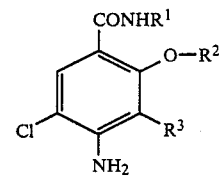

I wherein
R³ is hydrogen or, when R⁴ and R⁵ are each hydrogen, R³ may be (lower)alkoxy;
R¹ is

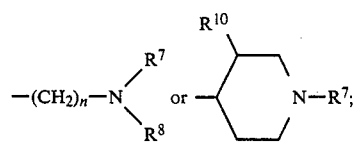

n is an integer of from 1 to 4, inclusive;
R⁷ and R⁸ are the same or different and are (lower)alkyl, (lower)alkenyl or (lower)alkynyl;
R¹⁰ is hydrogen or (lower)alkoxy;
R² is

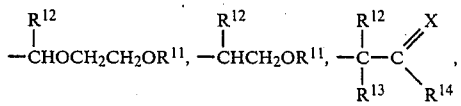

-continued

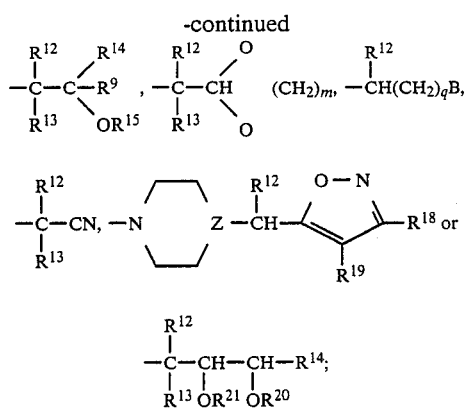

X is oxygen, sulfur or =NOR[16];
Z is —(CH$_2$)$_p$—, O, N or

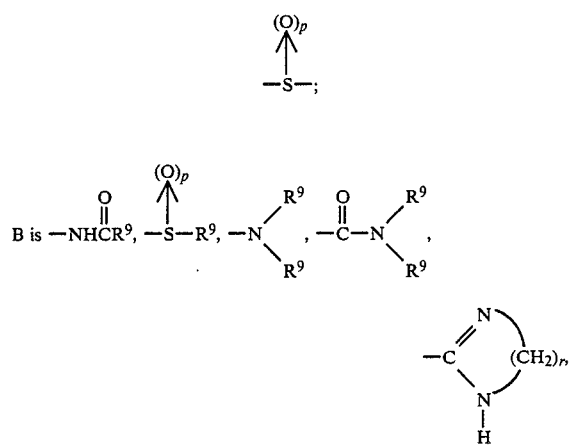

pyridyl or oxazolidinyl;
m is 2 or 3;
p is 0, 1 or 2;
q is an integer of from 0 to 4;
r is 2 or 3;
R$^9$ is hydrogen or (lower)alkyl;
R$^{11}$, R$^{12}$, R$^{13}$, R$^{15}$ and R$^{16}$ are the same or different, and are hydrogen, (lower)alkyl, (lower)alkenyl, (lower)alkynyl, (lower)alkoxy(lower)alkyl or cycloalkyl containing from 5 to 7 carbon atoms, inclusive, provided that, when R$^{11}$, R$^{15}$ or R$^{16}$ is (lower)alkenyl or (lower)alkynyl, the unsaturated carbon atom may not be directly attached to an oxygen or nitrogen atom;
R$^{14}$ is hydrogen, halogen, (lower)alkyl, (lower)alkenyl, (lower)alkynyl, cycloalkyl containing from 5 to 7 carbon atoms, inclusive, (lower)alkoxy, hydroxy, (lower)alkenyloxy, hydrazino, (lower)alkoxycarbonyl(lower)alkenyl, acetylhydrazino, thienyl, phenyl, phenyl(lower)alkyl or

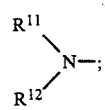

R$^{18}$ and R$^{19}$ are the same or different and are hydrogen or (lower)alkyl;
R$^{20}$ and R$^{21}$ are each hydrogen or, taken together, represent

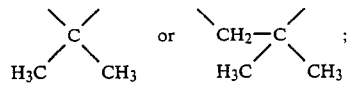

or R$^{12}$ and R$^{14}$, taken together with the carbon atoms to which they are attached, may form a saturated or unsaturated ring of from 5 to 7 atoms, inclusive, optionally containing at least one heteroatom selected from oxygen, sulfur and nitrogen;
or R$^{14}$ and R$^{15}$, taken together with the carbon and oxygen atoms to which they are attached, may form a 3 to 7 membered saturated oxygen-containing ring;
or nontoxic pharmaceutically acceptable salts, hydrates, solvates or quaternary ammonium salts thereof.

A still more preferred group of the compounds of Formula I are those of the formula

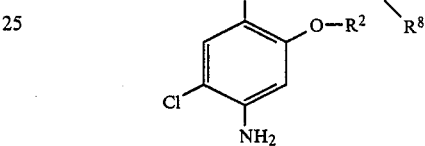

wherein
R$^7$ and R$^8$ are the same or different and are ethyl or methyl;
R$^2$ is

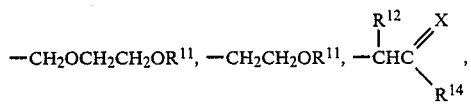

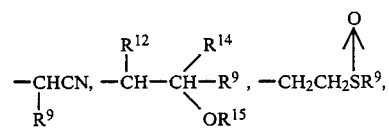

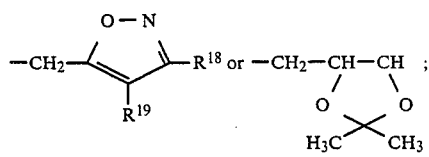

X is oxygen or =NOR$^{16}$;
R$^9$ is hydrogen or (lower)alkyl;
R$^{11}$, R$^{12}$, R$^{15}$ and R$^{16}$ are the same or different, and are hydrogen, (lower)alkyl, (lower)alkenyl, (lower)alkynyl (lower)alkoxy(lower)alkyl or cycloalkyl containing from 5 to 7 carbon atoms, inclusive, provided that, when R$^{11}$, R$^{15}$ or R$^{16}$ is (lower)alkenyl or (lower)alkynyl, the unsaturated carbon atom may not be directly attached to an oxygen or nitrogen atom;
R$^{14}$ is hydrogen, halogen, (lower)alkyl, (lower)alkoxy, hydroxy, hydrazino, (lower)alkoxycarbonyl(lower)alkenyl, acetylhydrazino, thienyl, phenyl, phenyl(lower)alkyl or

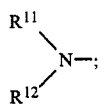

$R^{18}$ and $R^{19}$ are the same or different and are hydrogen or methyl;

or $R^{12}$ and $R^{14}$, taken together with the carbon atoms to which they are attached, may form a saturated or unsaturated ring of from 5 to 7 atoms, inclusive, optionally containing at least one heteroatom selected from oxygen, sulfur and nitrogen;

or $R^{14}$ and $R^{15}$, taken together with the carbon and oxygen atoms to which they are attached, may form a 3 to 6 members saturated oxygen-containing ring;

or nontoxic pharmaceutically acceptable salts, hydrates, solvates or quaternary ammonium salts thereof.

Particularly preferred compounds of Formula I are
4-amino-5-chloro-N-[2-(diethylamino)ethyl]-2-(2-methoxyethoxy)benzamide,
4-amino-5-chloro-N-[2-(diethylamino)ethyl]-2-(2-hydroxyethoxy)benzamide,
4-amino-5-chloro-N-[2-(diethylamino)ethyl]-2-(2,2-dimethoxyethoxy)benzamide,
4-amino-5-chloro-N-[2-(diethylamino)ethyl]-2-[(2-methoxyethoxy)methyloxy]benzamide,
4-amino-5-chloro-N-[2-(diethylamino)ethyl]-2-(2-propanon-1-yl)oxybenzamide,
4-amino-2-benzoylmethyloxy-5-chloro-N-[2-(diethylamino)ethyl]benzamide,
4-amino-2-(butan-2-on-3-yl)oxy-5-chloro-N-[2-(diethylamino)ethyl]benzamide,
4-amino-5-chloro-2-(cyclohexanon-2-yl)oxy-N-[2-(diethylamino)ethyl]benzamide,
4-amino-5-chloro-N-[2-(diethylamino)ethyl]-2-(5-hexan-2-on-3-yl)oxybenzamide,
4-amino-5-chloro-N-[2-(diethylamino)ethyl]-2-[(2-hydroxyimino)propan-1-yl]oxybenzamide,
4-amino-5-chloro-N-[2-(diethylamino)ethyl]-2-[(2-methoxyimino)propan-1-yl]oxybenzamide,
4-amino-5-chloro-N-[2-(diethylamino)ethyl]-2-(2-hydroxypropan-1-yl)oxybenzamide,
4-amino-5-chloro-2-cyanomethyloxy-N-[2-(diethylamino)ethyl]benzamide,
4-amino-2-(carboxamidomethyloxy)-5-chloro-N-[2-(diethylamino)ethyl]benzamide acetate,
4-amino-2-(2-butyn-1-yl)-oxy-5-chloro-N-[2-(diethylamino)ethyl]benzamide,
4-amino-5-chloro-N-[2-(diethylamino)ethyl]-2-[2-(methylsulfinyl)ethoxy]benzamide,
4-amino-5-chloro-N-[2-(diethylamino)ethyl]-2-(pentan-2-on-3-yl)oxybenzamide,
4-amino-2-(2-butanon-1-yl)oxy-5-chloro-N-[2-(diethylamino)ethyl]benzamide,
4-amino-5-chloro-N-[2-(diethylamino)ethyl]-2-(pentan-2-on-1-yl)oxybenzamide,
4-amino-5-chloro-2-(pentan-3-on-2-yl)oxy-N-(2-diethylaminoethyl)benzamide,
4-amino-5-chloro-N-[2-(diethylamino)ethyl]-2-(2-hydrazino-2-oxoethoxy)benzamide,
threo-4-amino-5-chloro-N-[2-(dimethylamino)ethyl]-2-(2-hydroxybut-3-yl)oxybenzamide,
erythro-4-amino-5-chloro-N-[2-(diethylamino)ethyl]-2-(2-hydroxybut-3-yl)oxybenzamide,
4-amino-5-chloro-N-[2-(diethylamino)ethyl]-2-[2-(methylamino)-2-oxoethoxy]benzamide,
4-amino-5-chloro-N-[2-(diethylamino)ethyl]-2-(ethyl-3-methoxycroton-4-yl)oxybenzamide,
4-amino-5-chloro-N-[2-(diethylamino)ethyl]-2-(1,3-dioxolan-2-yl)oxybenzamide,
4-amino-5-chloro-N-[2-(diethylamino)ethyl]-2-(oxazolidin)-2-one-5-ylmethyl)oxybenzamide,
4-amino-5-chloro-N-[2-(diethylamino)ethyl]-2-(2-pyridinomethyl)oxybenzamide,
4-amino-5-chloro-N-[2-(diethylamino)ethyl]-2-tetrahydrofuryloxybenzamide and
4-amino-5-chloro-N-[2-(diethylamino)ethyl]-2-(2-methoxyethoxyethyl)oxybenzamide,
and nontoxic pharmaceutically acceptable salts, hydrates, solvates and quaternary ammonium salts thereof.

Also included within the scope of this invention are all possible optical and geometric isomers of the compounds of Formula I, and tautomeric forms thereof, where applicable. In another aspect, this invention relates to processes for the preparation of the compounds of Formula I and to antiemetic and/or gastrokinetic compositions containing at least one compound of Formula I as an active ingredient.

The compounds of Formula I may be prepared via several procedures. In the preferred process, shown in Reaction Scheme 1, below, a compound of Formula II is reacted with a compound of Formula $R^2$-L (where L is a conventional leaving group) in the presence of a base as an acid scavenger, to produce the compound of Formula I.

Reaction Scheme 1

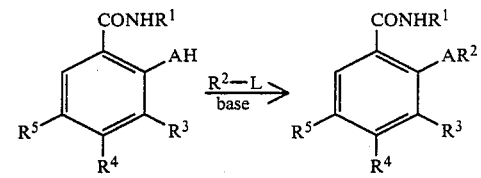

II           I

Suitable leaving groups L are well-known to those skilled in the art and include, for example, chloro, bromo, iodo, methanesulfonyl, toluenesulfonyl and the like. The base may be a mild one such as $K_2CO_3$, $Na_2CO_3$, $MgSO_4$ or a quaternary ammonium hydroxide such as tetrabutylammonium hydroxide or benzyltriethylammonium hydroxidel, or a mixture thereof. The reaction is conducted in an inert organic solvent such as acetone, acetonitrile, methylene chloride, dimethylformamide, dimethylacetamide, methanol, ethanol, isopropanol, diglyme, or the like. It is also possible to utilize sodium hydride or potassium hydride as the base, in an anhydrous, non-protonic organic solvent, or to use a strong base such as NaOH or KOH as a highly concentrated solution in a phase transfer solvent system such as $CH_2Cl_2/H_2O$, with the addition of a quaternary ammonium halide, sulfate or hydroxide as a phase transfer catalyst, e.g. tetrabutylammonium chloride, cetyltrimethylammonium bromide, benzyltriethylammonium chloride, or the like.

It will be apparent to those skilled in the art that Reaction Scheme 1 also may be varied to the extent that substituent groups $R^3$, $R^4$ and/or $R^5$ may be inserted into the compound of Formula I (or converted from a precursor group) as the final step, rather than being present in the compound of Formula II. Thus, for example, Compound I, where $R^5$ is hydrogen, may be chlorinated to produce Compound I in which $R^5$ is chloro. Similarly, $R^4$ of Compound I may be, for example, $-NO_2$, $-NHCOR$ or $-N=CHN(R)_2$ where R may be (lower)alkyl. The $-NO_2$ group may then be reduced to an amino group, or the $-NHCOR$ or $-N=CHN(R)_2$ groups may be hydrolyzed to an amino group.

We prefer to use an organic solvent-soluble tetrasubstituted ammonium salt as illustrated below for one of the preferred compounds of Formula I.

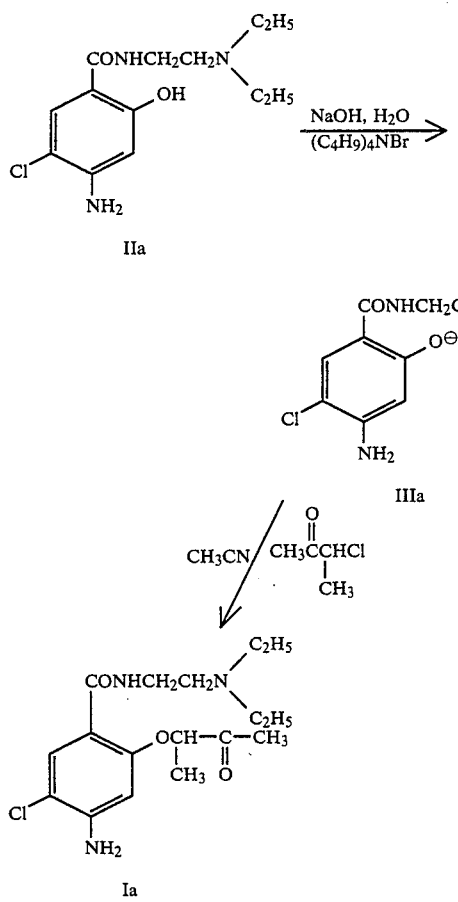

In the first step, Compound IIa is dissolved in aqueous sodium hydroxide and treated with one equivalent of tetrabutylammonium bromide. The quaternary ammonium salt IIIa precipitates from solution and is collected by filtration. It is then reacted with the desired alkylating agent in an inert organic solvent such as dimethylformamide, dimethylacetamide, acetonitrile, tetrahydrofuran, $CHCl_3$, dimethylsulfoxide or diglyme, to produce the desired product Ia.

The intermediate of Formula IIa may be prepared, for example, from demethylation of commercially available metoclopramide, having the formula

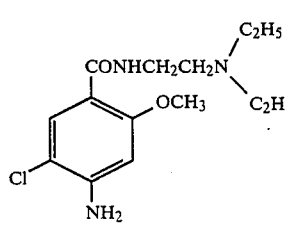 metoclopramide

Metoclopramide may be demethylated by methods well-known to those skilled in the art. Suitable procedures involve reaction with a thioalkoxide or thioaryloxide such as $NaSC_2H_5$, $KSC_2H_5$, $LiSC_2H_5$ or

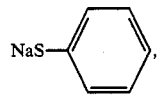

in an inert organic solvent such as dimethylformamide or dimethylsulfoxide, or by reaction with NaOH or KOH in a solvent such as ethylene glycol, propylene glycol or diglyme, or by reaction with 48% aqueous hydrobromic acid. We prefer to demethylate using $NaSC_2H_5$ in dimethylformamide.

It will be appreciated that certain 2-substituents may be difficult to insert directly into Compound IIa without elaborate protecting and deprotecting schemes. On the other hand, the initially inserted 2-substituent may be subsequently modified. Using Compound Ib, another preferred compound of this invention, as an example, various conversions are shown below

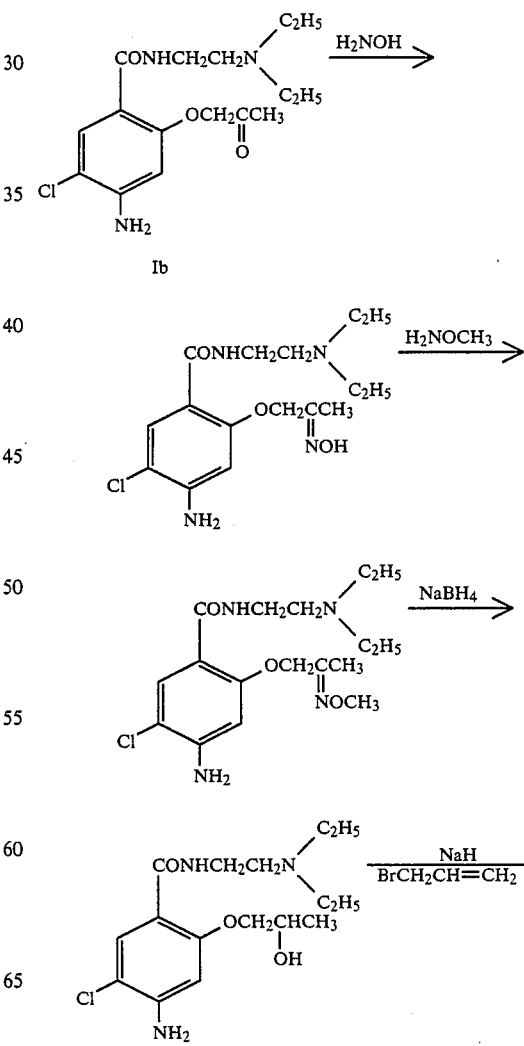

-continued

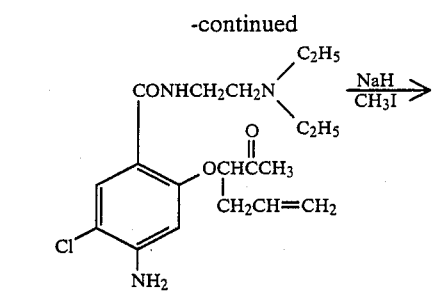

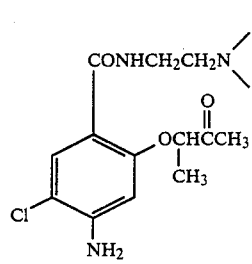

NaH
BrCH₂CH=CH₂

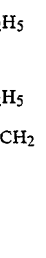

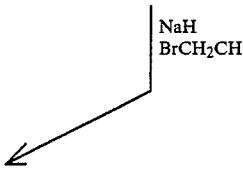

In an alternative procedure for the preparation of the compounds of Formula I, a compound of Formula IV having the desired 2-substituent is reacted so as to introduce the desired substituted carboxamido group in the 1-position. As shown in Reaction Schemes 2a through 2h, there are several variants of this reaction procedure. A preferred 1-substituent is shown for illustrative purposes.

Reaction Scheme 2

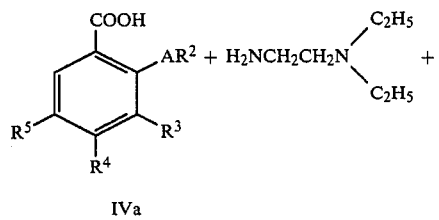

triphenyl phosphine + di(2-pyridyl)disulfide ⟶

-continued

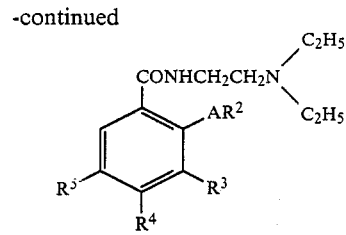

This reaction is described in greater detail, with the use of various disulfides and phosphorus compounds, in U.K. patent specifications No. 1,449,524, published Sept. 15, 1976.

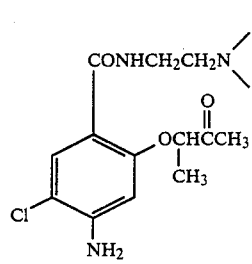

IVb

The starting material and the amine are heated to about 100° C., at which point the P₂O₅ is added and the temperature is raised to about 150° C. for a short period. This procedure is described in U.K. patent specification No. 1,441,352, published June 30, 1976.

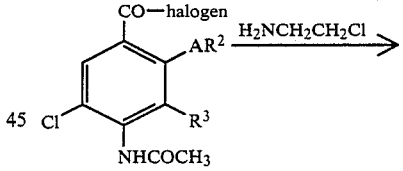

IVc

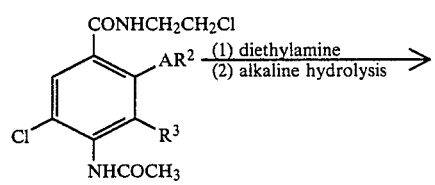

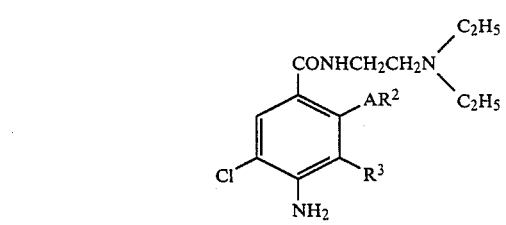

In this reaction, an amino substituent in the 4-position should be protected by acylation to a suitable amido group such as acetamido. Following the introduction of the 1-substituent, the 4-acetamido group is converted to an amino group by alkaline hydrolysis. This procedure, with variations, is described in U.K. patent specification No. 1,395,132, published May 21, 1975.

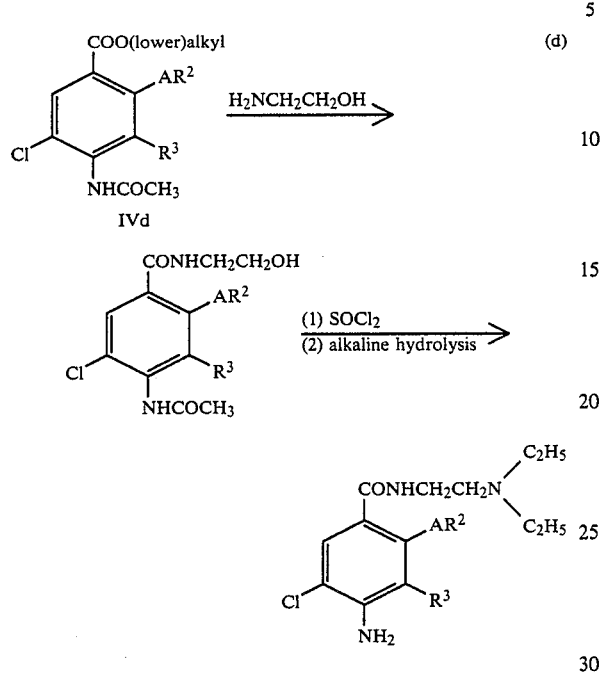

(d)

This reaction, a variation of that shown in (d) above, is described in U.K. patent specification No. 1,395,131, published May 21, 1975.

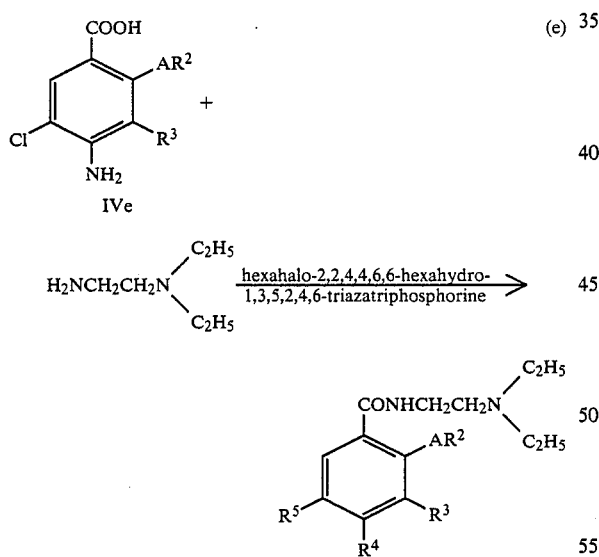

(e)

This procedure, and variations thereof, is described in U.K. patent specification No. 1,409,686, published Oct. 15, 1975.

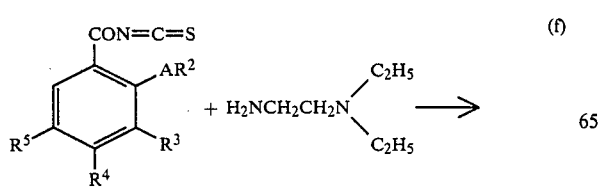

(f)

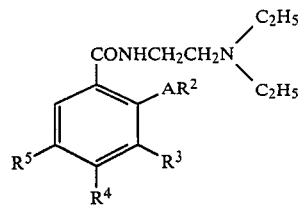

This procedure is described in published Japanese patent application (Kokai) No. 51-026840, published Mar. 5, 1976.

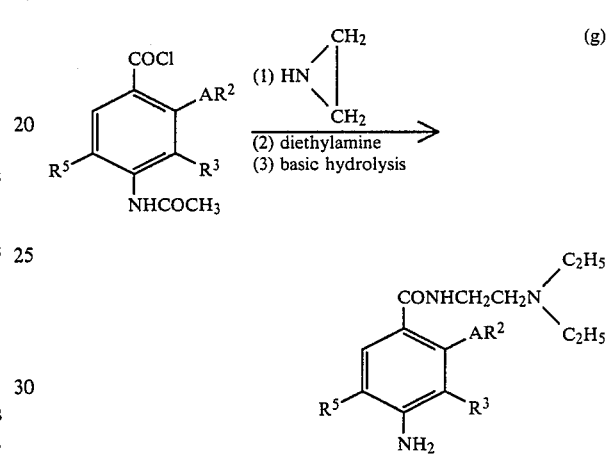

(g)

In this procedure, the 4-amino substituent is protected by acylation, e.g. formation of an acetamido group, which is subsequently hydrolyzed to the free amino group in the final product. This procedure, and variations thereof, is described in published Japanese patent application (Kokai) No. 47-18652, published Sept. 16, 1972.

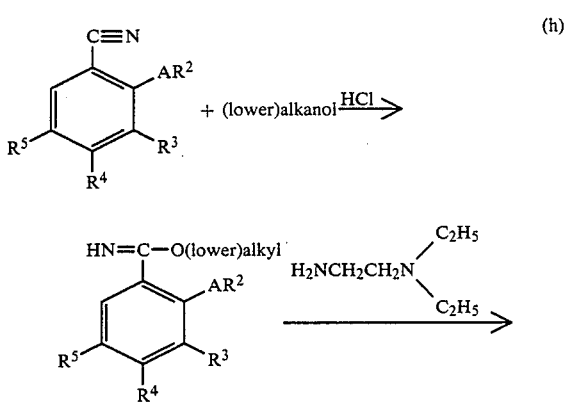

(h)

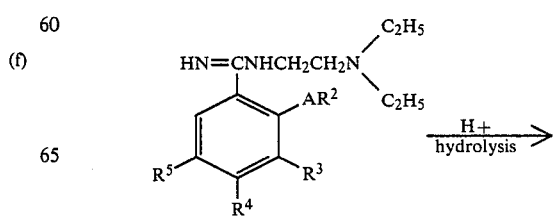

-continued

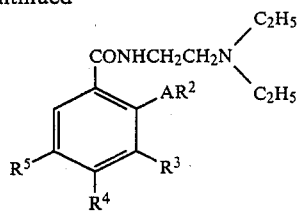

This procedure, and variations thereof, is described in Belgian Pat. No. 692,670, published July 17, 1967.

The physiology and neuropharmacology of emesis, and particularly chemotherapy-induced emesis, is not completely understood. The control mechanism for emesis consists of two distinct units in the medulla, the emetic center and the chemoreceptor trigger zone (CTZ). The emetic center, which is the final common pathway for all emetic stimuli, is located in the lateral reticular formation of the fourth ventricle. The CTZ is also located in the floor of the fourth ventricle, in the area postreme, and appears to be activated by chemical stimuli in the blood or cerebrospinal fluid. When stimulated, receptors, such as dopamine receptors, in the CTZ generate impulses which are transmitted top the emetic center, and emesis results. Reflexinduced vomiting may also be caused by irritation (and resulting stimuli) from the gastrointestinal tract or stimulation of receptors in the central nervous system. The cortex of the brain is believed to be another source of emesis. Thus, the familiar problem of anticipatory vomiting in patients receiving chemotherapy clearly is not associated with exogenous chemical stimulation. It is believed that anticipatory vomiting is mediated initially by the cortex which may then stimulate the medullary emetic center.

There are a number of commercially available antiemetic drugs at the present time, such as metoclopramide, bromopride, alizapride, clebopride, domperidone and nabilone. Metoclopramide is a leading compound and is utilized extensively in combination with cisplatin, which is an effective but highly emetogenic chemotherapeutic agent.

Presently available substituted benzamide antiemetic agents are generally dopaminergic antagonists and, indeed, are believed to exert their antiemetic activity by blocking dopamine receptors in the CTZ. Screening tests for potential antiemetic agents have historically involved tests which determine dopaminergic antagonist activity, e.g. spiperone binding tests in vitro, and the reduction of apomorphine-induced vomiting in the dog or cat.

The principal adverse effects of known substituted benzamide antiemetic agents are due to their dopamine blocking activity, and include akathisia, acute dystonia, Parkinsonian features and tardive dyskinesia, often along with nervous system depression.

The compounds of Formula I of the present invention are effective antiemetic agents but are not dopaminergic antagonists, as shown by both in vitro tests (spiperone binding) and in vivo tests (apomorphine emesis in the dog). Thus, the compounds of Formula I have good antiemetic activity (particularly against chemotherapy-induced emesis) with a high specificity of action, but with none of the side effect liabilities (such as described above) that are associated with the dopaminergic antagonist class of substituted benzamide antiemetic agents.

Many of the commercially available substituted benzamide antiemetic agents (such as metoclopramide) also have gastrokinetic activity and are useful in the treatment of disorders related to impaired gastrointestinal motility, such as retarded gastric emptying, dyspepsia, flatulence, esophageal reflux and the like. Some of the compounds of Formula I have been shown to have activity similar to metoclopramide in the field-stimulated guinea pig ileum test (Table 2), which is one standard screening test for gastrokinetic activity. Again, because they are not dopaminergic antagonists, the compounds of Formula I do not have the above-mentioned side-effect liabilities of the commercially available substituted benzamides such as metoclopramide or clebopride.

BIOLOGICAL TEST PROCEDURES (A) $3_H$-Spiperone Displacement

This test serves to detect compounds capable of displacing the radioactive spiperone ligand in vitro using striatal rat brain homogenates. It is used to identify compounds exhibiting an affinity to dopaminergic ($D_2$) receptors.

Rats (150±10 g; Charles River) were decapitated, the corpus striatum dissected out and frozen on dry ice. The tissues were pooled and stored at $-80°$ C. until used. Homogenates (Brinkmann Polytron) of the corpus striatum in cold HEPES.KOH buffer (final pH=7.4) were centrifuged at 39,000×G. The supernatant was discarded and the pellets were re-suspended in HEPES.KOH buffer and re-centrifuged as above. The supernatant was again discarded and the pellets suspended in a buffer consisting of 50 mM HEPES.KOH containing 0.1% (w/v) ascorbic acid, 10 $\mu$M pargyline, 120 mM NaCl, 5 mM KCl, 2 mM $CaCl_2$ and 1 mM $MgCl_2$ at 20° C.; (final pH=7.4), at a concentration of 1 gm of wet tissue pellet per 100 ml of buffer mixture.

Tests to determine the Inhibitory Concentration$_{50}$ ($IC_{50}$) of the compounds of Formula I and reference compounds versus $^3$H-spiperone were conducted as follows. Tubes containing either 100 $\mu$L of buffer mixture (for total binding), 100 $\mu$L of buffer mixture plus 100 $\mu$L of $10^{-4}$M D(+)-butaclamol (for blanks, i.e. non-specific binding), or 100 $\mu$L of buffer mixture containing $10^{-7}$, $10^{-6}$ or $10^{-5}$M test compound were prepared. To each were added 100 $\mu$L of a solution of $^3$H-spiperone (New England Nuclear) in buffer mixture (2000 c.p.m. in the incubation mixture) and 800 $\mu$L of the striatal tissue suspension. The tubes were then diluted to 1 mL with buffer mixture, giving a final concentration of $10^{-8}$, $10^{-7}$ or $10^{-6}$M test compound and approximately 100 pM $^3$H-spiperone. The samples were incubated at 37° C. for 15 minutes, filtered in vacuo on glass fiber filters and counted by liquid scintillation spectrometry. For each of the test compounds, the $IC_{50}$ was not reached at the highest concentration ($10^{-6}$ $\mu$M=1000 nM) of test compound, so the results in Table 2 were reported as >1000 nM. For the reference compounds, where the $IC_{50}$ was reached (or exceeded) with the original concentrations, the tests were repeated utilizing ¼, ½, 1, 2 and 4 times the concentration estimated (from the original concentrations) to be closest to the $IC_{50}$, so as to more accurately determine the $IC_{50}$. These latter results are reported in Table 2. All samples were run in duplicate.

(B) Antagonism of Apomorphine-Induced Emesis in Dogs

Unfasted beagle dogs of both sexes were used as test subjects. Test compounds and apomorphine were each administered subcutaneously as aqueous solutions, with the test compound being administered 30 minutes prior to the administration of the apormorphine. The dogs were observed for 60 minutes after administration of the apomorphine for either emesis or complete protection from emesis (quantal response).

Apomorphine was administered at a dose of 0.3 mg/kg. Since the test compounds were essentially void of apomorphine antagonism, they were administerred at a dose of 3 mg/kg. Failure to reach 50% antagonism (prevention of emesis) at that dosage is reported in Table 1 as >3 mg/kg. Since the comparison compounds such as metoclopramide, alizapride, clebopride and domperidone have dopaminergic antagonist activity, lower doses of these standards were administered, and the calculated $ED_{50}$'s are reported in Table 1. All tests were run in at least two dogs.

(C) Antagonism of Cisplatin-Induced Emesis in the Ferret

Adult, male, castrated Fitch ferrets (1.0–1.5 kg) are anesthetized with pentobarbital sodium (30 mg/kg, i.p.). The ventral and dorsal area of the neck is shaved and a 3 cm incision is made. The left jugular vein is exposed and ligated with a silk suture at the cephalic end. The indwelling catheter is constructed of Silastic tubing 18 cm in length (0.020 inch I.D.×0.037 inch O.D.) with a 2 cm polyethylene sleeve (0.045 inch I.D.×0.062 inch O.D.) filled with heparin (1000 units/ml) and sealed at the exposed end with a 23 gauge×1 inch needle crimped at both ends. A small cut is made in the jugular and the catheter inserted, allowing the free end to be delivered through a 13 gauge×5 cm trochar under the skin and attached to the nape of the neck with a silk suture. The ferrets are housed in individual cages and allowed 2–4 days recovery before testing.

On the test day, the test compounds were administered i.v. (3 mg/ml or 1 ml/kg) via the catheter 5 minutes prior to and 90 minutes after cisplatin. The cisplatin solution was prepared by adding 70° C. physiological saline, stirring and sonicating until dissolved. The resulting solution (4 mg/ml) was maintained at 40° C. and administered i.v. (12 ml/kg) via the catheter. Following administration of cisplatin, the ferrets were observed continuously for four hours and emetic episodes recorded. Two or more emetic episodes within a one-minutes period was considered as a single episode.

The ferrets were euthanized with T-61 i.v. at the termination of the experiment, and proper placement of the catheter was verified. The results of the test are shown in Table 1 as the percent protection (graded response) compared to saline treatment. The dosage and number of animals also are shown for each test.

(D) Gastrokinetic Activity

A number of compounds of this invention have been found to enhance contraction of field-stimulated guinea pig ileum preparations. This activity is considered to be correlated with gastrokinetic (prokinetic) activity in vivo, i.e. enhancement of gastric motility and gastric emptying.

Normal, male guinea pigs (Hartley; Charles River) weighing 300–400 are sacrificed by cervical dislocation. The terminal portion of the ileum was removed after discarding a 10 cm segment nearest to the ileocecal junction. The strips, 3–4 cm in length, were mounted in a 20 ml organ bath containing Krebs physiological buffer solution. The buffer was bubbled with 95% $O_2$–5% $CO_2$ and kept at 37° C. The resting tension was adjusted to 1.0 g, and the tissues were equilibrated without stimulation for 15 minutes. For electrical stimulation, a platinum wire (cathode) was threaded up through the lumen and another platinum wire (anode) was attached to the glass rod that suspended the muscle. Tissues were stimulated coaxially at 1.5 times the voltage necessary to produce maximum twitch height, with single pulses, 0.5 msec in duration, delivered once every 10 seconds. After the 15 minute equilibration period (without stimulation), the stimulator (Grass S88 Stimulator) was turned on and the tissues were allowed to stabilize for approximately 1 hour, or until the twitch height remained constant, with washes every 20 minutes. The contractions of the ileum were recorded isometrically by means of a force displacement transducer (Grass FTO3C) and displayed on a Dynograph recorder. Some of the compounds of Formula I which showed increased contractions of field stimulated guinea pig ileum preparations are listed in Table 2, with the average % maximum increase, minimum effective concentratin ($\mu$m), effective concentration$_{30}$ ($EC_{30}$) and, in some instances, effective concentration$_{50}$ ($EC_{50}$) ($\mu$M).

TABLE 1

| | Dopaminergic Antagonism and Antiemetic Activity | | | |
|---|---|---|---|---|
| | $^3$H—Spiperone | Antagonism of Apomorphine-Induced | Antagonism of Cisplatin-Induced Emesis in the Ferret | |
| Compound of Example | Displacement $IC_{50}$(nm) | Emesis in the Dog $ED_{50}$ (mg/kg, s.c.) | Dose (mg/kg, i.v.) × 2 (Number of Animals = 3) | % Protection |
| 1 | >1000 | >3 | 3 | 76 |
| 2 | >1000 | >3 | 3 | 68 |
| 3 | >1000 | >3 | 3 | 82 |
| 4 | >1000 | >3 | 3 | 100 |
| 5 | >1000 | >3 | 3 | 90 |
| 6 | >1000 | >3 | 3 | 100 |
| 7 | >1000 | >3 | 3 | 95 |
| 8 | >1000 | >3 | 3 | 95 |
| 9 | >1000 | >3 | 3 | 100 |
| 10 | >1000 | >3 | 3 | 100 |
| 11 | >1000 | >3 | 3 | 90 |
| 12 | >1000 | >3 | 3 | 86 |
| 13 | >1000 | >3 | 3 | 90 |
| 14 | >1000 | >3 | 3 | 62 |
| 15 | >1000 | >3 | 3 | 30 |
| 16 | >1000 | >3 | 3 | 21 |

TABLE 1-continued

Dopaminergic Antagonism and Antiemetic Activity

| Compound of Example | $^3$H—Spiperone Displacement IC$_{50}$(nm) | Antagonism of Apomorphine-Induced Emesis in the Dog ED$_{50}$ (mg/kg, s.c.) | Antagonism of Cisplatin-Induced Emesis in the Ferret | |
|---|---|---|---|---|
| | | | Dose (mg/kg, i.v.) × 2 (Number of Animals = 3) | % Protection |
| 18 | >1000 | >3 | 3 | 72 |
| 19 | >1000 | >3 | 3 | 72 |
| 20 | >1000 | >3 | 3 | 50 |
| 21 | >1000 | >3 | 3 | 49 |
| 24 | >1000 | >3 | 3 | 67 |
| 25 | >1000 | >3 | 1 | 58 |
| 26 | >1000 | >3 | 3 | 90 |
| 27 | >1000 | >3 | 1 | 90 |
| 28 | >1000 | >3 | 1 | 82 |
| 29 | >1000 | >3 | 1 | 44 |
| 30 | >1000 | >3 | 3 | 100 |
| 31 | >1000 | >3 | 1 | 67 |
| 32 | >1000 | >3 | 1 | 72 |
| 33 | >1000 | >3 | 1 | 54 |
| 34 | >1000 | >3 | 1 | 54 |
| 35 | >1000 | >3 | 3 | 72 |
| 36 | >1000 | >3 | 3 | 86 |
| 37 | >1000 | >3 | 3 | 57 |
| 38 | >1000 | >3 | 3 | 57 |
| 39 | >1000 | >3 | 3 | 71 |
| 40 | >1000 | >3 | 3 | 62 |
| 41 | >1000 | >3 | 3 | 81 |
| 42 | >1000 | >3 | 3 | 95 |
| 43 | >1000 | >3 | 3 | 67 |
| 44 | >1000 | >3 | 3 | 71 |
| 45 | >1000 | >3 | 3 | 80 |
| 46 | >1000 | >3 | 3 | 76 |
| 47 | >1000 | >3 | 3 | 8 |
| 48 | >1000 | >3 | 3 | 47 |
| 49 | >1000 | >3 | 3 | 62 |
| 50 | >1000 | >3 | 3 | 62 |
| 51 | >1000 | >3 | 3 | 71 |
| 52 | >1000 | >3 | 3 | 95 |
| 53 | >1000 | >3 | 3 | 91 |
| 54 | >1000 | >3 | 3 | 81 |
| 55 | >1000 | >3 | 3 | 66 |
| 56 | >1000 | >3 | 3 | 81 |
| 57 | >1000 | >3 | 3 | 66 |
| 58 | >1000 | >3 | 3 | 66 |
| 59 | >1000 | >3 | 3 | 66 |
| 60 | >1000 | >3 | 3 | 52 |
| 61 | 760 | >3 | 3 | 71 |
| 62 | >1000 | >3 | 3 | 71 |
| Metoclopramide | 310 | 0.5 | 3* | 89 |
| Alizapride | 290 | 0.3 | 3 | 27 |
| Clebopride | 11 | 0.04 | 3 | 70 |
| Domperidone | 4.1 | 0.2 | 3 | 50 |

*Number of animals = 4

TABLE 2

Gastrokinetic Activity

| Compound of Example | Number of Preparations | Average % Maximum Increase | Minimum Effective Concentration (μm) | EC$_{30}$ (95% C.L.) EC$_{50}$ (95% C.L.) | |
|---|---|---|---|---|---|
| 4 | 4 | 58% at 10 μM | 0.1 | 1.5 | (1.1–2.0) |
| | | | | 5.2 | (3.8–7.8) |
| 14 | 6 | 55% at 30 μM | 0.1 | 4.3 | (3.2–5.9) |
| | | | | 18 | (12–28) |
| 16 | 6 | 72% at 100 μM | 0.03 | 0.5 | |
| | | | | 3.7 | (2.0–9.3) |
| 17 | 5 | 41% at 10 μM | 0.3 | 5.4 | (3.6–9.1) |
| | | | | 15 | (8.8–44) |
| 19 | 6 | 39% at 3 μM | 0.1 | 1.7 | (1.2–2.7) |
| | | | | 5.9 | (3.5–18) |
| 21 | 6 | 88% at 30 μM | 0.1 | 0.57 | (0.24–1.0) |
| | | | | 2.3 | (1.3–4.3) |
| 36 | 4 | 55% at 10μM | 0.1 | 0.5 | (0.09–1.4) |
| | | | | 4.6 | (1.7–56) |
| 37 | 4 | 83% at 300 μM | | 0.72 | (0.28–1.4) |
| | | | | 6.6 | (3.5–1.3) |
| 40 | 6 | 56% at 10 μM | 0.1 | 0.9 | (0.5–1.5) |
| | | | | 5.5 | (3.0–15) |
| 48 | 4 | 47% at 10 μM | 0.1 | 2.3 | (1.8–21) |
| | | | | 13 | (9.4–21) |

TABLE 2-continued

| Compound of Example | Number of Preparations | Gastrokinetic Activity | | EC$_{30}$ (95% C.L.) | |
| --- | --- | --- | --- | --- | --- |
| | | Average % Maximum Increase | Minimum Effective Concentration (μm) | EC$_{50}$ (95% C.L.) | |
| 50 | 4 | 45% at 30 μM | 1.0 | 12 | (9–14) |
| | | | | 39 | (30–55) |
| 51 | 6 | 51% at 10 μM | 0.03 | 0.23 | (0.25–0.51) |
| | | | | 5.0 | (2.0–43) |
| 56 | 4 | 59% at 30 μM | 0.1 | 1.1 | (0.59–1.8) |
| | | | | 7.3 | (4.2–16) |
| 58 | 4 | 72% at 30 μM | 0.3 | 1.5 | (0.8–2.5) |
| | | | | 5.6 | (3.4–10) |
| 59 | 6 | 38% at 10 μM | 1.0 | 5.2 | (3.2–11) |
| | | | | 20 | (10–134) |
| 60 | 6 | 66% at 30 μM | 0.1 | 0.88 | (0.58–1.2) |
| | | | | 4.8 | (3.3–7.4) |
| Metoclopramide | 10 | 62% at 30 μM | 0.03 | 1.6 | (1.0–2.4) |
| | | | | 11 | (7.0–20) |

Tables 1 and 2 show the compounds of Formula I to have useful antiemetic and gastrokinetic activity, while Table 1 shows that the compounds are essentially free of dopaminergic antagonism, thus avoiding the side-effect liabilities of the currently available substituted benzamide antiemetic and gastrokinetic agents.

The compounds of Formula I may be administered either orally, parenterally or by suppository. When utilized as an antiemetic in the case of patients receiving cancer chemotherapeutic agents such as cisplatin, it preferably is given as an intravenous infusion diluted in a larger volume of parenteral solution (such as Dextrose-5% in water, Dextrose-5% in 0.45% sodium chloride, Ringer's Injection or Lactated Ringer's Injection). When utilized as a gastrokinetic agent, the compounds preferably are given orally if the symptoms are not severe. With severe symptoms, therapy preferably should begin with i.m. or i.v. administration until the severe symptoms subside, at which time oral administration may be instituted.

The dosage of the compounds of Formula I depend on the purpose for which they are taken (antiemetic or gastrokinetic), the particular compound administered, the age, weight and general health of the patient, as well as the severity of the malady, and is within the discretion of the physician.

When taken for gastrokinetic purposes, the compounds of Formula I are generally administered at a dosage of from 1 to 100 mg and preferably from 5 to 50 mg, from 2 to 5 times a day and preferably four times a day, e.g. before each meal and at bedtime.

For the prevention of nausea and vomiting associated with emetogenic cancer chemotherapeutic agents, the compounds of Formula I are generally administered (diluted in a larger volume of parenteral solution) at a dosage of from 0.1 to 50 mg/kg and preferably from 0.5 to 10 mg/kg, given several times per day. The particular dose to be used depends on the factors mentioned above, as well as the emetogenicity of the cancer chemotherapeutic agent. In general, the first dose should be given prior to the administration of the cancer chemotherapeutic agent, e.g. 30 minutes, and then every 2–8 hours after administration of the chemotherapeutic agent, until the symptoms of nausea and vomiting subside or become less severe, e.g. for 12 to 24 hours.

Tablets and capsules for oral use preferably are in unit dosage form, and may contain conventional excipients such as binding agents, fillers, tabletting lubricants, disintegrants, wetting agents and the like. The tablets may, if desired, be film coated by conventional techniques. Liquid preparations for oral use may be in the form of aqueous or oily suspensions, solutions, emulsions, syrups or elixirs, or may be a dry product for reconstitution with water or other suitable vehicle before use. Liquid preparations may contain conventional additives such as suspending agents, emulsifying agents, non-aqueous vehicle (including edible oils), preservatives, as well as flavoring and/or coloring agents.

For parenteral administration, the compounds of Formula I are combined with a sterile vehicle. Depending on the vehicle and concentration of active ingredient, the dosage form may be a solution or suspension. The vehicle normally will comprise sterile water, at least in large part, although saline solutions, glucose solutions and the like may be utilized. Injectable suspensions also may be used, in which case conventional suspending agents may be employed. Conventional preservatives, buffering agents and the like also may be added to the parenteral dosage forms.

For solid dosage forms, either the free base or a salt of the compounds of Formula I may be used. In the case of aqueous solutions, either oral or parenteral, it is often preferred to utilize a salt of the compounds of Formula I, due to the usual greater solubility of the salts in aqueous solutions.

It is especially advantageous to formulate the above pharmaceutical compositions in unit dosage form for ease of administration and uniformity of dosage. Unit dosage form refers to physically discrete units suitable as unitary doses, each unit containing a predetermined quantity of active ingredients, calculated to produce the desired effect, in association with the desired pharmaceutical carrier.

This invention also includes pharmaceutical compositions for the alleviation of nausea and vomiting, which comprises an effective antiemetic amount of at least one compound of Formula I, or a salt, hydrate or solvate thereof, plus a pharmaceutically acceptable carrier.

This invention also includes pharmaceutical compositions for the treatment of disorders related to impaired gastric motility, which comprise an effective gastric motility facilitating amount of at least one compound of Formula I, or a salt, hydrate or solvate thereof, and a pharmaceutically acceptable carrier.

This invention also relates to a method of alleviating nausea and vomiting in a warm-blooded mammal in need thereof, which comprises administering to said mammal an effective antiemetic amount of at least one compound of Formula I, or a salt, hydrate or solvate thereof, in a pharmaceutically acceptable carrier.

This invention also relates to a method of treating disorders related to impaired gastric motility in a warm-blooded mammal, which comprises administering to said mammal an effective gastric motility facilitating amount of at least one compound of Formula I, or a salt, hydrate or solvate thereof, in a pharmaceutically acceptable carrier.

As used herein and in the claims, the term "(lower)alkyl" means a straight or branched alkyl chain containing from 1 to 6 carbon atoms. Similarly, the terms "(lower)alkenyl" and "(lower)alkynyl" refer to alkenyl or alkynyl chains containing from 2 to 6 carbon atoms. All temperatures given herein are in degrees Centigrade.

Preparation No. 1

4-Amino-5-chloro-N-[2-(diethylamino)ethyl]-2-hydroxybenzamide (A)

4-Amino-5-chloro-N-[2-(diethylamino)ethyl]-2-hydroxybenzamide Hydrochloride

To a cooled (<10°) stirred suspension of sodium hydride (57.44 g of 60%, 1.436 moles) in DMF (1275 ml) was added dropwise a cold solution of ethanethiol (89.22 g, 1.436 moles) in DMF (250 ml). After hydrogen evolution had ceased 4-amino-5-chloro-N-[2-(diethylamino)ethyl]-2-methoxybenzamide (287.0 g, 0.957 moles) (prepared according to U.S. Pat. No. 3,357,978 [1965]) was added and the mixture was heated in an oil bath at 100°-105° for 90 minutes. The solvent was removed in vacuo and the residue partititioned between methylene chloride (800 ml) and water (400 ml). The aqueous layer was washed with another portion of methylene chloride and the combined organic extracts were backwashed with water (150 ml). The combined aqueous phase was cooled in an ice bath and treated with concentrated hydrochloric acid (200 ml). After 20 minutes the precipitate was collected by filtration, sucked briefly on the filter, slurried with methanol (500 ml) and again filtered. The product was dried in vacuo to give 302.3 g (98%) of the title compound as a light beige solid, mp 235°-237°.

Anal. Calc'd for $C_{13}H_{20}ClN_3O_2.HCl$: C, 48.46; H, 6.57; N, 13.04; Cl, 22.00. Found: C, 47.67; H, 6.73; N, 12.84; Cl, 21.43.

(B)

4-Amino-5-chloro-N-[2-(diethylamino)ethyl]-2-hydroxybenzamide

To stirred concentrated ammonium hydroxide (6 ml) was added 4-amino-5-chloro-N-[2-(diethylamino)ethyl]-2-hydroxybenzamide hydrochloride (3.0 grams, 0.0093 mole) and the mixture stirred an additional five minutes followed by the addition of three to four ml of water and another five minute stirring. After filtration the solid was washed two times with three ml of water each time to give, after drying, 2.37 g of the title compound, mp 134°-136° C. NMR spectrum (90 MHz) in CDCl₃ gave the following resonances δ: 7.26 (s, 1H); 6.90 (s, 1H); 6.14 (s, 1H); 4.39 (s, 2H); 3.40 (s, 2H); 2.60 (multiplet, 6H); 1.06 (t, 6H).

Preparation No. 2

4-Amino-5-chloro-N-[2-(diethylamino)ethyl]-2-hydroxybenzamide (Alternate Procedure)

A mixture of 4-amino-5-chloro-N-[2-(diethylamino)ethyl]-2-methoxybenzamide (29.5 g, 0.1 mole), sodium hydroxide pellets (4.0 g, 0.1 mole) and 1,2-propanediol (70 ml) was stirred and heated under reflux for 20 hours followed by concentration in vacuo. The residue was treated with 1N HCl (100 ml) and again concentrated in vacuo. The residue was chromatographed on silica using methylene chloride (90), methanol (10), ammonia (0.5) solvent system. The appropriate fractions were combined and concentrated in vacuo and the residue crystallized from ether to give 9.3 g of product. This was dissolved in hot water, and the solution filtered over charcoal. The filtrate was cooled and filtered to give 6.7 g of tan colored title compound, mp 126°-7° (U.S. Pat. No. 3,357,978 reports mp 160°).

Anal. Calc'd. for $C_{13}H_{20}ClN_3O_2$: C, 54.64; H, 7.05; N, 14.70. Found: C, 54.44; H, 7.15; N, 14.65.

Preparation No. 3

Tetra-n-butyl ammonium salt of 4-amino-5-chloro-N-[2-(diethylamino)ethyl]-2-hydroxybenzamide A solution of 4-amino-5-chloro-N-[2-(diethylamino)ethyl]-2-hydroxybenzamide hydrochloride (10 g, 0.031 mmole), 5 g sodium hydroxide and 100 ml was treated with tetra-n-butylammonium hydrogen sulfate (10.6 g, 0.031 mmole) with stirring. The crystals were collected, washed with water and dried (14.7 g, 87%). Recrystallization from ethyl acetate gave the title compound containing one-half mole of water, mp. 136.5°-138.5°.

Anal. Calc'd. for $C_{29}H_{55}ClN_4O_2.0.5H_2O$: C, 64.95; H, 10.53; N, 10.44; H₂O, 1.71. Found: C, 65.06; H, 10.42; N, 10.40; H₂O, 1.41.

EXAMPLE 1

4-Amino-5-chloro-N-[2-(diethylamino)ethyl]-2-(2-methoxyethoxy)benzamide

A mixature of 4-amino-5-chloro-N-[2-(diethylamino)ethyl]-2-hydroxybenzamide hydrochloride (2.50 g, 7.76 mmoles), 2-chloro-ethylmethylether (1.47 g, 15.5 mmoles), potassium carbonate (2.14 g, 15.5 mmoles) and sodium bromide (0.80 g, 7.76 mmoles) in 40 ml of dimethylformamide (DMF) was stirred at reflux for four hours. The DMF was removed under vacuum and the residue was redissolved in methylene chloride and washed with water and dilute NaOH. The solvent was evaporated and the product was chromatographed using a gradient elution of methanol-methylene chloride containing 0.25% NH₄OH. The appropriate fractions were combined and evaporated to yield 2.34 g (87.6%) of cream-colored solid. Recrystallization of the residue from ethyl acetate gave the title compound as a white solid, mp 108°-110.5°. The NMR spectrum (90 MHz) in CDCl₃ gave the following resonances: δ 8.19 (s, 1H); 6.35 (s, 1H); 4.5 (bs, 2H); 4.2 (m, 2H); 3.8 (m, 2H); 3.5 (m, 2H); 3.49 (s, 3H); 2.59 (m, 6H); 1.02 (t, 6H).

Anal. Calc'd. for $C_{16}H_{26}ClN_3O_3$: C, 55.89; H, 7.62; N, 12.22 Cl, 10.31. Found: C, 55.66; H, 7.66; N, 12.15 Cl, 10.35.

EXAMPLE 2

4-Amino-5-chloro-N-[2-(diethylamino)ethyl]-2-(2-hydroxyethoxy)benzamide

The general procedure of Example 1 was repeated, except that the 2-chloroethylmethyl ether utilized therein was replaced by 1.50 g (18.62 mmoles) of 2-chloroethanol. The crude product was purified by flash chromatography on 50 g of silica gel (230–400 mesh) using a gradient elution of methanol-methylene chloride containing 0.25% ammonia. The appropriate fractions were combined and the solid residue was recrystallized from acetonitrile to yield 1.30 g (42.5%) of the title compound, mp 144°–146.5°. The NMR spectrum (90 MHz) in DMSO/CDCl$_3$ gave the following resonances: δ 8.1 (s, 1H); 6.4 (s, 1H); 4.75 (bs, 2H); 4.05 (m, 4H); 3.6 (m, 2H); 2.7 (m, 6H); 1.1 (t, 6H).

Anal. Calc'd. for $C_{15}H_{24}ClN_3O_3$: C, 54.62; H, 7.33; N, 12.74 Cl, 10.31. Found: C, 54.67; H, 7.88; N, 12.92 Cl, 10.69.

EXAMPLE 3

4-Amino-5-chloro-N-[2-(diethylamino)ethyl]-2-(2,2-dimethoxyethoxy)benzamide

A mixture of 4-amino-5-chloro-N-[2-(diethylamino)ethyl]-2-hydroxybenzamide hydrochloride (8.06 g, 0.025 mole), chloroacetaldehyde dimethyl acetal (6.23 g; 0.05 mole), potassium carbonate (6.91 g, 0.05 mole) and sodium bromide (2.57 g, 0.025-mole) in 100 ml of dry DMF was stirred at reflux for 8 hours. After four hours at reflux an additional amount of the alkylating agent (6.23 g, 0.05 mole) was added. The mixture was filtered and the DMF was removed under vacuum. The oily residue was redissolved in methylene chloride and washed sequentially with water, aqueous 1.0N NaOH, water and saturated NaCl solution. The solvent was evaporated and the product was further purified by chromatography using a gradient elution of methanol-methylene chloride containing 0.25% of ammonia. The appropriate fractions were combined and evaporated to give a yellow residue. Recrystallization from ethyl acetate-petroleum ether yielded the title compound as a white solid; wt. 5.5 g (59.8%), mp 64°–67°. The NMR spectrum (90 MHz) in CDCl$_3$ gave the following resonances: δ 8.19 (s, 1H); 6.32 (s, 1H); 4.83 (t, 2H); 4.42 (bs, 2H); 4.08 (d, 2H); 3.55 (m, 2H); 3.50 (m, 2H); 2.41 (m, 6H); 1.1 (t, 6H).

Anal. Calc'd. for $C_{17}H_{28}ClN_3O_4$: C, 54.61; H, 7.55; N, 11.24 Cl, 9.48 Found: C, 54.21; H, 7.42; N, 11.07 Cl, 10.34

EXAMPLE 4

4-Amino-4-chloro-N-[2-(diethylamino)ethyl]-2-[(2-methoxyethoxy)methyloxy]benzamide To a well stirred suspension of sodium hydride (0.34 g of 60%, 0.014 mole) in 5 ml dry DMF was added a solution of 4-amino-5-chloro-N-[2-(diethylamino)ethyl]-2-hydroxy benzamide (3.57 g, 0.012 mole) in 15 ml dry DMF at room temperature over 18 minutes. The mixture was then stirred an additional hour giving essentially a clear solution. To this was added dropwise a solution of 2-methoxyethoxymethyl chloride (1.74 g, 0.014 mole) in 5 ml dry DMF. After an additional four hours at ambient temperature, the mixture was concentrated in vacuo, and the residue partitioned between water (200 ml) and methylene chloride (75 ml). The aqueous phase was extracted twice with 75 ml portions of methylene chloride. After combining, the organic phase was washed three times with 50 ml of 10% aqueous soldium hydroxide and three times with brine; dried over sodium sulfate, filtered, concentrated in vacuo, to give 4.26 grams of residue. Crystallization from ether gave 2.53 grams of the title compound, mp 79°–81° C. The NMR spectrum (90 MHz) in CDCl$_3$ gave the following resonances: δ 8.18 (s, 2H); 6.61 (s, 1H); 5.40 (s, 2H); 4.40 (s, 2H); 3.84 (m, 2H); 3.50 (m, 4H); 3.44 (s, 3H); 2.56 (m, 6H); 1.04 (t, 6H).

Anal. Calc'd. for $C_{17}H_{28}ClN_3O_4$: C, 54.60; H, 7.56; N, 11.24. Found: C, 54.16; H, 7.75; N, 11.16.

EXAMPLE 5

4-Amino-5-chloro-N-[2-(diethylamino)ethyl]-2-(2-propanon-1-yl)oxybenzamide

To a stirred suspension of 4-amino-5-chloro-N-[2-(diethylamino)ethyl]-2-hydroxybenzamide hydrochloride (5.0 g, 16 mmoles) and potassium carbonate (10.62 g, 77 mmoles) in DMF (25 ml) was added chloroacetone (2.32 g of 90%, 22 mmoles) and the mixture stirred vigorously for 5 hours, followed by pouring into water (130 ml) and filtration to give, after drying, 4.57 g of crude product. This was dissolved in methylene chloride and filtered over a short alumina column, followed by concentration and recrystallization of the residue from toluene to give 4.16 g (78%) of the title compound as white solid, mp 105°–106.5°. The NMR (90 MHz) in CDCl$_3$ gave the following resonances: δ 8.44 (s, 1H); 6.16 (s, 1H); 4.72 (s, 2H); 4.4 (s, 2H); 3.6 (m, 2H); 2.68 (m, 6H); 2.28 (s, 3H); 1.08 (t, 6H).

Anal. Calc'd. for $C_{16}H_{24}ClN_3O_3$: C, 56.21; H, 7.08; N, 12.29 Cl, 10.37. Found: C, 56.14; H, 6.97; N, 12.29 Cl, 10.29.

EXAMPLE 6

4-Amino-2-(2-phenyl-2-oxoethoxy)-5-chloro-N-[2-(diethylamino)ethyl]benzamide To a stirred suspension of sodium hydride (320 mg of 60%, 8 mmoles, washed with n-pentane) in DMF (15 ml) was added 4-amino-5-chloro-N-[2-(diethylamino)ethyl]-2-hydroxybenzamide hydrochloride (1.289 g, 4 mmoles) and the mixture stirred for 20 minutes followed by addition of chloroacetophenone (619 mg, 4 mmoles). The mixture was stirred 4 hours, poured into ice-cold water (50 ml) whereupon a solid separated out. This was isolated by filtration, dried and recrystallized from methanol to give 810 mg (50%) of the title compound as white solid mp 153°–4°. The NMR spectrum (90 MHz) in CDCl$_3$ gave the following resonances: δ 8.64 (bs, 1H); 8.2 (s, 1H); 8 (m, 2H); 7.6 (m, 3H); 6.22 (s, 1H); 5.36 (s, 2H); 4.4 (s, 2H); 3.52 (m, 2H); 2.64 (m, 6H); 1.01 (m, 6H).

Anal. Calc'd. for $C_{21}H_{26}ClN_3O_3$: C, 62.45; H, 6.49; N, 10.40 Cl, 8.78. Found: C, 62.54; H, 6.39; N, 10.83 Cl, 8.68.

EXAMPLE 7

(A)

4-Amino-2-(butan-2-on-3-yl)oxy-5-chloro-N-[2-(diethylamino)ethyl]benzamide

To a stirred suspension of sodium hydride (40 mg of 60%, 1 mmole, washed with n-pentane) in DMF (2 ml) was added 4-amino-5-chloro-N-[2-(diethylamino)ethyl]-2-(2-propanon-1-yl)oxybenzamide, prepared in Example 5, (0.349 g, 1 mmole) under nitrogen. The mixture was stirred until evolution of hydrogen subsided, when iodomethane (0.07 ml, 160 mg, 1.0 mmol) was added and stirring continued for 1 hour. The mixture was partitioned between water and methylene chloride, and the organic phase washed with water, dried, concentrated and the residue chromatographed on deactivated silica using methylene chloride (100), methanol (4.5), ammonia (0.5) solvent system. The appropriate fractions were combined to give 160 mg of the title compound as a heavy oil. The NMR spectrum (90 MHz) in $CDCl_3$ gave the following resonances: δ 8.24 (s, superimposed over broad singlet, 2H); 6.08 (s, 1H); 4.70 (q, J=5.4 Hz, 1H); 4.44 (s, 2H); 3.56 (m, 2H); 2.62 (m, 6H); 2.2 (s, 3H); 1.6 (d, J=5.4 Hz, 3H); 1.04 (t, 6H).

(B)

4-Amino-2-(butan-2-on-3-yl)oxy-5-chloro-N-[2-(diethylamino)ethyl]benzamide hydrochloride To a stirred suspension of 4-amino-5-chloro-N-[2-(diethylamino)ethyl]-2-hydroxybenzamide hydrochloride (1.94 g, 6 mmoles) and potassium carbonate (4.16 g, 30 mmoles) in DMF (10 ml) was added 3-chloro-2-butanone (0.95 g, 8.9 mmoles) and the mixture stirred for 3 hours, followed by pouring into water and extraction with methylene chloride. The extract was washed well with water, dried and concentrated in vacuo. The residue was dissolved in 1-propanol and treated with 2N HCl followed by concentration to give an oily residue. This was crystallized from acetone and the product recrystallized from 2-propanol to give 1.4 g of the title compound mp 98° C. as the hemihydrate.

Anal. Calc'd. for $C_{17}H_{26}ClN_3O_3 \cdot HCl \cdot 0.5H_2O$: C, 51.00; H, 6.80; N, 10.50; Cl, 17.71. Found: C, 51.26; H, 6.86; N, 10.51; Cl, 17.38.

(C)

4-Amino-2-(butan-2-on-3-yl)oxy-5-chloro-N-[2-(diethylamino)ethyl]benzamide Hydrochloride To a stirred suspension of 4-amino-5-chloro-N-[2-(diethylamino)ethyl]-2-hydroxybenzamide hydrochloride (19.4 g, 60 mmoles), potassium carbonate (41.6 g, 0.3 moles) and sodium iodide (10 g) in DMF (100 ml) was added 3-chloro-2-butanone (9.5 g, 89 mmoles) and the mixture vigorously stirred and heated to 70°–80° for 2 hours followed by cooling and partition between water and methylene chloride. The organic phase was washed with water, dried and concentrated. The residue was treated with 2N HCl and azeotroped with n-propanol, and crystallized from acetone to give 19.0 g (81%) of the title compound mp 177°–179°.

EXAMPLE 8

4-Amino-5-chloro-N-[2-(diethylamino)ethyl]-2-[(3-methyl)-5-hexen-2-on-3-yl]oxybenzamide To a stirred suspension of sodium hydride (0.2 g of 60%, 5 mmoles, washed with n-pentane) in DMF (10 ml) was added dropwise a solution of 4-amino-2-(butan-2-on-3-yl)oxy-5-chloro-N-[2-(diethylamino)ethyl]benzamide (1.78 g, 5 mmoles) in DMF (10 ml). After hydrogen evolution subsided, allyl bromide (690 mg, 5.7 mmoles) was added and the mixture stirred for 72 hours, followed by partition between water and methylene chloride. The organic phase was washed with water, dried and concentrated. The residue was chromatographed on deactivated silica, using methylene chloride (100), methanol (4), ammonia (0.5). The appropriate fractions were combined to give 0.58 g of crude product as a heavy oil. This was crystallized from ether to give the title compound as a white solid, mp 138°+140°. The NMR spectrum (90 MHz) in $CDCl_3$ gave the following resonances: δ 8.24 (s, 1H); 8.0 (bs, 1H); 5.92 (s, 1H); 5.9–5.0 (m, 4H); 4.38 (bs, 2H); 3.58 (m, 2H); 3.0–2.3 (m, 8H); 2.28 (s, 3H); 1.62 (s, 3H); 1.04 (t, 6H).

Anal. Calc'd. for $C_{20}H_{30}ClN_3O_3$: C, 60.67; H, 7.68; N, 10.61. Found: C, 60.34; H, 7.67; N, 10.54.

EXAMPLE 9

4-Amino-5-chloro-2-(cyclohexanon-2-yl)oxy-N-[2-(diethylamino)ethyl]benzamide

A suspension of 4-amino-5-chloro-N-[2-(diethylamino)ethyl]-2-hydroxybenzamide hydrochloride (6.4 g, 20 mmoles) and potassium carbonate (13.8 g, 0.1 mole) in DMF (34 ml) and 2-chlorocyclohexanone (3.8 g, 28.6 mmoles) was stirred for 4 days, followed by partition between water and methylene chloride. The organic phase was washed well with water, dried and concentrated. The residue was chromatographed on deactivated silica using methylene chloride (100), methanol (4), ammonia (0.5) as the solvent system. The appropriate fractions were combined and further purified by low pressure liquid chromatography to give 1.0 g of the title compound as a colorless foam. The NMR spectrum (90 MHz) in $CDCl_3$ gave the following resonances: δ 8.4 (bs, 1H); 8.16 (s, 1H); 6.14 (s, 1H); 4.7 (m, 1H); 4.3 (s, 2H); 3.56 (q, J=7.2 Hz, 2H); 2.62 (m, 6H); 2.3–1.4 (m, 8H); 1.04 (t, J=7.2 Hz, 6H).

Anal. Calc'd. for $C_{19}H_{28}ClN_3O_3$: C, 59.75; H, 7.39; N, 11.00; Cl, 9.29. Found: C, 59.40; H, 7.32; N, 10.94; Cl, 8.99.

EXAMPLE 10

4-Amino-5-chloro-N-[2-(diethylamino)ethyl]-2-[(2-hydroxyimino)propan-1-yl]oxybenzamide A mixture of 4-amino-5-chloro-N-[2-(diethylamino)ethyl]-2-propanol-1-yl)oxybenzamide (1.0 g, 2.9 mmoles) and hydroxylamine hydrochloride (0.3 g, 4.3 mmoles) in methanol (20 ml) was heated under reflux for 10 minutes, followed by concentration in vacuo. The residue was partitioned between aqueous sodium carbonate and methylene chloride. The organic phase was dried and concentrated, and the residue dissolved in methanol, treated with charcoal and filtered. The filtrate was concentrated in vacuo and the residue crystallized from ethyl acetate-n-pentane to give 0.58 g (56%) of the title compound containing 0.25 mole of water of crystallization, mp 112°–113°. The NMR spectrum (90 MHz) in $CDCl_3$ gave the following resonances: δ 9.16 (s, 1H); 8.32 (s, 1H); 6.36 (s, 1H); 4.72 (s, 2H); 4.36 (s, 2H); 3.68 (m, 2H); 2.68 (m, 6H); 1.92 (s, superimposed over a broad absorption, 4H); 1.12 (t, 6H).

Anal. Calc'd. for $C_{16}H_{25}N_4O_3 \cdot \frac{1}{4}H_2O$: C, 53.18; H, 7.11; N, 15.50; Cl, 9.80. Found: C, 53.18; H, 7.01; N, 15.36; Cl, 9.52.

EXAMPLE 11

4-Amino-5-chloro-N-[2-(diethylamino)ethyl]-2-[(2-methoxyimino)propan-1-yl]oxybenzamide The general procedure of Example 10 was repeated except that the hydroxylamine hydrochloride used therein was replaced by methoxyamine hydrochloride, and the reaction was conducted at ambient temperature (16 hours) to give the title compound in 70% yield a as white solid mp 121°–123° from methylene chloride-n-pentane. The NMR spectrum (90 MHz) in $CDCl_3$ was similar to that of Example 10 with an additional singlet at δ 3.92 (3H).

Anal. Calc'd. for $C_{17}H_{27}ClN_4O_3$: C, 55.05; H, 7.34; N, 15.11; Cl, 9.56. Found: C, 54.69; H, 7.48; N, 14.92; Cl, 9.47.

EXAMPLE 12

4-Amino-5-chloro-N-[2-(diethylamino)ethyl]-2-(2-hydroxypropan-1-yl)oxybenzamide

A mixture of 4-amino-5-chloro-N-[2-(diethylamino)ethyl]-2-(2-propanon-1-yl)oxybenzamide (1.28 g, 3.7 mmoles) and sodium borohydride (80 mg, 2.1 mmoles) in absolute ethanol (15 ml) was refluxed for 30 minutes, followed by addition of another 50 mg (1.3 mmole) of sodium borohydride and reflux for 10 minutes. The mixture was acidified with 2N HCl and concentrated in vacuo. The residue was partitioned between water and ether, and the ether layer was discarded. The aqueous layer was made basic with $Na_2CO_3$ and the solid filtered off to give 0.80 g (77%) of the title compound mp 149°–150°. The NMR spectrum (90 MHz) in $CDCl_3$ gave the following resonances: δ 8.48 (bs, 1H); 8.16 (s, 1H); 6.28 (s, 1H); 4.4–3.4 (m, 7H); 2.64 (m, 6H); 1.26 (d, J=7.5 Hz, 3H); 1.08 (t, 3H).

Anal. Calc'd. for $C_{16}H_{26}ClN_3O_3$: C, 55.88; H, 7.62; N, 12.22; Cl, 10.31. Found: C, 56.08; H, 7.65; N, 12.05; Cl, 9.80.

EXAMPLE 13

4-Amino-5-chloro-2-cyanomethoxy-N-[2-(diethylamino)ethyl]benzamide

To a stirred suspension of sodium hydride (420 mg of 60%, 10.5 mmoles, washed with n-pentane) in 10 ml DMF was added 4-amino-5-chloro-N-[2-(diethylamino)ethyl]-2-hydroxybenzamide hydrochloride (1.612 g, 5 mmoles) and the mixture stirred for 20 minutes, followed by cooling (ice bath) and addition of chloroacetonitrile (418 mg, 5.5 mmoles) and sodium bromide (100 mg). The mixture was stirred in the cold for 1 hour and at ambient temperature for 16 hours, followed by pouring into a mixture of water and ice, and filtration of the resulting solid. The product was dissolved in methylene chloride and filtered over alumina, followed by concentration in vacuo to give crude product. This was recrystallized from methanol to give 930 mg (57%) of the title compound as white crystalline solid mp 188°–189°. The NMR spectrum (90 MHz) in $CDCl_3$ gave the following resonances: δ 8.1 (s, 1H); 7.78 (bs, 1H); 6.44 (s, 1H); 4.84 (s, 2H); 4.60 (s, 2H); 3.43 (m, 2H); 2.59 (m, 6H); 1.02 (t, 6H).

Anal. Calc'd. for $C_{15}H_{21}ClN_4O_2$: C, 55.47; H, 6.52; N, 17.25; Cl, 10.92. Found: C, 55.85; H, 6.59; N, 16.95; Cl, 10.97.

EXAMPLE 14

4-Amino-5-chloro-[2-(diethylamino)ethyl]-2-(1-cyano)ethoxybenzamide

A mixture of 4-amino-5-chloro-N-[2-(diethylamino)ethyl]-2-hydroxybenzamide hydrochloride (4.036 g, 12.5 mmoles), potassium carbonate (8.56 g, 62 mmoles), 2-chloropropionitrile (1.57 g, 17.54 mmoles) and sodium iodide (300 mg) in DMF (18 ml) was stirred and heated at 50° for 20 hours, followed by pouring into ice-water and filtration to give crude solid. This was dissolved in methylene chloride and filtered over a short alumina column. The filtrate was concentrated and the residue recrystallized from methylene chloride-ether to give 3.57 g (84.4%) of the title compound mp 139°–140°. The NMR spectrum (90 MHz) in $CDCl_3$ gave the following resonances: δ 8.2 (s, 1H); 7.75 (bs, 1H); 6.28 (1, 1H); 4.97 (q, J=7.0 Hz, 1H); 4.5 (bs, 2H); 3.54 (m, 2H); 2.6 (m, 6H); 1.88 (d, J=7.0 Hz, 3H); 1.02 (t, 6H).

Anal. Calc'd. for $C_{16}H_{23}ClN_4O_2$: C, 56.71; H, 6.84; N, 16.53; Cl, 10.46. Found: C, 56.63; H, 6.96; N, 16.53; Cl, 9.64.

EXAMPLE 15

4-Amino-5-chloro-N-[2-(diethylamino)ethyl]-2-(2-methoxy-2-oxoethoxy)benzamide

To a stirred suspension of sodium hydride (420 mg of 60%, 10.5 mmoles) of DMF (10 ml) was added 4-amino-5-chloro-N-[2-(diethylamino)ethyl]-2-hydroxybenzamide hydrochloride (1.612 g, 5 mmoles) and the mixture stirred for 20 minutes, followed by cooling (ice water) and addition of methyl bromoacetate (832 mg, 5.44 mmoles). The mixture was stirred for 20 minutes in the cold and another 10 minutes at ambient temperature followed by pouring into 70 ml of ice-cold water. A separated solid was filtered and dried to give 1.58 g of crude product mp 92°–94°. This was recrystallized from methylene chloride-ether to give 1.21 g of the title compound as a white crystalline solid, mp 94°–95° (67.6% yield). The NMR spectrum (90 MHz) in $CDCl_3$ gave the following resonances: δ 8.2 (s, 1H); 6.16 (s, 1H); 4.7 (s, 2H); 4.40 (bs, 2H); 3.86 (s, 3H); 3.54 (m, 2H); 2.6 (m, 6H); 1.04 (t, 6H).

Anal. Calc'd. for $C_{16}H_{24}ClN_3O_4$: C, 53.70; H, 6.76; N, 11.47; Cl, 9.82. Found: C, 53.57; H, 6.78; N, 11.48; Cl, 9.91.

EXAMPLE 16

4-Amino-2-(2-amino-2-oxoethoxy)-5-chloro-N-[2-(diethylamino)ethyl]benzamide Acetate Monohydrate A well stirred mixture of 4-amino-5-chloro-N-[2-(diethylamino)ethyl]-2-hydroxybenzamide hydrochloride (2.0 g, 6.2 mmoles), potassium carbonate (2.57 g, 18.6 mmoles), sodium iodide (0.93 g, 6.8 mmoles) and 2-chloroacetamide (0.64 g, 6.8 mmoles) was heated at 75° for 3 hours. The mixture was then evaporated in vacuo and the residue partitioned between water and methylene chloride. The aqueous phase was extracted twice with methylene chloride, and the combined extracts treated with an excess of acetic acid followed by concentration in vacuo. The semi-solid residue was treated with methylene chloride (150 ml) and filtered to give a colorless solid. This was recrystallized from acetonitrile to give 1.04 g (41%) of the title compound as an off-white solid, mp. 116°–125°. The NMR spectrum (90 MHz) in $D_2O$ gave the following resonances: δ 7.8 (s, 1H); 6.26 (1H, s); 4.8 (s, 2H); 3.8 (m, 2H); 3.3 (m, 6H); 1.95 (s, 3H); 1.3 (t, 6H).

Anal. Calc'd. for $C_{16}H_{23}ClN_4O_3 \cdot CH_3CO_2H \cdot H_2O$: C, 48.51; H, 6.94; N, 13.31; Cl, 8.43. Found: C, 48.37; H, 6.88; N, 13.26; Cl, 8.32.

EXAMPLE 17

4-Amino-5-chloro-N-[2-(dimethylamino)ethyl]-2-hydroxybenzamide

The general procedure of Preparation 1A was repeated except that the 4-amino-5-chloro-N-[2-(diethylamino)ethyl]-2-methoxybenzamide utilized therein was replaced by 4-amino-5-chloro-N-[2-(dimethylamino)ethyl]-2-methoxybenzamide (prepared according to U.K. Pat. No. 1,793,771). The solvent (DMF) was removed in vacuo, and the residue treated with water and methylene chloride saturated with carbon dioxide, concentrated, and the crude product isolated in 89% yield by extraction with ethanol. A sample was chromatographed on a silica gel column usimg methylene chloride (97), methanol (3), ammonia (0.3) solvent system. The appropriate fractions were combined and concentrated in vacuo. The residue was crystallized from methanol to give the title compound as a colorless solid, mp. 163°–165°.

Anal. Calc'd. for $C_{11}H_{16}ClN_3O_2$: C, 51.26; H, 6.62; N, 16.31; Cl, 13.76. Found: C, 51.46; H, 6.35; N, 16.12; Cl, 13.60.

EXAMPLE 18

4-Amino-5-chloro-N-[2-(diethylamino)ethyl]-2-(2,2-dimethyl-1,3-dioxalan-4-yl)methoxybenzamide A mixture of 4-amino-5-chloro-N-[2-(diethylamino)ethyl]-2-hydroxybenzamide hydrochloride (3.22 g, 10 mmoles), 4-chloromethyl-2,2-dimethyl-1,3-dioxalane (1.65 g, 10 mmoles), potassium carbonate (2.76 g, 20 mmoles), sodium bromide (1.03 g, 10 mmoles), and 40 ml DMF was heated at reflux for 20 hours. The DMF was removed at reduced pressure. The residue was treated with water and extracted with methylene chloride to give a gum. This material was purified using HPLC [Waters prep 500, silica cartridge, methylene chloride-2-propanol-concentrated ammonia (100:1:0.5) for elution]. Combination of the appropriate fractions gave the title compound as a crystalline solid (1.8 g), mp. 76°–78°.

Anal. Calc'd. for $C_{19}H_{30}ClN_3O_4$: C, 57.06; H, 7.56; N, 10.51; Cl, 8.87. Found: C, 56.65; H, 7.69; N, 10.46; Cl, 8.53.

EXAMPLE 19

4-Amino-5-chloro-N-[2-(diethylamino)ethyl]-2-(3-methylisoxazol-5-yl)methoxybenzamide A solution of the tetrabutylammonium salt of 4-amino-5-chloro-N-[2-(diethylamino)ethyl]-2-hydroxybenzamide (4.82 g, 9.14 mmoles) in 50 ml acetonitrile was treated with 5-bromomethyl-3-methylisoxazole and stirred for 1.5 hours. The crystalline product was collected and dried (2.53 g). A second crop was obtained by concentration of the filtrate and crystallization of the residue from ethyl acetate (0.51 g, 87% yield). The analytical sample was recrystallized from ethyl acetate, mp. 109°–111°.

Anal. Calc'd. for $C_{18}H_{25}ClN_4O_3$: C, 56.76; H, 6.62; N, 14.71; Cl, 9.31. Found: C, 56.78; H, 6.90; N, 14.97; Cl, 9.40.

EXAMPLE 20

4-Amino-5-chloro-N-[2-(diethylamino)ethyl]-2-[2-(methylthio)ethoxy]benzamide

A stirred mixture of 4-amino-5-chloro-N-[2-(diethylamino)ethyl]-2-hydroxybenzamide hydrochloride (10.0 g, 31.06 mmoles) (from Preparation No. 1A), anhydrous potassium carbonate (12.84 g, 93.16 mmoles), sodium iodide (4.66 g, 31.06 mmoles) and 2-chloroethyl methyl sulfide (3.70 ml, 4.10 g, 37.26 mmoles) in 60 ml dry DMF was refluxed for 10 hours. The solvent was evaporated under reduced pressure and the dark semi-solid was partitioned between water and methylene chloride. Sodium hydroxide solution was added to bring the pH of the aqueous layer to 14. The mixture was shaken well and the layers were separated. The aqueous layer was extracted with 3 portions of methylene chloride. The combined organic solutions were dried over $MgSO_4$ and evaporated. The solid obtained was dissolved in 100 ml of warm acetonitrile. The solution was treated with Darco G-60, filtered, evaporated to 30 ml, and stored at −15°. The solid was filtered to give 3.56 g (32%) of the title compound as off-white crystals, mp. 118°–120°.

Anal. Calc'd. for $C_{16}H_{26}ClN_3O_2S$: C, 53.39; H, 7.28; N, 11.67; Cl, 9.85; S, 8.91. Found: C, 53.60; H, 7.39; N, 11.69; Cl, 9.47; S, 9.43.

EXAMPLE 21

4-Amino-5-chloro-N-[2-(diethylamino)ethyl]-2-[2-(methylsulfinyl)ethoxy]benzamide To a stirred solution of 4-amino-5-chloro-N-[2-(diethylamino)ethyl]-2-[2-(methylthio)ethoxy]benzamide (1.0 g, 2.28 mmoles) (prepared in Example 20) and 1.4N HCl solution (3.97 ml, 5.56 mmoles) in 15 ml of $H_2O$ at 0°–5°, was added sodium metaperiodate (0.625 g, 2.92 mmoles). The mixture, which soon began to darken, was stirred at 0°–5° to 2 hours. The mixture was then diluted to 50 ml and made alkaline (pH=12) with NaOH solution. Methylene chloride (50 ml) was added, the mixture was shaken well, and the layers were separated. The aqueous layer was extracted with 3 portions of methylene chloride and the combined organic solutions were dried (anhydrous $MgSO_4$) and evaporated. A dark oil (0.96 g) which solidified upon standing was obtained. The crude product was flash chromatographed on silica, eluting with $CH_2Cl_2:CH_3OH:NH_4OH$, 80:20:0.5. Appropriate fractions were combined and evaporated to give 0.80 g (77%) of the title compound as a yellow resin which crystallized upon standing, mp. 110°–114°.

Anal. Calc'd. for $C_{16}H_{26}ClN_3O_3S$: C, 51.12; H, 6.97; N, 11.18; Cl, 9.43; S, 8.53. Found: C, 50.42; H, 6.94; N, 10.91; Cl, 9.94; S, 8.30.

EXAMPLE 22

4-Amino-2-(2-butanon-3-yl)oxy-5-chloro-N-[2-(diethylamino)ethyl]benzamide hydrochloride A solution of the tetra-n-butylammonium salt of 4-amino-5-chloro-N-[2-(diethylamino)ethyl]-2-hydroxybenzamide (0.53 g, 1.0 mmole) in acetonitrile (6 ml) was treated with 3-chloro-2-butanone (0.11 ml, 0.12 g, 1.1 mmole) and stirred at 20° for 16 hours. After removal of the acetonitrile at reduced pressure, the residue was treated with 10 ml water and extracted with ethyl acetate. The extracts were washed with dilute sodium carbonate, dried and concentrated to leave an oil which was converted to a monohydrochloride salt with 1.0 ml 1N hydrochloric acid. Crystallization of this salt from 2-propanol-ethyl acetate gave the title compound, mp. 176°–179°. This material was identical to that prepared in Example 7C.

EXAMPLE 23

(A)

4-Amino-5-chloro-2-(cyclohexanon-2-yl)oxy-N-[2-(diethylamino)ethyl]benzamide

A mixture of 4-amino-5-chloro-N-[2-(diethylamino)ethyl]-2-hydroxybenzamide hydrochloride (15 g, 47 mmoles) (from Preparation 1A), tetrabutylammonium bromide (15 g, 47 mmoles), anhydrous potassium carbonate (34.32 g, 0.234 mole), 2-chlorocyclohexanone (8.9 g, 67 mmoles) in DMF (60 ml) was stirred for 4 days. The reaction mixture was partitioned between water and ethyl acetate. The ethyl acetate solution was washed with 0.4N NaOH, water and extracted with 1N HCl (50 ml). The acid extract was basified with saturated sodium carbonate solution and extracted with methylene chloride. The extract was dried and filtered through silica, the filtrate was concentrated and the concentrate diluted with pentane. The oiled-out material solidified on standing and was crystallized from toluene (30 ml) to yield the title compound, mp. 96°–99°.

Anal. Calc'd. for $C_{19}H_{28}ClN_3O_3$: C, 59.75; H, 7.39; N, 11.00; Cl, 9.29. Found: C, 59.65; H, 7.34; N, 10.68; Cl, 9.03.

(B)

4-Amino-5-chloro-2-(cyclohexanon-2-yl)oxy-N-[2-(diethylamino)ethyl]benzamide sulfate The 4-amino-5-chloro-2-(cyclohexanon-2-yl)oxy-N-[2-(diethylamino)ethyl]benzamide (190 mg, 0.5 mmole) was dissolved in 25 ml 2-propanol and treated with 1 ml of 1N sulfuric acid. The solution was concentrated under reduced pressure upon which crystallization occurred to yield the title compound, mp. 175° dec.

Anal. Calc'd. for $C_{19}H_{30}ClN_3O_3S$: C, 47.54 H, 6.30; N, 8.75; Cl, 7,39; S, 6.68. Found: C, 47.52; H, 6.39; N, 8.46; Cl, 7.26; S, 6.80.

(C)

4-Amino-5-chloro-2-(cyclohexanon-2-yl)oxy-N-[2-(diethylamino)ethyl]benzamide hydrochloride was prepared, using 1N hydrochloric acid, in the same manner as the sulfate, mp. 150°–153° dec.

Anal. Calc'd. for $C_{19}H_{29}Cl_2N_3O_3$: C, 54.54; H, 6.99; N, 10.04. Found: C, 54.54; H, 7.03; N, 9.95.

EXAMPLE 24

4-Amino-5-chloro-N-[2-(diethylamino)ethyl]-2-(5-hexan-2-on-3-yl)oxybenzamide hydrochloride To a stirred suspension of sodium hydride (400 mg of 60%, 10 mmole, washed with n-pentane) in DMF (10 ml) was added 4-amino-5-chloro-N-[2-(diethylamino)ethyl]-2-(2-propanon-1-yl)oxybenzamide (3.4 g, 10 mmoles) (prepared in Example 5) under nitrogen. The mixture was stirred until evolution of hydrogen subsided. Allyl bromide (0.9 ml, 1.26 g, 10.5 mmoles) was added and stirring continued for 18 hours. The mixture was partitioned between water and methylene chloride and the organic phase washed with water, dried, concentrated and the residue chromatographed on deactivated silica using methylene chloride (100), methanol (4), ammonia (0.5) solvent system. The appropriate fractions were combined to give 1.14 g of free base. This was dissolved in 1-propanol and treated with 7 ml 2N HCl followed by concentration to give an oily residue. This was crystallized from acetone-ether and the product recrystallized from 2-propanol to give 0.53 g of the title compound, mp. 171°–173°. The NMR spectrum (90 MHz) in $D_2O$ gave the following resonances: δ 7.88 (s, 1H); 6.42 (s, 1H); 6.12–4.88 (m, 3H); 3.76 (bd, 2H); 3.28 (m, 6H); 2.88 (bt, 2H); 2.4 (s, 3H); 1.35 (t, 6H).

Anal. Calc'd. for $C_{19}H_{29}Cl_2N_3O_3$: C, 54.55; H, 6.99; N, 10.04; Cl, 16.95. Found: C, 54.22; H, 7.11; N, 9.90; Cl, 16.51.

EXAMPLE 25

4-Amino-5-chloro-N-[2-(diethylamino)ethyl]-2-(pentan-2-on-3-yl)oxybenzamide

A solution of the tetrabutylammonium salt of 4-amino-5-chloro-N-[2-(diethylamino)ethyl]-2-hydroxybenzamide (10.5 g, 20 mmoles) (from Prepration No. 3) in acetonitrile (150 ml) was treated with 3-bromo-2-pentanone (3.3 g of 80%, 20 mmoles, contaminated with 15% of 1-bromo-2-pentanone) [obtained according to the procedure of E. T. Borrows, D. O. Holland and J. Kenyon, *J. Chem. Soc.* 1083, (1946)]. After 3 hours, the solvent was evaporated and the residue partitioned between ethyl acetate and water. The organic phase was washed with water, dried, and the solvent evaporated. The semisolid residue was triturated with ether to yield a solid which was recrystallized from ether—petroleum ether to yield 1.5 g of the title compound, mp. 75°–78°. The NMR spectrum (90 MHz) in $CDCl_3$ gave the following resonances: δ 8.26 (s, 1H); 8.14 (bs, 1H); 6.1 (s, 1H); 4.5 (t, 1H); 4.4 (s, 2H); 3.69 (q, 2H); 2.64 (m, 6H); 2.1 (s, 3H); 2.1–1.7 (m, 2H); 1.05 (m, 9H).

Anal. Calc'd. for $C_{18}H_{28}ClN_3O_3$: C, 58.45; H, 7.63; N, 11.36; Cl, 9.59. Found: C, 58.30; H, 7.61; N, 11.20; Cl, 9.20.

EXAMPLE 26

4-Amino-2-(2-butanon-1-yl)oxy-5-chloro-N-[2-(diethylamino)-ethyl]benzamide

A solution of the tetrabutylammonium salt of 4-amino-5-chloro-N-[2-(diethylamino)ethyl]-2-hydroxybenzamide (5.3 g, 10 mmoles) in acetonitrile (100 ml) was treated with 1-bromo-2-butanone (1.5 g, 10 mmoles) and stirred at 20° for 2 hours. The residue after concentration was treated with water and extracted with ethyl acetate and methylene chloride-2-propanol (5:1). The insoluble solid material was collected and combined with the organic extracts. Concentration of this mixture gave sticky crystalline material which was recrystallized from acetonitrile-water (4:1) to give the title product (3.1 g, 86%), mp, 103.0–104.5°.

Anal. Calc'd. for $C_{17}H_{26}ClN_3O_3$: C, 57.37; H, 7.37; N, 11.81; Cl, 9.96. Found: C, 57.21; H, 7.34; N, 11.76; Cl, 9.67.

EXAMPLE 27

4-Amino-5-chloro-N-[2-(diethylamino)ethyl]-2-(pentan-2-on-1-yl)oxybenzamide

A solution of the tetrabutylammonium salt of 4-amino-5-chloro-N-[2-(diethylamino)ethyl]-2-hydroxybenzamide (10.54 g, 20 mmoles) in acetonitrile (150 ml) was treated with 1-bromo-2-pentanone [3.3 g of 45% purity; obtained as a by-product in the bromination of 2-pentanone according to the procedure of E. T. Borrows, D. O. Holland and J. Kenyon, *J. Chem. Soc.* 1083 (1946) and identified by NMR], and left to stir for 16 hours. After evaporation of the solvent, the residue was partitioned between water and ethyl acetate. The organic phase was washed with water, dried, and the solvent evaporated. The residue was chromatographed over deactivated silica using methylene chloride (100), methanol (2), ammonia (0.5) solvent system. The appropriate fractions were combined to give a solid which was recrystallized from ethyl acetate to give 0.8 g of the title compound, mp. 112°–115°. The NMR spectrum (90 MHz) in $CDCl_3$ gave the following resonances: δ 8.48

(bt, 1H); 8.24 (s, 1H); 6.14 (s, 1H); 4.7 (s, 2H); 4.4 (s, 2H); 3.56 (q, 2H); 2.66 (m, 8H); 1.7 (m, 2H); 1.06 (t, 9H).

Anal. Calc'd. for $C_{18}H_{28}ClN_3O_3$: C, 58.45; H, 7.63; N, 11.36. Found: C, 58.16; H, 7.66; N, 11.28.

EXAMPLE 28

4-Amino-5-chloro-2-(pentan-3-on-2-yl)oxy-N-(2-diethylaminoethyl)benzamide hydrochloride A mixture of 4-amino-5-chloro-N-[2-(diethylamino)ethyl]-2-hydroxybenzamide hydrochloride (4.83 g, 0.015 mmole) (from Preparation No. 1A), 2-bromo-3-pentanone (2.72 g, 0.0165 mmole) [prepared according to J. M. McIntosh and G. M. Masse, *J. Org. Chem.*, 40, 1294 (1975)] and potassium carbonate (4.14 g; 0.030 mmole) in 80 ml of dry DMF was stirred and heated at 90°–95° for 2 hours. The mixture was filtered and the DMF was removed under vacuum. The oily residue was redissolved in methylene chloride, washed sequentially with water, aqueous 1.0N NaOH and water and dried over $Na_2SO_4$. After evaporation of the solvent the crude oil was purified by flash chromatography on 86 g of silica gel (230–400 mesh) using a gradient elution of methanol-methylene chloride containing 0.25% $NH_4OH$. The appropriate fractions were combined and evaporated to yield 4.31 g (77.7%) of light yellow gum.

The free base (4.30 g; 0.0116 mmole) was dissolved in 75 ml of isopropyl alcohol, 2.90 ml of aqueous 4.0N HCl was added, and the solution was concentrated to ca. 30 ml to give, after cooling, filtration and drying in vacuo 3.85 g (63.2%) of the crude product. This was recrystallized from acetonitrile to give the title compound as a white solid, mp. 100°–112°.

Anal. Calc'd. for $C_{18}H_{28}ClN_3O_3$ HCl: C, 53.20; H, 7.19; N, 10.34; Cl, 17.45. Found: C, 53.24; H, 7.17; N, 10.26; Cl, 17.47.

EXAMPLE 29

4-Amino-5-chloro-N-[2-(diethylamino)ethyl]-2-[(3-methyl)-butan-2-on-1-yl]oxybenzamide A mixture of 4-amino-5-chloro-N-[2-(diethylamino)ethyl]-2-hydroxybenzamide hydrochloride (5.82 g, 18 mmoles), anhydrous potassium carbonate (12.48 g; 90 mmoles) in DMF (30 ml) and 1-bromo-3-methyl-2-butanone [4.5 g, 27 mmoles; prepared according to M. Gaudry and A. Marquet, *Org. Syn.* 55, 24 (1976)] was stirred for 20 hours under nitrogen. The mixture was poured into water (150 ml) and the solid collected, dried and crystallized from toluene to give the title compound (4.86 g, 73%), mp. 109°–110°. The NMR spectrum (90 MHz) gave the following resonances: δ 8.56 (bt, 1H); 8.24 (s, 1H); 6.18 (s, 1H); 4.8 (s, 2H); 4.44 (s, 2H) 3.56 (m, 2H); 2.62 (m, 7H); 1.2 (d, 6H); 1.06 (t, 6H).

Anal. Calc'd. for $C_{18}H_{28}ClN_3O_3$: C, 58.45; H, 7.63; N, 11.36. Found: C, 58.38; H, 7.63; N, 11.25.

EXAMPLE 30

4-Amino-5-chloro-N-[2-(diethylamino)ethyl]-2-(3-phenyl-2-propanon-1-yl)oxybenzamide A solution of the tetrabutylammonium salt of 4-amino-5-chloro-N-[2-(diethylamino)ethyl]-2-hydroxybenzamide (3.45 g, 6.5 mmoles) and 1-chloro-3-phenyl-2-propanone (1.1 g, 6.5 mmoles) in acetonitrile was stirred for 18 hours at 20°. After removal of the acetonitrile at reduced pressure, the residue was treated with water and extracted with methylene chloride. The residue, after concentration of the extracts, was chromatographed on alumina (grade III) using ethyl acetate from elution. Combination of the appropriate fractions gave 1.1 g of product which was recrystallized from ethyl acetate to give the title compound, mp. 138°–139°.

Anal. Calc'd. for $C_{22}H_{28}ClN_3O_3$: C, 63.22; H, 6.71; N, 10.05; Cl, 8.48. Found: C, 63.23; H, 6.71; N, 9.92; Cl, 8.28.

EXAMPLE 31

4-Amino-5-chloro-N-[2-(diethylamino)ethyl]-2-[(3-methyl)butan-2-on-3-yl]oxybenzamide monohydrate A solution of the tetrabutylammonium salt of 4-amino-5-chloro-N-[2-(diethylamino)ethyl]-2-hydroxybenzamide (15.81 g, 30 mmoles) in DMF was treated with 3-bromo-3-methyl-2-butanone [4.95 g, 30 mmoles, (80% pure), prepared according to M. Gaudry and A. Marquet, *Tetrahedron* 26, 5611 (1970)]. After stirring for 20 hours, the solvent was evaporated and the residue was partitioned between ethyl acetate and water. The ethyl acetate layer was washed with 0.4N NaOH, $H_2O$, dried and the solvent evaporated. The residue was chromatographed over deactivated silica using methylene chloride (100), methanol (2), ammonia (0.5) solvent system. The appropriate fractions were combined to give 4.86 g of an oil. A portion of this (3.86 g) was crystallized from acetonitrile-water and recrystallized from methanol-water to give 1.23 g of title compound, mp. 84°–88°. The NMR spectrum (90 MHz) in $CDCl_3$ gave the following resonances: δ 8.24 (s, 1H); 8.08 (bs, 1H); 5.92 (s, 1H); 4.34 (s, 2H); 3.58 (q, 2H); 2.6 (q, 6H); 2.32 (s, 3H); 1.66 (s, 2H); 1.64 (s, 6H); 1.04 (t, 6H).

Anal. Calc'd. for $C_{18}H_{28}ClN_3O_3 \cdot H_2O$: C, 55.73; H, 7.80; N, 10.83; Cl, 9.14; $H_2O$, 4.67. Found: C, 55.75; H, 7.83; N, 10.72; Cl, 8.74; $H_2O$, 4.62.

EXAMPLE 32

4-Amino-2-(2-butanon-3-yl)oxy-5-chloro-N-[2-(dimethylamino)ethyl]benzamide

A solution of 4-amino-5-chloro-N-[2-(dimethylamino)ethyl]-2-hydroxybenzamide (1.90 g, 7.37 mmole) (prepared in Example 17), potassium carbonate (3.06 g, 2.21 mmoles), sodium iodide (1.11 g, 7.37 mmoles) and 91% 3-bromo-2-butanone (1.81 g, 12 mmoles) in DMF (30 ml) was stirred for 1.5 hours. The solvent was removed in vacuo and the residue partitioned between water and methylene chloride. The aqueous phase was extracted two more times with methylene chloride. The combined extracts were dried and concentrated in vacuo. The residue was chromatographed on a silica gel column using the solvent system of methylene chloride (99.5)-methanol (0.5)-ammonia (0.2). The appropriate fractions were combined and concentrated in vacuo to give a solid. This was recrystallized from acetonitrile to give 1.85 g of the title compound as a colorless solid, mp. 124°–125°.

Anal. Calc'd. for $C_{15}H_{22}ClN_3O_3$: C, 54.96; H, 6.76; N, 12.82; Cl, 10.82. Found: C, 55.17; H, 6.86; N, 12.80; Cl, 10.83.

EXAMPLE 33

4-Amino-5-chloro-N-[2-(diethylamino)ethyl]-2-[2-(2-hydroxy-3-phenylpropyl)]oxybenzamide A solution of the tetrabutylammonium salt of 4-amino-5-chloro-N-[2-(diethylamino)ethyl]-2-hydroxybenzamide (2.64 g, 5 mmoles) and 1-chloro-2-hydroxy-3-phenylpropane (0.85 g, 5 mmoles) in 10 ml of DMF was heated at reflux for 2 hours. The mixture was concentrated at reduced pressure. The residue was taken up in methylene chloride, washed with dilute sodium hydroxide, dried over $Na_2SO_4$ and concentrated. The product was recrystallized from ethyl acetate to give the title compound (1.05 g), mp. 155°–157°.

Anal. Calc'd. for $C_{22}H_{30}ClN_3O_3$: C, 62.92; H, 7.20; N, 10.01; Cl, 8.44. Found: C, 62.71; H, 7.26; N, 10.01; Cl, 8.27.

EXAMPLE 34

4-Amino-5-chloro-N-[2-(diethylamino)ethyl]-2-(2-hydroxyiminobut-3-yl)oxybenzamide A solution of 4-amino-2-(2-butanon-3-yl)oxy-5-chloro-N-[2-diethylamino)ethyl]benzamide hydrochloride (1.14 g, 2.9 mmoles) (prepared in Example 7C) and hydroxylamine hydrochloride (0.3 g, 4.3 mmoles) in methanol (20 ml) was refluxed for 15 minutes. The solvent was evaporated and the residue was partitioned between methylene chloride and a saturated solution of sodium carbonate. The organic phase was washed with water, dried and the solvent evaporated. The residue was crystallized from ethyl acetate and petroleum ether to yield the title compound, mp. 113°–115° (0.37 g). The NMR spectrum (90 MHz) in $CDCl_3$ gave the following resonances: δ 9.8 (bs, 1H); 8.16 (s, 1H); 6.4 (s, 1H); 4.96 (q, 1H); 4.4 (s, 2H); 4.02–3.08 (bm, 3H); 2.66 (m, 6H); 1.84 (s, 3H); 1.6 (d, 3H); 1.08 (t, 6H).

Anal. Calc'd. for $C_{17}H_{27}ClN_4O_3$: C, 55.05; H, 7.34; N, 15.11; Cl, 9.56. Found: C, 54.91; H, 7.34; N, 14.97; Cl, 9.45.

EXAMPLE 35

α-{3-Amino-4-chloro-6-[N-(2-[diethylamino]ethyl)]carbomoylphenoxy}phenylacetic acid, ethyl ester To a well-stirred suspension of sodium hydride (0.36 g of 60%, 9 mmoles, washed with n-pentane) in 5 ml of dry DMF was added a solution of 4-amino-5-chloro-N-[2-(diethylamino)ethyl]-2-hydroxybenzamide (2.28 g, 8 mmoles) (from Preparation No. 1B) in 10 ml of dry DMF. After evolution of hydrogen had ceased, to this was added dropwise a solution of ethyl α-bromophenyl acetate (2.12 g, 8.7 mmoles) in 5 ml of dry DMF. After an additional 18 hours at ambient temperature, the mixture was concentrated in vacuo and the residue partitioned between water (200 ml) and methylene chloride (75 ml). The aqueous phase was extracted twice with 75 ml portions of methylene chloride. After combining, the organic phase was washed three time with 50 ml of 10% aqueous sodium hydroxide and three time with brine; dried over sodium sulfate, filtered, concentrated in vacuo, to give 3.5 g of oil which slowly crystallized. Trituration with pentane gave 3.34 g of the title compound, mp. 84°–87° C. The NMR spectrum (90 MHz) in $CDCl_3$ gave the following resonances: δ 8.55 (bt, 1H); 8.20 (s, 1H); 7.50 (m, 5H); 6.09 (s, 1H); 5.65 (s, 1H); 4.25 (m, 4H); 3.55 (m, 2H); 2.60 (m, 6H); 1.05 (m, 9H).

Anal. Calc'd. for $C_{23}H_{30}ClN_3O_4$: C, 61.66; H, 6.76; N, 9.38. Found: C, 61.75; H, 6.76; N, 9.27.

EXAMPLE 36

4-Amino-5-chloro-N-[2-(diethylamino)ethyl]-2-(2-hydrazino-2-oxoethoxy)benzamide Trihydrate A suspension of 4-amino-5-chloro-N-[2-(diethylamino)ethyl]-2-(2-methoxy-2-oxoethoxy)benzamide (3.58 g, 10 mmoles) (prepared in Example 15) in 64% hydrazine hydrate in water (0.6 g, 12 mmoles) and methanol (3 ml) was stirred for 1 hour, when a clear solution was formed. The mixture was concentrated in vacuo and the residue recrystallized from water, to give, after drying, 3.65 g (88.6%) of the title compound as the trihydrate, mp. 130°–131° C.

Anal. Calc'd. for $C_{15}H_{24}N_5ClO_3.3H_2O$: C, 43.73; H, 7.34; N, 17.00; Cl, 8.60; $H_2O$, 13.12. Found: C, 44.07; H, 7.46; N, 17.19; Cl, 8.77; $H_2O$, 11.60.

EXAMPLE 37

4-Amino-5-chloro-N-[2-(diethylamino)ethyl]-2-[2-(2-acetylhydrazino)-2-oxoethoxy]benzamide Acetate 4-Amino-5-chloro-N-[2-(diethylamino)ethyl]-2-(2-hydrazino-2-oxoethoxy)benzamide trihydrate (1.0 g, 2.43 mmoles) (prepared in Example 36) was dried at 110° C./0.02 mm for 3 hours to give the corresponding anhydrous material (865 mg). This was treated with a solution of acetic anhydride (248 mg, 2.428 mmoles) in methylene chloride (5 ml) until clear solution was formed. The solution was concentrated in vacuo to give 1.115 g (100%) of the title compound as white hygroscopic solid.

Anal. Calc'd. for $C_{19}H_{30}N_5ClO_6$: C, 49.62; H, 6.58; N, 15.23; Cl, 7.71. Found: C, 48.86; H, 6.67; N, 14.87; Cl, 8.20.

EXAMPLE 38

4-Amino-5-chloro-N-[2-(diethylamino)ethyl]-2-[3-(phthalimido)propoxy]benzamide

To a suspension of the tetra-n-butylammonium salt of 4-amino-5-chloro-N-[2-(diethylamino)ethyl]-2-hydroxybenzamide (15.8 g, 30 mmoles) (prepared in Preparation 3) in acetonitrile (50 ml) was added N-(3-bromopropyl)phthalimide and the mixture stirred for 16 hours at ambient temperature and 1 hour at 65°–70° C. This was concentrated in vacuo and the residue partitioned between water and a 1:1 mixture of ether and methylene chloride. The orgnic phase was washed several times with water, dried and concentrated to small volume causing crystallization. This was filtered and the solid washed with ether to give 12.3 g (86.7%) of the title product was white solid, mp. 141°–143°.

Anal. Calc'd. for $C_{24}H_{29}N_4ClO_4$: C, 60.94; H, 6.18; N, 11.85; Cl, 7.5. Found: C, 61.05; H, 6.43; N, 11.80; Cl, 7.63.

EXAMPLE 39

4-Amino-2-(3-aminopropoxy)-5-chloro-N-[2-(diethylamino)ethyl]benzamide

A mixture of 4-amino-5-chloro-N-[2-(diethylamino)ethyl]-2-[3-(phthalimide)propoxy]benzamide (4.73 g, 10 mmoles) (prepared in Example 38), 64% hydrazine hydrate (800 mg, 16 mmoles) and absolute ethanol (15 ml) was heated briefly to reflux until clear solution was formed. The solution was heated 16 hours at 55°–57° C. and then 2 hours at reflux. After cooling, a solid was filtered off and washed with ethanol. The combined filtrate and washings were concentrated in vacuo. The residue was dissolved in methylene chloride, and insoluble solid removed by filtration. The filtrate was washed with water, dried and concentrated in vacuo to give a solid product. This was recrystallized from methylene chloride-n-pentane to give 2.96 g (86.3%) of the title compound as white solid, mp 119°–121° C.

Anal. Calc'd. for $C_{16}H_{27}N_4ClO_2$: C, 56.05; H, 7.94; N, 16.34; Cl, 10.34. Found: C, 56.05; H, 7.92; N, 16.10; Cl, 10.47.

EXAMPLE 40

4-Amino-5-chloro-N-[2-(diethylamino)ethyl]-2-[2-methylamino)-2-oxoethoxy]benzamide To a suspension of 4amino-5-chloro-N-[2-(diethylamino)ethyl]-2-(2-methoxy-2-oxoethoxy)benzamide (1.074 g, 3 mmoles) (prepared in Example 15), in a 1N solution of methylamine in toluene (10 ml) was added 3 ml of methanol and the mixture stirred for 16 hours. This was concentrated in vacuo and the residue crystallized from methanol-ether to give 815 mg (76%) of the title compound as white solid; mp. 149°–151° C.

Anal. Calc'd for $C_{16}H_{25}N_4ClO_3$: C, 53.85; H, 7.06; N, 15.70; Cl, 9.94. Found: C, 53.85; H, 7.16; N, 15.63; Cl, 10.00.

EXAMPLE 41

4-Amino-5-chloro-N-[2-(diethylamino)ethyl]-2-[(2-hydroxy)but-3-yl]oxybenzamide (mixture of threo and erythro isomers)

A mixture of 4-amino-2-(2-butanon-3-yl)oxy-5-chloro-N-[2-(diethylamino)ethyl]benzamide (obtained by treating 1.2 g, 3.1 mmole, of the corresponding hydrochloride salt, prepared in Example 7C, with saturated sodium carbonate solution) and sodium borohydride (100 mg) in ethanol (20 ml) was heated under reflux for one hour. The solution was concentrated, diluted with water, acidified with 2N hydrochloride acid, and basified with saturated sodium carbonate solution. The mixture was extracted with methylene chloride to yield 1.16 g of foam. This material was chromatographed over deactivated silica using methylene chloride (100), methanol (2), ammonia (0.5) as the solvent system. The appropriate fractions were combined to yield the title compound (470 mg) as a foamy mixture of diastereoisomers. The NMR spectrum (90 MHz) in CDCl$_3$ gave the following resonances: δ 8.54 (bd, 1H); 8.2, 8.15 (2s, 1H); 6.32, 6.35 (2s, 1H); 4.36 (s, 2H); 4.24–4 (m, 1H); 4–2.12 (m, 3H); 2.8–2.52 (m, 6H); 1.41–0.96 (m, 12H).

Anal. Calc'd. for $C_{17}H_{28}ClN_3O_3$: C, 57.05; H, 7.89; N, 11.74; Cl, 9.91. Found: C, 56.34; H, 7.79; N, 11.55; Cl, 9.65.

EXAMPLE 42

4-Amino-5-chloro-N-[2-(diethylamino)ethyl]-2-(ethyl-3-methoxycroton-4-yl)oxybenzamide The general procedure of Example 35 was repeated except that the ethyl α-bromophenylacetate utilized therein was replaced by an equimolar amount of ethyl 3-methoxy-4-chlorocarbonate (prepared according to U.S. Pat. No. 4,348,333). The solvent (DMF) was removed in vacuo, the residue treated with water and methylene chloride. The latter was washed with 10% sodium hydroxide, water and brine followed by drying over sodium sulfate, filtration and concentration. The crude solid was recrystallized from ether/methylene chloride giving the title compound, mp. 109°–111° C.

Anal. Calc'd. for $C_{20}H_{30}ClN_3O_5$: C, 55.99; H, 7.06; N, 9.80. Found: C, 55.96; H, 7.14; N, 9.77.

EXAMPLE 43

4-Amino-5-chloro-N-[2-(diethylamino)ethyl]-2-(1,3-dioxolan-2yl)oxybenzamide

The general procedure of Example 35 was repeated except that the ethyl α-bromophenylacetate utilized therein was replaced by an equimolar amount of 2-bromoethyl-1,3-dioxalane and the reaction mixture heated to 80° C. for 30.5 hours. The solvent (DMF) as removed in vacuo, the residue treated with brine and methylene chloride; the latter washed with 10% sodium hydroxide and brine, dried over sodium sulfate, filtered and concentrated. Recrystallization from methylene chloride/hexane provided the title compound, mp. 93°–95° C.

Anal. Calc'd. for $C_{17}H_{26}ClN_3O_4$: C, 54.90; H, 7.06; N, 11.30. Found: C, 54.98; H, 7.07; N, 11.40.

EXAMPLE 44

4-Amino-5-chloro-N[2-(diethylamino)ethyl]-2-(oxazolidin)-2-one-5-ylmethyl)oxybenzamide Fumarate Equimolar amounts (6 mmoles) of the tetra-n-butylammonium salt of 4-amino-5-chloro-N-[2-(diethylamino)ethyl]-2-hydroxybenzamide (prepared in Preparation 3) and 5-chloromethyl-2-oxazolidinone in 15 ml DMF were heated at reflux with stirring for 3 hours. After removal of the solvent the residue was dissolved in methylene chloride and washed with water. After drying over MgSO$_4$ and concentration, 2.7 g of crude product was obtained. This material was purified by chromatography on alumina grade III using ethyl acetate containing 5 and 10% ethanol as eluant. The partially purified product (1.1 g) in 1-propanol was treated with fumaric acid (0.33 g) to give 0.81 g (30.5%) of the crystalline fumarate salt, mp. 165°–167° C.

Anal. Calc'd. for $[C_{17}H_{25}ClN_4O_4]_2 \cdot C_4H_{O4}$: C, 51.52; H, 6.15; N, 12.65; Cl, 8.01. Found: C, 51.21; H, 6.18; N, 12.40; Cl, 7.99.

EXAMPLE 45

4-Amino-5-chloro-N-[2-(diethylamino)ethyl]-2-(2-pyridinomethyl)oxybenzamide

To a solution of the tetra-n-butylammonium salt of 4-amino-5-chloro-N-[2-(diethylamino)ethyl]-2-hydroxybenzamide (2.64 g, 0.005 mole) prepared in Preparation 3) in 30 ml acetonitrile was added 2-chloromethylpyridine (prepared by K$_2$CO$_3$ neutralization of 0.01 mole of the corresponding hydrochloride). The resultant reaction mixture was stirred for 18 hours and then concentrated. The residue was chromatographed on alumina grade III using ethyl acetate and ethyl acetate, ethanol (100:2) as eluants to give 1.8 g of purified product which was recrystallized from 2:1 ethyl acetate-n-hexane. There was obtained 1.45 g (77%) of the title compound, mp. 84°–85° C.

Anal. Calc'd. for $C_{19}H_{25}ClN_4O_2$: C, 60.55; H, 6.69; N, 14.87; Cl, 9.41. Found: C, 60.62; H, 6.76; N, 14.81; Cl, 9.34.

EXAMPLE 46

4-Amino-5-chloro-N-[2-(diethylamino)ethyl]-2-(2-methoxyethoxyethyl)oxybenzamide

The general procedure of Example 35 was repeated except that the ethyl α-bromophenylacetate utilized therein was replaced by an equimolar amount of 1-bromo-2-(2-methoxyethoxy)ethane. The solvent (DMF) was removed in vacuo, the residue treated with brine and methylene chloride; the latter washed with 10% sodium hydroxide and brine, dried over sodium sulfate, filtered and concentrated. Recrystallization from ether provided the title compound, mp. 49°–51° C.

Anal. Calc'd. for $C_{18}H_{30}ClN_3O_4$: C, 55.72; H, 7.81; N, 10.83. Found: C, 55.50; H, 7.69; N, 10.78.

EXAMPLE 47

4-Amino-2-(2-aminoethoxy)-5-chloro-N-[2-(diethylamino)ethyl]benzamide

To a suspension of one teaspoonful of Raney nickel (well washed with methanol) in methanol (130 ml) was added 4-amino-5-chloro-2-cyanomethyl-N-[2-(dimethylamino)ethyl]benzamide (12.05 g, 37.1 mmoles) (prepared in Example 13), and the mixture hydrogenated at 40 psi for 5 hours. The catalyst was removed by filtration under nitrogen and the filtrate concentrated in vacuo. This was dissolved in methylene chloride and washed with 1N sodium hydroxide (4×25 ml). The washings were back extracted with methylene chloride and the organic phases combined, dried and concentrated in vacuo to give 5.56 g of the title product as a semi-solid. This was recrystallized from methanol-ether in the cold to give a sample, mp. 97°–99° C.

Anal. Calc'd. for $C_{15}H_{25}ClN_4O_2$: C, 54.78; H, 7.60; Cl, 10.78; N, 17.04. Found: C, 54.71; H, 7.64; Cl, 10.91; N, 16.81.

EXAMPLE 48

2-(2-Acetylaminoethoxy)-4-amino-5-chloro-N-[2-(dimethylamino)ethyl]benzamide

To a solution of 4-amino-2-(2-aminoethoxy)-5-chloro-N-[2-(diethylamino)ethyl]benzamide (780 mg, 2.4 mmoles) (prepared in Example 47) in methylene chloride was added acetic anhydride (245 mg, 2.4 mmoles) and the mixture stirred for 3 minutes. This was concentrated in vacuo and the residue was partitioned between methylene chloride and sodium bicarbonate solution. The organic phase was concentrated and the residue flash-chromatographed on silica using methylene chloride:methanol:ammonia (100:4:0.5) solvent system. The appropriate fractions were combined and concentrated in vacuo. The residue was recrystallized from methylene chloride-ether to give 445 mg of the title compound as a white solid, mp. 143°–145° C.

Anal. Calc'd. for $C_{17}H_{27}ClN_4O_3$: C, 55.05; H, 7.37; Cl, 9.56; N, 15.11. Found: C, 54.82; H, 7.28; Cl, 9.71; N, 14.54.

EXAMPLE 49

4-Amino-5-chloro-N-[2-(diethylamino)ethyl]-2-[3-(methylthio)propoxy]benzamide

To a solution of tetrabutylammonium salt of 4amino-5-chloro-N-[2-(diethylamino)ethyl-2-hydroxybenzamide (10.54 g, 20 mmoles) (prepared in Preparation No. 3) in DMF (100 ml) was added 1-bromo-3-chloropropane (3.268 g, 2.2 ml, 20.76 mmoles) and the mixture stirred for 2 hours at ambient temperature and another 30 minutes at 40° C. The mixture was cooled to 0° C. and poured over sodium hydride (1.0 g of 60% mineral oil dispersion, 25 mmoles, washed with n-pentane) under nitrogen. The mixture was stirred in the cold while methyl mercaptan gas was bubbled in until evolution of hydrogen ceased. The mixture was heated at 35°–40° C. for 2 hours, poured into water (700 ml) and after standing for 1 hour the resultant solid was isolated by suction to give after drying in air 7.06 g (94%) of crude product, mp. 58°–59° C. This was dissolved in methylene chloride and filtered over a short column packed with silica and alumina. The filtrate was concentrated and the residue crystallized from ether to give 4.95 g (66%) of the title compound as a white solid, mp. 79°–80° C.

Anal. Calc'd. for $C_{17}H_{28}ClN_3O_2S$: C, 54.61; H, 7.55; Cl, 9.48; N, 11.24; S, 8.56 Found: C, 54.56; H, 7.52; Cl, 9.38; N, 11.10; S, 8.23

EXAMPLE 50

4-Amino-5-chloro-N-[2-(diethylamino)ethyl]-2-[3-(methylsulfinyl)propoxy]benzamide To a stirred solution of product from Example 49 (1.496 g, 4 mmoles) in 2N hydrochloric acid (5.0 ml, 10 mmoles) and water (20 ml) was added sodium periodate (856 mg. 4.0 mmoles) and the mixture stirred for 2.5 hours. It was then basified with 4N sodium hydroxide (3 ml) and extracted with methylene chloride (3×30 ml). The extracted was concentrated in vacuo and the residue flash-chromatographed on deactivated silica column using methylene chloride:methanol:ammonia (100:3.5:0.5) solvent system. The appropriate fractions were combined and concentrated to give a yellow oil which crystallized from methylene chloride-ether to give 770 mg of the title product as a light yellow solid, mp. 116°–117° C.

Anal. Calc'd. for $C_{17}H_{28}ClN_3O_3S$: C, 52.37; H, 7.24; Cl, 9.09; N, 10.78; S, 8.21. Found: C, 52.31; H, 7.25; Cl, 8.70; N, 10.68; S, 7.88.

EXAMPLE 51

4-Amino-5-chloro-N-[2-(diethylamino)ethyl]-2-(1H-4,5-dihydroimidazol-2-yl)methoxybenzamide A mixture of 4amino-5-chloro-2-cyanomethoxy-N-[2(diethylamino)ethyl]benzamide (3.25 g, 10 mmoles) (prepared in Example 13) and 1,2-diaminoethane (0.6 g, 10 mmoles) in methanol (25 ml) was heated at reflux for 3 hours. The reaction mixture was concentrated to leave a crystalline residue which was recrystallized from ethyl acetate to give the title product (2.78 g, 76%), mp. 144°–145° C.

Anal. Calc'd. for $C_{17}H_{26}ClN_5O_2$: C, 55.50; H, 7.12; Cl, 9.64; N, 19.04 Found: C, 55.64; H, 7.21; Cl, 9.75; N, 18.94

EXAMPLE 52

4-Amino-5-chloro-N-[2-(diethylamino)ethyl]-2-(2-thienoylmethoxy)benzamide

A mixture of 2-thiophenecarboxylic acid (2.6 g, 20 mmoles), thionyl chloride (2.4 g, 20 mmoles) and toluene (15 ml) was heated at reflux for one hour. The residue was concentrated to leave an oil (2.8 g). A solution of this oil is diethyl ether (10 ml) was added to a solution of diazomethane (prepared from 8.1 g, 80 mmoles, of N-methyl-N-nitrosourea) in ether (200 ml). After stirring for 2 hours at 20° C., the reaction was treated with hydrogen chloride gas (excess) over a period of 20 minutes. After stirring for an additional ½ hour, the reaction mixture was concentrated to give chloroacetyl-2-thiophene as a dark oil (3.2 g). A portion of this dark oil (1.6 g) was taken up in acetonitrile (25 ml), treated with the tetra-n-butylammonium salt of 4-amino-5-chloro-N-[2-(diethylamino)ethyl]-2-hydroxybenzamide (2.6 g, 5 mmoles) (prepared in Preparation No. 3) and stirred for 18 hours. After concentration, the residue was purified by chromatography on alumina (grade III) using ethyl acetate containing 2% ethanol for elution, to give the title product, which was recrystallized from acetonitrile, mp. 135°–139° C.

Anal. Calc'd. for $C_{19}H_{24}ClN_3O_2S$: C, 55.67; H, 5.90; N, 10.25; S, 7.82. Found: C, 55.86; H, 5.91; N, 10.18; S, 7.54.

EXAMPLE 53

4-Amino-5-chloro-2-(2-chloroethoxy)-N-[2-(2-diethylamino)ethyl]benzamide

To a stirred solution of sodium salt of 4-amino-5-chloro-N-[2-(diethylamino)ethyl]-2-hydroxybenzamide prepared from the corresponding hydrochloride salt (5.0 g, 16 mmoles) (prepared in Preparation No. 1) and sodium hydride (1.3 g of 60%, 32.6 mmoles) in 15 ml DMF was added 2-chloroethyl-p-toluenesulfonate (3.64 g, 16 mmoles), and the mixture was stirred for 16 hours at ambient temperature and another 3 hours at 80°–90° C. The mixture was concentrated in vacuo and the residue partitioned between brine and methylene chloride. The organic phase was washed with aqueous sodium hydroxide, brine, water, dried and concentrated in vacuo. The residue was recrystallized from ether to give 2.02 g of the title compound, mp. 153°–154° C.

Anal. Calc'd. for $C_{15}H_{23}Cl_2N_3O_2$: C, 51.72; H, 6.67; N, 12.06. Found: C, 51.76; H, 6.64; N, 11.42.

EXAMPLE 54

4-Amino-5-chloro-N-[2-(diethylamino)ethyl]-2-[2-methyl-2-(1,3-dioxolan)-4yl]oxybenzamide To a well-stirred suspension of pentane-washed sodium hydride (1.26 g of 60%, 32 mmoles) in 3 ml of dry DMF was added 4-amino-5-chloro-N-[2-(diethylamino)ethyl]-2-hydroxybenzamide (8.57 g, 3 mmoles) in 12 ml DMF over 35 minutes. After stirring for one and one-half hours, 2-methyl-2-(2-iodoethyl)-1,3dioxolone (6.54 g, 27 mmole) (prepared according to *J. Org. Chem.*, 48, 5381-5382 (1983)] was added over 8 minutes followed by stirring for 24 hours. The mixture was then poured into 300 ml of brine followed by extraction with four 100 ml portions of methylene chloride. After combining, the organic phase was washed twice with 100 ml of 10% aqueous sodium hydroxide and brine; dried over sodium sulfate, and concentrated in vacuo to give 9.44 g of oil. A 5 g aliquot of this material was purified by flash chromatography on a silica gel column eluted with a solvent mixture composed of methylene chloride (93), methanol (7), ammonia (0.2). Appropriate fractions were combined, and concentrated in vacuo to give 2.68 g of the title compound, mp. 84°–86° C.

Anal. Calc'd. for $C_{19}H_{30}ClN_3O_4$: C, 57.05; H, 7.58; N, 10.51. Found: C, 56.82; H, 7.55; N, 10.40.

EXAMPLE 55

4-Amino-5-chloro-2-[2-(dimethylamino)-2-oxoethoxy]-N-[2-diethylamino)ethyl]benzamide The general procedure of Example 40 was repeated except that the methylamine utilized therein was replaced by dimethylamine. After reacting for 6 days the mixture was concentrated in vacuo and the residue partitioned between water and methylene chloride. The organic phase was dried, concentrated in vacuo, and the residue crystallized from methanol-methylene chloride-ether to give the title compound as a white solid containing one-half mole of water of crystallization, mp. 130°–131° C.

Anal. Calc'd. for $C_{17}H_{27}ClN_4O_3 \cdot \frac{1}{2}H_2O$: C, 53.74; H, 7.42; Cl, 9.33; N, 14.36. Found: C, 54.09; H, 7.17; Cl, 9.02; N, 14.74.

EXAMPLE 56

4-Amino-5-chloro-N-[2-(diethylamino)ethyl]-2-(4-diethylamino-4-oxobutoxy)benzamide To a well-stirred suspension of pentane-washed sodium hydride (0.52 g of 60%, 3 mmole) in 3 ml dry DMF was added 4-amino-5-chloro-N-[2-(diethylamino)ethyl]-2-hydroxybenzamide (3.43 g, 12 mmoles) (prepared as Example 53). To this was added 10 ml of DMF and the mixture was stirred at ambient temperature for 45 minutes then warmed to about 50° C. for 15 minutes whereupon 4-chloro-N,N-diethylbutyramide (1.92 g, 11 mmoles) was added. The mixture was then stirred at 60°–70° C. for 6 hours, at room temperature for 2 days and then at 60°–70° C. for a further 4 hours. After cooling, the mixture was poured into 400 ml of brine and extracted with methylene chloride (4×100 ml). After combining, the organic phase was washed two times with 100 ml of 10% aqueous sodium hydroxide and brine, dried over sodium sulfate, filtered and concentrated in vacuo to give an oil (3.75 g). This was purified by flash chromatography on silica gel to give 1.64 g of the title compound as an oil.

Anal. Calc'd. for $C_{21}H_{35}ClN_4O_3$: C, 59.06; H, 8.28; N, 13.12. Found: C, 57.71; H, 8.15; N, 12.71.

EXAMPLE 57

2-(2-Acetoxyethoxy)-4-amino-5-chloro-N-[2-(diethylamino)ethyl]-benzamide

A solution of the tetrabutylammonium salt of 4-amino-5-chloro-N-[2-(diethylamino)ethyl]-2-hydroxybenzamide (5.27 g, 10 mmoles) (prepared in Preparation No. 3) in acetonitrile (100 ml) and 2-bromoethylacetate (2 g, 12 mmoles) was stirred for 48 hours. The solvent was evaporated and the residue partitioned between ethyl acetate and water. The organic layer was washed with ice-cold 0.4N sodium hydroxide solution, water, dried and the solvent evaporated. The residue was chromatographed over deactivated silica using methylene chloride (100 ), methanol (2), ammonia (0.5) solvent system. The appropriate fractions were combined and the solvent evaporated to leave a residue of 3.18 g (85%) of the title compound. Crystallization from toluene gave a sample, mp. 101°–102° C.

Anal. Calc'd. for $C_{17}H_{26}ClN_3O_4$: C, 54.91; H, 7.05; N, 11.30. Found: C, 54.86; H, 7.01; N, 11.28.

EXAMPLE 58

4-Amino-5-chloro-N-[2-diethylamino)ethyl]-2-[4-(methylsulfinyl)butoxy]benzamide (A)

4-Amino-5-chloro-N-[2-(diethylamino)ethyl]-2-[4-(methylthio)butoxy]benzamide

A mixture of tetrabutylammonium salt of 4-amino-5-chloro-N-[2-(diethylamino)ethyl]-2-hydroxybenzamide (15.82 g, 30 mmoles) (prepared in Preparation No. 3) in DMF (150 ml) and 1,4-dibromobutane (6.48 g, 30 mmoles) was stirred for 24 hours. The solution was chilled and poured into a 500 ml flask containing sodium hydride (1.5 g, 37.5 mmoles, of a 60% emulsion washed with pentane). The suspension was cooled in ice, stirred and methyl mercaptan was passed into the mixture until the evolution of hydrogen ceased. The clear solution was heated at 35°–50° C. for 5 hours, poured into 1400 ml of water and extracted with ethyl acetate. The organic layer was washed with water, dried, and the solvent evaporated. The residue was chromatographed over deactivated silica, using methylene chloride (100), methanol (2), ammonia (0.5) solvent system. Two compounds were obtained: (1) 1,4-bis{4-amino-5-chloro-N-[2-(diethylamino)-ethyl]-2-oxybenzamide}butane, mp. 172°–176° C. and 2) the title compound, 2.5 g crystallized from 2-propanol, mp. 101°–103° C.

Anal. Calc'd. for $C_{18}H_{30}ClN_3O_2S$: C, 55.72; H, 7.79; N, 10.83; Cl, 9.14; S, 8.27. Found: C, 55.59; H, 7.87; N, 10.81; Cl, 9.26; S, 8.19.

(B)
4-Amino-5-chloro-N-[2-(diethylamino)ethyl]-2-[4-methylsulfinyl)butoxy]benzamide The general procedure from Example 21 is repeated except that the 4-amino-5-chloro-N-[2-(diethylamino)ethyl]-2-[2-(methylthio)ethoxy]benzamide utilized therein was replaced with the product from Step A to give the title compound in 78% yield after chromatography of silica and crystallization from methylene chloride-ether, as a solid, mp. 80°–83° C.

Anal. Calc'd. for $C_{18}H_{30}ClN_3O_3S$: C, 53.51; H, 7.49; N, 10.40; Cl, 8.78; S, 7.94. Found: C, 53.70; H, 7.72; N, 10.36; Cl, 8.40; S, 7.78.

EXAMPLE 59

4-Amino-5-chloro-N-[2-(diethylamino)ethyl]-2-[2-(1-pyrrolidinyl)-2-oxoethoxy]benzamide A solution of 4-amino-5-chloro-N-[2-(diethylamino)ethyl]-2-(2-methoxy-2-oxoethoxy)benzamide (1.07 g, 3 mmoles) (prepared in Example 15) in methanol (10 ml) and pyrrolidine (0.952 g, 23 mmoles) was refluxed overnight. The solvent was evaporated and the residue was chromatographed over deactivated silica using methylene chloride (100), methanol (2.5), ammonia (0.5) solvent system. The appropriate fractions were combined, the solvent evaporated and the residue crystallized from 2-propanol and recrystallized from methanol-ether to yield 0.86 g (72%) of the title compound, mp. 160°–162° C.

Anal. Calc'd. for $C_{19}H_{29}ClN_4O_3 \cdot \frac{1}{4}H_2O$: C, 56.84; H, 7.40; N, 13.96. Found: C, 56.89; H, 7.24; N, 13.67.

EXAMPLE 60

4-Amino-5-chloro-N-[2-(diethylamino)ethyl]-2-[2-ethylsulfinyl)ethoxy]benzamide (A)
4-Amino-5-chloro-N-[2-(diethylamino)ethyl]-2-[2-ethylthio)ethoxy]benzamide The general procedure of Example 20 was repeated except that the 2-chloroethyl methyl sulfide utilized therein was replaced with 2-chloroethyl ethyl sulfide to give the title compound as an off-white solid from acetonitrile, mp. 92°–94° C., in 61% yield.

Anal. Calc'd. for $C_{17}H_{28}ClN_3O_2S$: C, 54.60; H, 7.55; N, 11.24; Cl, 9.48; S, 8.58. Found: C, 54.14; H, 7.57; N, 10.97; Cl, 9.03; S, 8.58.

(B)
4-Amino-5-chloro-N-[2-(diethylamino)ethyl]-2-[2-(ethylsulfinyl)ethoxy]benzamide Substitution of the product from Step A in the procedure of Example 21 gave the title compound in 53% yield as light yellow, shiny crystals, mp. 140°–142° C. after recrystallization from acetonitrile.

Anal. Calc'd. for $C_{17}H_{28}ClN_3O_3S$: C, 52.36; H, 7.24; N, 10.78; Cl, 9.09; S, 8.22. Found: C, 52.56; H, 7.38; N, 10.75; Cl, 8.89; S, 8.21.

EXAMPLE 61

Cis-4-amino-5-chloro-N-{1-[3-(4-fluorophenoxy)-propyl]-3-methoxy-4-piperidinyl}-2-[2-(methylthio)ethoxy]benzamide monohydrate (A)
Cis-4-amino-5-chloro-N-{1-[3-(4-fluorophenoxy)-propyl]-3-methoxy-4-piperidinyl}-2-hydroxybenzamide The general procedure of Preparation No. 1 was repeated except that the 4-amino-5-chloro-N-[2-(diethylamino)ethyl]-2-methoxybenzamide utilized therein was replaced by cis-4-amino-5-chloro-N-{1-[3-(4-fluorophenoxy)propyl]-3-methoxy-4-piperidinyl}-2-methoxybenzamide (2 g, 4.3 mmoles) [prepared according to the procedure described in published European patent application No. 76,530 (1983)]. The product was crystallized from 2-propanol to give the title product in 54% yield, mp. 146°–148° C.

Anal. Calc'd. for $C_{22}H_{27}ClFN_3O_4$: C, 58.34; H, 6.01; N, 9.28; Cl, 7.83. Found: C, 58.31; H, 6.19; N, 9.12; Cl, 7.88.

(B)
Cis-4-amino-5-chloro-N-{1-[3-(4-fluorophenoxy)-propyl]-3-methoxy-4-piperidinyl}-2-[2-(methylthio)ethoxy]benzamide monohydrate The product from Step A (0.45 g, 1 mmole) was added to a stirred suspension of sodium hydride (40 mg, 1 mmole of 60%, washed with petroleum ether) in acetonitrile (10 ml) followed by tetrabutylammonium bromide (0.32 g, 1 mmole). The reaction mixture was heated to 40° C. for 15 minutes, and there was then added 2-chloro-ethyl methyl sulfide (0.44 g, 4 mmole) and potassium iodide (50 mg). The mixture was heated to reflux for 2 hours. The solvent was evaporated and the residue was partitioned between ethyl acetate (containing 10% of methylene chloride) and water. The organic layer was dried and the solvent evaporated to leave a residue. The residue was crystallized from 2-propanol to yield 0.26 g (50%) of the title compound, mp. 58°–60° C.

Anal. Calc'd. for $C_{25}H_{33}ClFN_3O_4S \cdot H_2O$: C, 55.18; H, 6.48; N, 7.72 Found: C, 55.46; H, 6.42; N, 7.47

EXAMPLE 62

Cis-4-amino-2-(2-amino-2-oxoethoxy)-5-chloro-N-{1-[3-(4-fluorophenoxy)propyl]-3-methoxy-4-piperidinyl} benzamide sesquihydrate Cis-4-amino-5-chloro-N-{1-[3-(4-fluorophenoxy)-propyl]-3-methoxy-4-piperidinyl}-2-hydroxybenzamide (1.35 g, 3 mmoles) (prepared in Example 61, Step A) was added to a stirred suspension of sodium hydride (0.12 g, 3 mmoles of 60% emulsion, washed with petroleum ether) in acetonitrile (20 ml) followed by tetrabutylammonium bromide (0.96 g, 3 mmoles). The reaction mixture was heated to 40° C. for 15 minutes and then treated with methyl bromoacetate (0.92 g, 6 mmoles). After stirring for 2 days the reaction mixture was partitioned between water and ethyl acetate. The organic phase was dried, concentrated in vacuo and the residue was chromatographed over deactivated silica using a methylene chloride (100), methanol (2), ammonia (0.5) solvent system. The appropriate fractions were combined and the solvent evaporated. The residue was dissolved in methylene chloride by adding methanol and the solution was saturated with gaseous ammonia in the cold. After 30 minutes the solvent was evaporated and the residue crystallized from ethanol-water to yield 0.3 g of the title compound as a sesquihydrate (19%), mp. 173°–175° C.

Anal. Calc'd. for $C_{24}H_{30}ClFN_4O_5 \cdot 1\tfrac{1}{2}H_2O$: C, 53.78; H, 6.20; N, 10.45. Found C, 53.59; H, 6.21; N, 10.36.

The above product was also prepared in the following alternative manner.

Cis-4-amino-5-chloro-N-{1-[3-(4-fluorophenoxy)-propyl]-3-methoxy-4-piperidinyl}-2-hydroxybenzamide (0.68 g, 1.5 mmoles) (prepared in Example 61, Step A) was added to a stirred suspension of sodium hydride (60 mg, 1.5 mmole of 60% emulsion, washed with petroleum ether) in acetonitrile (10 ml) followed by tetrabutylammonium bromide (0.48 g, 1.5 mmole). The reaction mixture was heated to 40° C. for 15 minutes to obtain a clear solution and treated with chloroacetamide (0.56 g, 6 mmoles) potassium iodide (0.25 g) and heated to reflux. The solvent was evaporated and the residue was partitioned between ethyl acetate and water. The residue from the organic layer was chromatographed over deactivated silica using methylene chloride (100), methanol (2), ammonia (0.5) solvent system. The appropriate fractions were combined and the residue (0.2 g) was crystallized from ethanol water to yield the title compound (60 mg), mp. 173°–175° C.

EXAMPLE 63

4-Amino-5-chloro-N-[(2-diethylamino)ethyl]-2-(2-methoxypropan-1-yloxybenzamide

The general procedure of Example 31 was repeated, except that the 3-bromo-3-methyl-2-butanone used therein was replaced by an equimolar amount of 1-chloro-2-methoxypropane, and the title compound was obtained. Purity, after rechromatography, was >95% (HPLC).

Anal. Calc'd. for $C_{17}H_{28}ClN_3O_3$: C, 57.05; H, 7.89; N, 11.74; Cl, 9.91. Found: C, 56.85; H, 7.92; N, 11.56; Cl, 9.90.

EXAMPLE 64

4-Amino-5-chloro-N-[(2-diethylamino)ethyl]-2-[(2-hydroxy-2-methyl)propan-1-yl]oxybenzamide The general procedure of Example 31 was repeated, except that the 3-bromo-3-methyl-2-butanone used therein was replaced by an equimolar amount of 1-chloro-2,3-epoxy-2-methylpropane, and the thus obtained intermediate was reduced with sodium borohydride by the procedure described in Example 41, and the title compound was thereby produced. Mp. 87°–89° C.

EXAMPLE 65

The general procedure of Example 64 is repeated, except that the 1-chloro-2,3-epoxy-2-methylpropane utilized therein is replaced by an equimolar amount of 2-chloro-3,4-epoxy-3-methylbutane, and 4-amino-5-chloro-N-[(2-diethylamino)ethyl]-2-[(2-hydroxy-2-methyl)but-3-yl]oxybenzamide is thereby produced.

EXAMPLE 66

The general procedure of Example 63 is repeated, except that the 1-chloro-2-methoxypropane utilized therein is replaced by an equimolar amount of 2-chloro-3-methoxybutane, and 2-chloro-3-methoxy-3-methylbutane, respectively, and there is thereby produced a mixture of threo- and erythro-4-amino-5-chloro-N-[(2-diethylamino)ethyl]-2-[(2-methoxy)but-3-yl]oxybenzamide, and 4-amino-5-chloro-N-[(2-diethylamino)ethyl]-2-[(2-methoxy-2-methyl)but-3-yl]oxybenzamide, respectively.

FURTHER DETAILED DESCRIPTION OF THE INVENTION

Some additional compounds similar to those defined hereinabove by formula I have been made, tested, and found to have useful gastro-intestinal properties. These new compounds, as well as the foregoing compounds of formula I, supra., are useful in the treatment of emesis, particularly emesis resulting from standard cancer treatments, such as chemotherapy, e.g., cisplatin treatment, and/or radiation treatment. These additional compounds are embodied as Formula I'

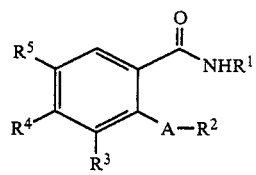

For compounds of formula I': $R^3$, $R^4$, and $R^5$, are as previously defined for compounds for formula I. The definition for $R^1$, however is expanded in formula I' to include the (1-azabicyclo[2.2.2]-oct-3-yl) moiety, also known as a 3-quinuclidinyl radical, as shown below.

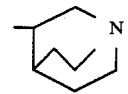

3-quinuclidinyl $R^1$ also encompasses the definitions as previously given for formula I. The definition for $R^2$ is also expanded in formula I' to include

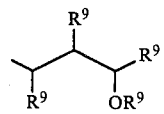

wherein $R^9$ is as previously defined supra. for compounds of formula I. As in the case of $R^1$, $R^2$ also encompasses the definitions given previously for $R^2$ in formula I.

Additionally, for compounds of formula I' where $R^1$ is the 1-azabicyclo[2.2.2]-oct-3-yl moiety, $R^2$ is further expanded to include alkenyl and alkynyl. Preferred compounds of this subclass comprise N-(1-azabicyclo[2.2.2]-oct-3-yl) benzamides wherein $R^2$ is allyl and propargyl.

Concerning compounds of formula I' wherein $R^1$ is a (1-azabicyclo[2.2.2]-oct-3-yl) moiety, attention is called to European patent application No. 158,532 of Munson and Boswell which was published Oct. 16, 1985. This application disclosed 2-alkoxy-N-(1-azabicyclo[2.2.2]- oct-3-yl)benzamides and thiobenzamides having the formula

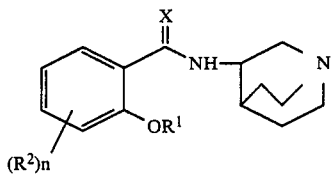

in which X is oxygen or sulfur; $R^1$ is lower alkyl; $R^2$ is hydrogen, halogen, 4,5-benzo, alkoxy or Am wherein Am is amino, methylamino or dimethylamino, and n is 1 or 2. These compounds may be distinguished from the instant compounds of formula I' as substructure A-$R^2$ of I' (which compares to substructure $OR^1$ of the European application) has a variety of definitions but never includes lower alkoxy, the only definition given for the art compounds.

The compounds of Formula I' may be synthesized by employing methods described in the chemical literature and/or modifying the synthetic methods already described for the componds of formula I, supra., in a manner which would be obvious to one skilled in the pertinent art.

Preferred compounds of Formula I' are those compounds having structure II'

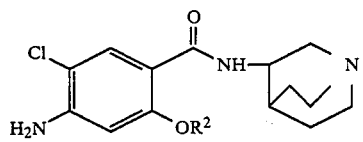

wherein $R^2$ is as defined for formula I' and includes alkenyl and alkynyl. These preferred formula II' compounds may be prepared by methods such as those outlined below. Additional synthesis processes as well as modifications of the synthetic methods described hereinbelow would be obvious to one skilled in the pertinent art.

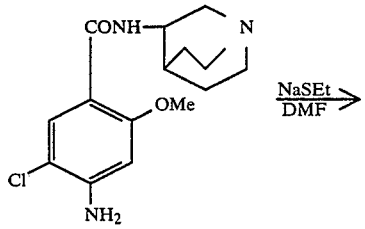

NaSEt / DMF →

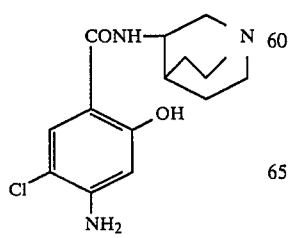

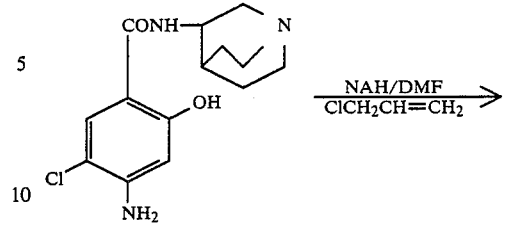

NAH/DMF / ClCH₂CH=CH₂ →

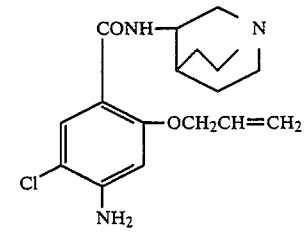

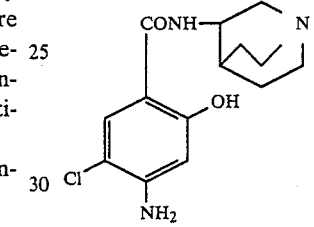

NAH/DMF / Cl →

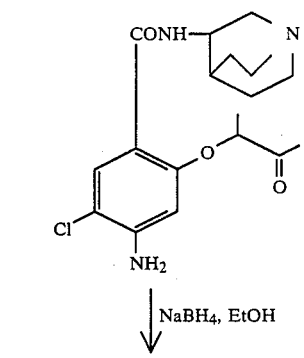

↓ NaBH₄, EtOH

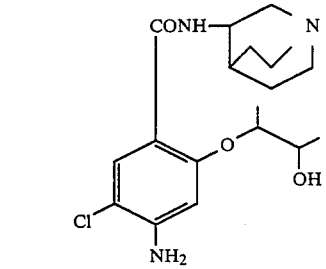

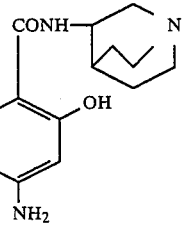

NAH, DMF / ClCH₂CH₂S—Me →

-continued

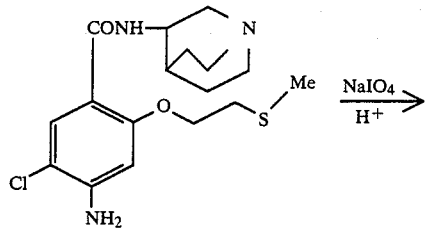

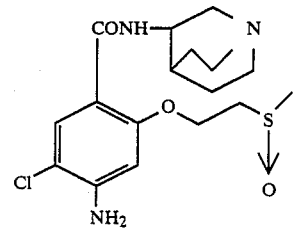

For all compounds of the instant invention, i.e. compounds of Formula I and I', the invention also relates to a method of alleviating nausea and vomiting in a warm-blooded mammal in need thereof, which comprises systemic administration to said mammal of an effective anti-emetic amount of at least one compound of formula I or I', or a salt, hydrate, or solvent thereof, in a pharmaceutically accepted carrier. The invention also relates to an method of treating disorders related to impaired gastric motility in a warm-blooded mammal, which similarly comprises systemic administration to said mammal of an effective gastric motility facilitating amount of at least one compound of the instant series, or a salt, hydrate or solvent thereof, in a pharmaceutically acceptable carrier.

The term systemic administration as used herein refers generally to oral, rectal, and parenteral, which routes further include intranasal administration, sublingual administration, administration via the buccal cavity, and transdermal administration as well as the more common intramuscular, intravenous and subcutaneous routes.

A preferred use for compounds of the instant invention relates to their use in alleviating nausea and vomiting in cancer patients who are undergoing cancer therapy such as chemotherapy and/or radiation treatment. It is further intended that in cases of chemotherapeutic treatments with anti-cancer agents, such as cisplatin, for example that a selected compound of the instant series and a selected anti-cancer chemotherapeutic agent may be co-administered to the patient and that to facilitate such co-administration pharmaceutical compositions for effecting such treatment would be utilized and such compositions will contain at least one compound of the present invention in combination with the selected cancer chemotherapeutic agnet and a pharmaceutical carrier. It is envisioned that the instant compounds would be useful against nausea and vomiting associated with certain medical procedures post-operative trauma, motion-sickness related disorders, and general nausea and vomiting of unknown origin.

The scope of the instant invention is hereby expanded to include the componds defined by formula I' as well as those heretofore embraced by formula I. The present subject matter can now be defined by formula XXI (shown below) which is comprised of the compounds of formula I and I'

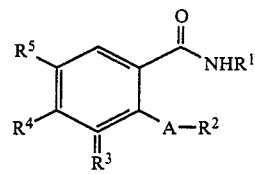

and the pharmaceutically accepted acid addition salts, hydrates and/or solvates thereof. For compounds of formula XXI:

$R^3$ is hydrogen or, when $R^4$ and $R^5$ are each hydrogen, $R^3$ may be (lower)alkoxy;

$R^4$ is hydrogen, amino or (lower)alkoxy;

$R^5$ is hydrogen, chloro, bromo, fluoro, trifluoromethyl, (lower)alkylthio, (lower)alkanesulfinyl, (lower)alkanesulfonyl, sulfamyl or

or $R^4$ and $R^5$, taken together, may be —HN—N=N—;

$R^6$ is (lower)alkyl, (lower)alkenyl or (lower)alkynyl;

$R^1$ is

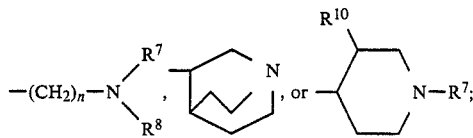

wherein n is an integer of from 1 to 4, inclusive;

$R^7$ and $R^8$ are the same or different and are (lower)alkyl, (lower)alkenyl, (lower)alkynyl,

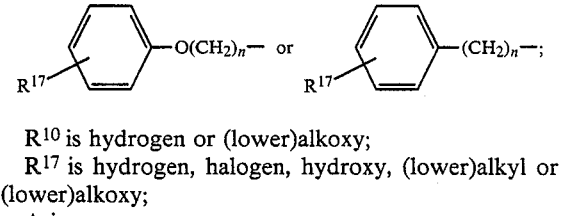

$R^{10}$ is hydrogen or (lower)alkoxy;

$R^{17}$ is hydrogen, halogen, hydroxy, (lower)alkyl or (lower)alkoxy;

A is oxygen or

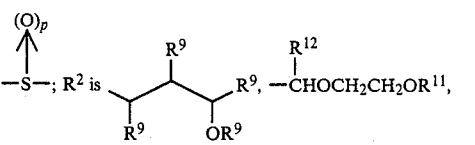

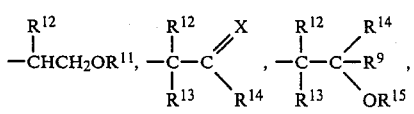

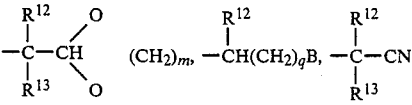

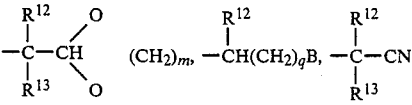

-continued

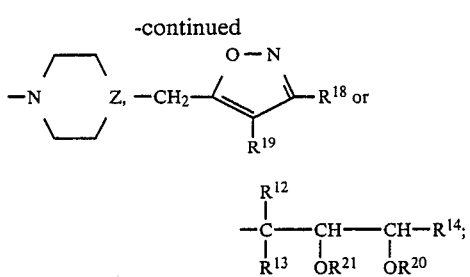

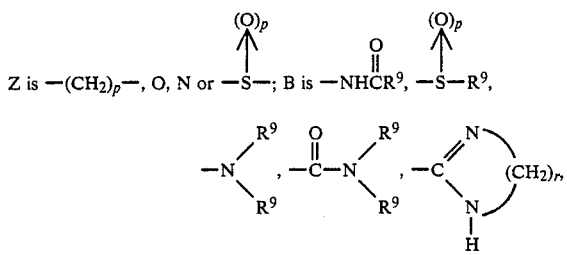

wherein
X is oxygen, sulfur or =NOR$^{16}$;

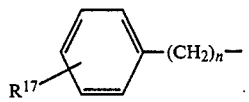

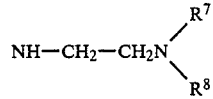

pyridyl or oxazolidinyl;
m is 2 or 3;
p is 0, 1 or 2;
q is an integer of from 0 to 4, inclusive;
r is 2 or 3;
R$^9$ is hydrogen or (lower)alkyl;
R$^{11}$, R$^{12}$, R$^{13}$, R$^{15}$ and R$^{16}$ are the same or different, and are hydrogen, (lower)alkyl, (lower)alkenyl, (lower)alkynyl, (lower)alkoxy(lower)alkyl, cycloalkyl containing from 5 to 7 carbon atoms, inclusive, or

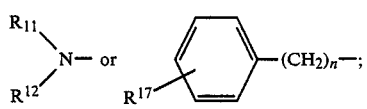

provided that, when R$^{11}$, R$^{15}$ or R$^{16}$ is (lower)alkenyl or (lower)alkynyl, the unsaturated carbon atom may not be directly attached to an oxygen or nitrogen atom;
R$^{14}$ is hydrogen, halogen, (lower)alkyl, (lower)alkenyl, (lower)alkynyl, cycloalkyl containing from 5 to 7 carbon atoms, inclusive, hydroxy, (lower)alkoxy, (lower)alkenyloxy, (lower)alkoxycarbonyl(lower)alkenyl, hydrazino, acetylhydrazino, thienyl, phenyl,

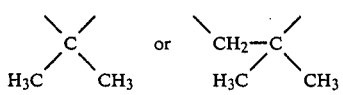

R$^{18}$ and R$^{19}$ are the same or different and are hydrogen or (lower)alkyl;
R$^{20}$ and R$^{21}$ are each hydrogen or, taken together, represent

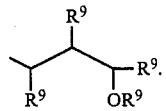

or R$^{12}$ and R$^{13}$, taken together with the carbon atom to which they are attached, may form a saturated ring of from 5 to 7 atoms, inclusive, optionally containing at least one heteroatom selected from oxygen, sulfur and nitrogen;

or R$^{12}$ and R$^{14}$, taken together with the carbon atoms to which they are attached, may form a saturated or unsaturated ring of from 5 to 7 atoms, inclusive, optionally containing at least one heteroatom selected from oxygen, sulfur and nitrogen;

or R$^{14}$ and R$^{15}$, taken together with the carbon and oxygen atoms to which they are attached, may form a 3 to 7 membered saturated oxygen-containing ring, and when R$^1$ is 1-azabicyclo[2.2.2]-oct-3-yl, R$^2$ can be alkenyl and alkynyl.

Also included within the scope of this invention are all possible optical and geometric isomers of the compounds of formula XXI as well as tautomeric forms where applicable.

Preferred groups of compounds of Formula XXI correspond to preferred compounds of Formula I but with R$^1$ expanded to include the 1-azabicyclo[2.2.2]oct-3-yl moiety and R$^2$ expanded to include $$\begin{matrix} & R^9 & \\ & | & \\ \diagdown & \diagup & R^9. \\ R^9 & OR^9 & \end{matrix}$$

Also preferred are formula XXI compound with R$^1$ being 1-azabicyclo[2.2.2]oct-3-yl and R$^2$ being alkenyl and alkynyl. More preferred compounds of the instant invention are those wherein R$^3$ is hydrogen, R$^4$ is amino, and R$^5$ is chloro. Of these there are two groups of most preferred compounds:

(1) compounds wherein R$^1$ is $$NH-CH_2-CH_2N\diagup^{R^7}_{R^8}$$

and (2) compounds wherein R$^1$ is 1-azabicyclo[2.2.2]oct-3-yl. The definitions of R$^2$, R$^7$-R$^{21}$, X, Z, B, m, p, q, and r are as previously defined for preferred compounds.

Additional support for compounds of formula XXI is provided by the further representative examples supplied below.

EXAMPLE 67 erythro-4-Acetamido-5-chloro-N-[2-(diethylamino)ethyl]-2-[2-acetoxy)but-3-yl]oxybenzamide and threo-4-acetamido-5-chloro-N-[2-(diethylamino)ethyl]-2-[(2-acetoxy)-but-3-yl]oxybenazmide 4-Amino-2-(butan-2-one-3-yl)oxy-5-chloro-N-[2-(diethylamino)ethyl]benzamide hydrochloride (prepared in Example 7) (30.0 g; 0.0765 mole) was added to 300 ml of abs. ethanol and the mixture was warmed to ca. 50° C. The heat source was removed and sodium borohydride (3.18 g; 0.084 mole) was added slowly, in small portions, with good stirring. When the addition was complete the mixture was stirred at reflux for one hour. The reaction mixture was filtered, the ethanol removed in vacuo and the residue was treated with 100 ml of water followed by 40 ml of 3N HCl. The acid solution was extracted twice with ether (discarded), cooled in an ice bath and made strongly basic with 40% NaOH. The separated oil was then extracted with several portions of CH₂Cl₂, dried over Na₂SO₄ and the solvent evaporated to leave 25.88 g of sticky gum. An nmr (CDCl₃) showed ca. 7:3 mixture of threo to erythro diastereoisomers. Some enrichment of the erythro isomer was effected by crystallizing from the mixutre the threo isomer (6.60 g) using solvent systems of ethyl acetate/skelly B, nitro- (97.4% pure), 2.12 g threo isomer (94% pure) and 1.14 g of erythro isomer (94.8% pure).

Anal. (erythro isomer) Calc'd. for $C_{21}H_{32}ClN_3O_5$: C, 57.07; H, 7.30; N, 9.51. Found: C, 56.67; H, 7.25; N, 9.56.

Anal. (threo isomer) Cal'd. for $C_{21}H_{32}ClN_3O_5$: C, 57.07; H, 7.30; N, 9.51. Found: C, 56.68; H, 7.26; N, 9.25.

¹H-NMR DATA-All spectra were run in CDCl₃

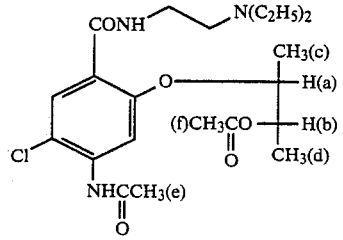

| | | Assignment (ppm) | | erythro | threo |
|---|---|---|---|---|---|
| Proton | Shape | erythro | threo | | |
| C-6 | s | 8.30 | 8.30 | J(a-b) = 6.4 Hz | 4.4 Hz |
| C-3 | s | 8.20 | 8.18 | J(a-c) = 6.4 Hz | 6.4 Hz |
| a | m | 5.15 | 5.13 | J(b-d) = 6.4 Hz | 6.4 Hz |
| b | m | 4.56 | 4.60 | | |
| c | d | 1.34 | 1.38 | | |
| d | d | 1.27 | 1.31 | | |
| e | s | 2.24 | 2.24 | | |
| f | s | 1.99 | 2.03 | | | methane and toluene/ether.

The mother liquors from the collected crystals were evaporated to dryness and the residual oil (ca. 20 g of the intermediate alcohol; 0.0559 mole) was dissolved in 200 ml of pyridine. 31.6 ml of acetic anhydride (34.23 g; 0.335 mole) was added and the solution was heated in an oil bath at 72°-75° C. (oil bath temperature) for one hour and at 100°-105° C. for 2.5 hours. The reaction solution was concentrated at reduced pressure and the residue was partitioned between water and CH₂Cl₂. 40% NaOH was added to make the aqueous layer strongly basic and then extracted with several portions of CH₂Cl₂. The combined extracts were dried and the solvent evaporated to give a mixture of the diacylated products as a dark oil.

The crude mixture was purified by flash chromatography on 400 g of silica gel (32-63 μm) using 98 CH₂Cl₂:2 CH₃OH:0.3% NH₄OH as the eluant. 34×400 ml fractions were collected and combined into four lots as follows:

Fractions 9, 10, 11, 6.62 g (92:8 threo:erythro)
Fractions 12-17, 5.62 g (86:14 threo:erythro)
Fractions 18-25, 10.28 g (57:43 threo:erythro)
Fractions 26-33, 4.46 g (14:86 threo:erythro)

Determination of the isomer ratio was done by analytical HPLC using a 10μ Alltech silica 600 column and a mobil phase of 800 CH₂Cl₂:8 IPA: 4 NH₄OH; UV detector at 280 nm.

Separation of the two diastereoisomers was effected by chromatographing the four lots (in six runs) on a Waters Prep 500 HPLC System.

Column: new silical gel comumn (1)
Detector: refractive index
Mobile Phase: CH₂Cl₂+2-5% IPA+0.5% NH₄OH Each of the collected fractions was assayed on the analytical HPLC and the appropriate ones were combined to yield 4.44 g of amber oil that was 96.8% pure erythro isomer. Also isolated was 6.74 g of the threo isomer

EXAMPLE 68 erythro-4-Amino-5-chloro-N-[2-(diethylamino)ethyl]-2-[2-hydroxy)but-2-yl]oxybenzamide erythro-4-Acetamido-5-chloro-N-[2-(diethylamino)ethyl]-2-[2-acetoxy)but-3-yl]oxybenzamide (4.42 g; 10 mmoles) (prepared in Example 67) was dissolved in methanol, treated with 15 ml of 4.0N NaOH and stirred at reflux for one hour. The methanol was removed at reduced pressure and the residue was partitioned between water and CH₂Cl₂. The aqueous layer was extracted once more with CH₂Cl₂ and the combined extracts were dried and evaporated to dryness to give a yellow gum. An additional purification by flash chromatography on 60 g of silica gel (32-63 μm) using 95 CH₂Cl₂:5 CH₃OH:0.3% NH₄OH as the eluant gave the title compound as a hard, yellow gum, yield: 2.81 g (78.5%). ¹H-NMR analysis showed 3.5% of the threo isomer to be present.

Anal. Calc'd. for $C_{17}H_{28}ClN_3O_3$: C, 57.05; H, 7.89; N, 11.74. Found: C, 56.70; H, 7.99; N, 11.41.

EXAMPLE 69 threo-4-Amino-5-chloro-N-[2-(diethylamino)ethyl]-2-[(2-hydroxy)but-3-yl]oxybenzamide A solution of threo-4-acetamido-5-chloro-N-[2-(diethylamino)ethyl]-2-[(2-acetoxy)but-3-yl]oxybenzamide (6.70 g; 15.2 mmoles) (prepared in Example 67) was dissolved in 80 ml of methanol, treated with 15 ml of 4N NaOH and stirred at reflux for one hour. The methanol was removed at reduced pressure and the residue was partitioned between water and CH₂Cl₂. The aqueous layer was extracted once more with CH₂Cl₂ and the combined extracts were dried and evaporated to a yellow gum. This gum was purified by flash chromatography on 100 g of silica gel (32-63 μm) using 95 CH₂Cl₂:5 CH₃OH:0.3% NH₄OH as the eluant. The appropriate fractions were combined to give the title alcohol as a hard, yellow gum, weight=4.00 g.

Anal. Calc'd. for $C_{17}H_{28}ClN_3O_3$: C, 57.05; H, 7.89; N, 11.74; Cl, 9.91. Found: C, 56.70; H, 7.84; N, 11.63; Cl, 10.63.

$^1$H-NMR DATA—All spectra were run in $CDCl_3$

| | | Assignment (ppm) | | erythro | threo |
|---|---|---|---|---|---|
| Proton | Shape | erythro | threo | J(a-b) = 5.9 Hz | 2.2 Hz |
| C-6 | s | 8.04 | 8.08 | J(a-c) = 6.6 Hz | 6.6 Hz |
| C-3 | s | 6.25 | 6.27 | J(b-d) = 6.6 Hz | 6.6 Hz |
| a | m | 3.64 | 3.72 | | |
| b | m | 3.42 | 3.32 | | |
| c | d | 1.35 | 1.30 | | |
| d | d | 1.24 | 1.14 | | |

EXAMPLE 70 threo-4-Amino-5-chloro-N-[2-(diethylamino)ethyl]-2-[(2-hydroxy)but-3-yl]oxybenzamide A solution of 4-amino-2-(butan-2-one-3-yl)oxy-5-chloro-N-[2-(diethylamino)ethylbenzamide (3.0 g; 7.65 mmoles) (prepared in Example 7) in 35 ml of dry THF was cooled to −78° C. and treated with lithium tri-s-butylborohydride (L-Selectride, 8.03 ml of a 1M solution in THF) with good stirring. After 20 min the cooling bath was removed and the yellow solution was allowed to warm to RT°. 9.30 ml of 1.0N NaOH was added to the solution, dropwise, and the THF was removed at reduced pressure. The residue was partitioned between ether and water and the ether layer was wased once again with water.

The ether solution was extracted once with 10 ml of 1.0N HCl and the extract backwashed once with ether. The acid layer was then cooled in an ice bath, basified with 3 ml of 4N NaOH and the alcohol was extracted into several portions of $CH_2Cl_2$. After evaporation of the solvent there remained 2.30 g of yellow gum which contained ca. 6% of the erythro isomer.

The crude product was purified by flash chromatography on 50 g of silica gel (32–63 μm) using a gradient elution of methanol-methylene chloride containing 0.3% $NH_4OH$. The appropriate fractions were combined and evaporated to give 2.10 g of yellow gum that slowly started to crystallize. Recrystallization from ethyl acetate yielded 0.631 g (23%) of the title compound as a white solid, m.p.=111°–113° C.

Anal. Calcd. for $C_{17}H_{28}ClN_3O_3$: C, 57.05; H, 7.89; N, 11.74; Cl, 9.91. Found: C, 56.80; H, 7.84; N, 11.77; Cl, 10.38.

EXAMPLE 71 cis- and trans-4-Amino-5-chloro-2-(cyclohexane-1-ol)oxy-N-[(2-diethylamino)ethyl]oxybenzamides A solution of 4-amino-5-chloro-2-(cyclohexanon-2-yl)oxy-N-[(2-diethylamino)ethyl]-benzamide (3.3 g; 8.7 mmoles) in absolute ethanol (50 ml) was cooled to 0° C. and sodium borohydride (0.5 g, 13.2 mmoles) was added portionwise over 15 minutes. The resulting mixture was heated to reflux for 3 hours and then quenched with 1N HCl. Extraction with $CH_2Cl_2$ (4X) resulted in a mixture of cis and trans cyclohexyl alcohols which were separated by silica gel chromatography to yield pure 4-amino-5-chloro-2-(trans, 1,2-cyclohexane-1-ol)oxy-N-[2-(diethylamino)ethyl]benzamide [NMR ($CDCl_3$) δ 8.4 (br s, 1H); 8.0 (s, 1H); 6.3 (s, 1H); 4.3 (s, 2H); 3.9 (dt, 1H); 3.7 (br m, 2H; 3.4 (m, 1H); 2.7 (m, 6H); 1.7 (br d, 1H); 1.43–1.10 (br m, 8H); 1.03 (t, 6H)] and 4-amino-5-chloro-2-(cis, 1,2-cyclohexane-1-ol)oxy-N-[2-(diethylamino)ethyl]benzamide [NMR ($CDCl_3$) δ8.7 (s, 1H); 8.07 (s, 1H); 6.27 (s, 1H); 4.30 (br s, 2H); 4.21 (br d, 1H); 4.01 (m, 1H); 3.78 (br m, 1H); 3.31 (br m, 1H); 2.72 (br m, 6H); 1.9–1.27 (br m, 9H); 1.03 (t, 6H)] as gummy foams.

EXAMPLE 72

4-Amino-5-chloro-N-[2-(diethylamino)ethyl]-2-(3-methoxybut-1-yl)oxybenzamide

A stirred solution of 4-amino-5-chloro-N-[2-(diethylamino)ethyl]-2-hydroxybenzamide (1.715 g, 6 mmoles; prepared according to Preparation 1B), triphenylphosphine (1.58 g, 6 mmoles), 3-methoxy-1-butanol (0.62 g, 6 mmoles) in dry tetrahydrofuran (50 ml) was treated dropwise with diethyl azodicarboxylate (1.1 g of 95% purity material, 6 mmoles). The solution was left to stir overnight. After evaporation of the solvent the residue was dissolved in methylene chloride. The solution was washed with 0.4N NaOH, water, dried and the solvent evaporated. The residue was chromatographed over deactivated silica using methylene chloride (100), methanol (2.5), ammonium hydroxide (0.5) solvent system. The appropriate fractions were combined and the solvent evaporated. The residue (1.7 g) was crystallized from toluene to yield 1.17 g (52%) of the title compound, m.p. 76°–78° C.

Anal. Calc'd. for $C_{18}H_{30}ClN_3O_3$: C, 58.13; H, 8.13; N, 11.30; Cl, 9.53. Found: C, 58.43; H, 8.35; N, 11.33; Cl, 9.70.

EXAMPLE 73

4-Amino-5-chloro-N-[2-(diethylamino)ethyl]-2-(3-hydroxybut-1-yl)oxybenzamide

A stirred solution of 4-amino-5-chloro-N-[2-(diethylamino)ethyl]-2-hydroxybenzamide (2.86 g, 10 mmoles; prepared according to Preparation B), triphenylphosphine (2.62 g, 10 mmoles), (±) 1,3 butandiol (0.90 g, 10 mmoles) in dry tetrahydrofuran (50 ml) was treated dropwise with diethyl azodicarboxylate (1.75 g of 95% purity material, 10 mmoles). The solution was left to stir overnight. After evaporation of the solvent the residue was taken up in methylene chloride. The solution was washed with 0.4N NaOH, water, dried and the solvent evaporated. The residue was chromatographed over deactivated silica using methylene chloride (100), methanol (3), ammonium hydroxide (0.5) solvent system. The appropriate fractions were combined and the solvent evaporated. The residue was crystallized from methylene chloride-pentane to yield 1.05 g (29%) of the title compound. m.p. 136.5°–137.5° C. An additional amount of 0.56 g of material was obtained from the mother liquor after crystallization from toluene, followed by recrystallization from methylene chloride-pentate, and from a dilute solution of ethyl acetate, m.p. 135°–137° C.

Anal. Calc'd. for $C_{17}H_{28}ClN_3O_3$: C, 57.05; H, 7.89; N, 11.74; Cl, 9.91. Found: C, 56.90; H, 8.12; N, 11.62; Cl, 9.99.

EXAMPLE 74

A.

4-Amino-N-(1-azabicyclo[2.2.2.]oct-3-yl)-5-chloro-2-hydroxybenzamide

A suspension of sodium hydride (0.25 g of a 60% oil emulsion, washed with pentane) in DMF (10 mL) was cooled to 0° C. and a solution of ethanethiol (0.376 g) in DMF (10 mL) was slowly added. After the evolution of hydrogen had subsided, 4-amino-N-(1-azabicyclo[2.2.2]oct-3-yl)-5-chloro-2-methoxybenzamide[1] (1.3 g) was added and the solution was heated to 95° C. for 1 hour. The reaction mixture was concentrated in vacuo and the residue dissolved in water (25 mL). This aqueous solution was washed with methylene chloride, and then saturated with carbon dioxide. The product was isolated by filtration to yield 1.21 g (98%), m.p. 311°–314° C.

Lit. ref. 1. European Patent Application No. 99,789, Delalande S. A., Feb. 1, 1984.

B.

4-Amino-N-(1-azabicyclo[2.2.2]oct-3-yl)-5-chloro-2-hydroxybenzamide hydrochloride dihydrate To an aqueous solution of the free base of the title compound, obtained above was added an equimolar amount of 37% (conc.) hydrochloric acid. The solution was concentrated in vacuo and chromatographed on silica gel eluting with methylene chloride, methanol and ammonium hydroxide in the ratio of 70:30:0.5 to afford the hydrochloride, dihydrate, m.p. >170° C. decomp.

Anal. Calc'd for $C_{14}H_{18}ClN_3O_2 \cdot 0.75HCl \cdot 2H_2O$: C, 46.82; H, 6.38; N, 11.70; Cl, 17.28. Found: C, 46.58; H, 6.03; N, 11.96; Cl, 16.37.

EXAMPLE 75

4-Amino-N-(1-azabicyclo[2.2.2]oct-3-yl)-5-chloro-2-(2-propanon-1-yl)oxybenzamide When the starting benzamide intermediate from Example 74 is first reacted with one equivalent of sodium hydride in DMF and then to this is added on equivalent of chloroacetone and the mixture stirred for 5 h followed by heating to 50° C. for 30 min and workup, the title compound is isolated.

EXAMPLE 76

4-Amino-N-(1-azabicyclo[2.2.2.]oct-3-yl)-2-(butan-2-on-3-yl)oxy-5-chlorobenzamide To a stirred solution of 4-amino-N-(1-azabicyclo[2.2.2]oct-3-yl)-5-chloro-2-hydroxybenzamide (400 mg) in 8 mL DMF was added anhydrous potassium carbonate (700 mg), sodium iodide (10 mg) and 3-chloro-2-butanone (235 mg). The mixture was heated at 45°–46° C. for 2 hours. The solvent was removed in vacuo and the product was dissolved in dichloromethane and chromatographed on silica gel eluting with dichloromethane, methanol, ammonium hydroxide in the ratio of 94:6:1. Appropriate fractions were combined and concentrated in vacuo to give 327 mg of the title compound as a light beige solid, m.p. >200° C.

In another preparation, the product was isolated as a 1.25 malate monohydrate by crystallization from methanol-acetone-acetonitrile, to give a white solid, m.p. 183°–4° C.

Anal. Calc'd for $C_{18}H_{24}ClN_2O_3 \cdot 1.25C_4H_4O_4 \cdot H_2O$: C, 52.22, H, 5.90, N, 7.94; Cl, 6.70. Found: C, 52.06; H, 5.54; N, 7.76; Cl, 6.63.

EXAMPLE 77

1-Allyloxy-4-amino-N-(1-azabicyclo[2.2.2]oct-3-yl)-5-chlorobenzamide

4-Amino-N-(1-azabicyclo[2.2.2]oct-3-yl)-5-chloro-2-hydroxybenzamide (444 mg) was added to a suspension of sodium hydride (66 mg of a 60% oil emulsion, washed with pentane) in DMF (10 mL). When the evolution of hydrogen ceased, the solution was treated with allyl bromide (195 mg) for 1 hour. The solution was diluted with ethyl acetate and the volume of solvent mixture consisting of acetonitrile, methanol and ammonium hydroxide in the ratio of 100:15:0.5, and flash chromatographed over silica gel eluting with the same solvent system. The appropriate fractions were combined and concentrated. The solid obtained was collected by filtration and dried under vacuum to yield 0.230 g (46%) of the title compound, m.p. 220° C.

Anal. Calc'd for $C_{17}H_{22}ClN_3O_2$: C, 60.80; H, 6.60; N, 12,57; Cl, 10.56. Found: C, 60.67; H, 6.65; N, 12,86; Cl, 10.09.

EXAMPLE 78

Amino-N-(1-azabicyclo[2.2.2]-oct-3-yl)-5-chloro-2-propargyloxybenzamide

A mixture of 4-amino-N-(1-azabicyclo[2.2.2]-oct-3-yl)-5-chloro-2-hydroxybenzamide (590 mg), potassium carbonate (2.8 g), propargyl bromide (9.3 g of an 80% solution of propargyl bromide in toluene) in DMF (10 mL) was stirred at room temperature for 1 hour. The solid was filtered off, and the filtrate diluted with ether. The resulting precipitate was collected and washed with ether. This solid was dissolved in a small amount of a mixture of acetonitrile, methanol and ammonium hydroxide in the ratio of 100:15:0.5, and flash chromatographed over silica gel eluting with the same solvent system. The appropriate fractions were combined and concentrated. The resulting solid was dried under vacuum to yield the title compound (0.115 g; 17%), m.p. >170°·C. decomp.

Anal. Calc'd for $C_{17}H_{20}Cl_3O_2 \cdot H_2O$: C, 58.17; H, 6.27; N, 11.97; Cl, 10.10; $H_2O$, 5.13. Found: C, 57.81; H, 6.16; N, 11.75; Cl, 9.77; $H_2O$, 4.67.

EXAMPLE 79

4-Amino-N-(1-azabicyclo[2.2.2]oct-3-yl)-5-chloro-2-(2-hydroxyethoxy)benzamide

The general procedure of Example 75 is repeated except that chloroacetone utilized therein is replaced by 2-chloro-ethanol to give the title compound.

EXAMPLE 80

4-Amino-N-(1-azabicyclo[2.2.2]-oct-3-yl)-5-chloro-2-(cyclohexanon-2-yl)oxybenzamide The general procedure of Example 75 is repeated except that chloroacetone utilized therein is replaced by 2-chlorocyclohexanone to give the title compound.

EXAMPLE 81

4-Amino-N-(1-azabicyclo[2.2.2]oct-3-yl)-5-chloro-2-[2-(methylsulfinyl)ethoxy]benzamide A. 4-Amino-N-(1-azabicyclo[2.2.2]-oct-3-yl)-5-chloro-2-[2-hydroxy]benzamide (590 mg) was added to a stirred suspension of sodium hydride (88 mg of a 60% oil emulsion, washed with pentane). After the evolution of hydrogen ceased, 2-chloroethyl methyl sulfide (221 mg) and potassium iodide (133 mg) was added and the reaction mixture was heated to 70° C. for 2.5 hours. The solvent was then evaporated and the residue chromatographed on deactivated silica gel eluting with acetonitrile, methanol, ammonium hydroxide in the ratio of 100:10:0.5. Chromatography yielded 210 mg (28%) of 4-amino-N-(1-azabicyclo[2.2.2]-oct-3-yl)-5-chloro-2-[2-(methylthio)ethoxy]benzamide B. The product described in A (576 mg,) was dissolved in aqueous methanol (26 mL) and treated with hydrochloric acid (3.6 mL of a 2N solution) and then sodium metaperiodate (331 mg) for 2 hours. The mixture was then concentrated at 5 mm pressure and ambient temperature, and the residue basified (cold, 4N sodium hydroxide), extracted ($CH_2Cl_2$), dried, and concentrated. The resulting residue was chromatographed on deactivated silica gel eluting with acetonitrile, methanol, and ammonium hydroxide in the ratio of 100:10:0.5 to yield the title compound as a foam (282 mg, 47%).

Anal. Calc'd for $C_{17}H_{24}ClN_2O_3S$: C, 52.91; H, 6.27; N, 10.89; Cl, 9.19; S, 8.31. Found: (corrected for 2.27% of $H_2O$): C, 51.18; H, 6.32; N, 10.70; Cl, 9.54; S, 7.90.

EXAMPLE 82

4-Amino-N-(1-azabicyclo[2.2.2]-oct-3-yl)-5-chloro-2-(2-hydroxypropan-1-yl)oxybenzamide The product from Example 75 is treated with sodum borohydride in absolute ethanol at reflux to give the title compound.

EXAMPLE 83

4-Amino-N-(1-azabicyclo[2.2.2]-oct-3-yl)-5-chloro-2-(2-hydroxy-but-3-yl)benzamide (mixture of threo and erythro isomers)

The product from Example 76 is treated with sodium borohydride in absolute ethanol at reflux to give the title product.

EXAMPLE 84

N-(1-Azabicyclo[2.2.2]-oct-3-yl)-5-chloro-4-methylamino-2-hydroxybenzamide

A slurry of sodium hydride (0.2 g of a 50% oil emulsion) in DMF (30 mL) was cooled to 0° C. and treated with ethane thiol (0.42 g). After the evolution of hydrogen had stopped N-(1-azabicyclo[2.2.2]-oct-3-yl-5-chloro-4-methylamino-2-methoxybenzamide[2] was added in 150 mL DMF and heated to 100° C. overnight. The reaction mixture was then concentrated, dissolved in water and treated with carbon dioxide. The title compound was collected by filtration to yield 0.12 g of a beige solid, m.p. >275° C. decomp.

Lit. ref. 2. European Patent Application No. 158,532, A. H. Robins Company Inc., Oct. 16, 1985.

Anal. Calc'd for $C_{15}H_{20}ClN_3O_2$: C, 58.16; H, 6.51; N, 13.56; Cl, 11.44. Found: C, 59.25; H, 7.04; N, 12.34; Cl, 11.23.

Improved experimental procedures for preparing the compounds described hereinabove as Examples 20 and 21 are given below.

EXAMPLE 85

Improved procedure for the preparation of 4-amino-5-chloro-2-[2-(methylthio)ethoxy]-N-[2-(diethylamino)ethyl]benzamide (Example 20)

A suspension of 4-amino-5-chloro-N-[(2-(diethylamino)ethyl]-2-hydroxybenzamide tetrabutylammonium salt (158.2 g, 0.30 mole) (Preparation No. 3) in 320 ml of acetonitrile was warmed to obtain solution and treated with 2-chloroethylmethylsulfide (37.64 g, 0.33 mole) and sodium bromide (1.0 g). The reaction solution was then stirred at reflux for 10 hr and stored at 0° C. for 44 hrs. The mixture was filtered to give the title compound as a light brown solid (20.5 g; mp 119°–122° C.) and the filtrate was evaporated to a brown oil. The residue was crystallized by stirring with a ca. 900 ml of water and, after filtration, was recrystallized from acetonitrile to give a second lot of brown solid. Total yield: 67.4 g (62.4%); mp 119°–122° C.).

EXAMPLE 86

A. Improved procedure for the preparation of 4-amino-5-chloro-2-[2-(methyl-sulfinyl)ethoxy]-N-[2-(diethylamino)ethyl]benzamide (Example 21)

4-Amino-5-chloro-2-[2-(methylthio)ethoxy]-N-[2-(diethylamino)ethyl]benzamide (33.11 g, 92 mmoles) was dissolved in 90 ml of glacial acetic acid, chilled to 10° C. and treated all at once with 107.3 ml of 30% hydrogen peroxide (96.6 mmoles). The solution was stirred at 10° C. for 10 min and at ambient temperature for one hour.

Most of the acetic acid was removed at reduced pressure and the oily residue was partitioned between 150 ml $CH_2Cl_2$ and 150 ml of water. The mixture was made strongly basic with 40% NaOH and the organic layer was separated. The basic solution was extracted once more with 75 ml of $CH_2Cl_2$ and the combined extracts were dried and evaporated. The residual oil that readily solidified was recrystallized from ethyl acetate to yield 28.9 g (84%) of the title compound as a white solid; mp 115°–116.5° C.

B.
4-amino-5-chloro-2-[2-(methylsulfinyl)ethoxy]-N-[2-(diethylamino)ethyl]benzamide hydrochloride monohydrate A mixture of 4-amino-5-chloro-2[2-(methylsulfinyl)ethoxy]-N-[2-(diethylamino)ethyl]benzamide (84.50 g, 22.5 mmoles), acetone (592 ml) and 2-propanol (169 ml) was stirred and warmed until complete solution (ca. 25° C.) and then 56.2 ml of 4N HCl (1 equivalent) was all at once. The temperature rose to 32° C. After one hour at ambient temperature the mixture was stored at 0° C. for 18 hours. The hydrochloride salt was collected by filtration, rinses with acetone and dried in vacuo over $P_2O_5$ for six hours. Yield: 89.6 g (96.6%); mp 117°–124° C.

Anal. Calc'd for $C_{16}H_{26}ClN_3O_3S \cdot HCl \cdot H_2O$: C, 44.65; H, 6.79; N, 9.76; Cl, 16.48; S, 7.45; $KF(H_2O)$, 4.18. Found: C, 44.86; H, 7.00; N, 9.77; Cl, 16.58; S, 7.45; $KF(H_2O)$, 4.50.

We claim:
1. A compound of the formula

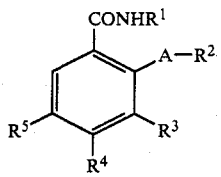

XXI wherein
$R^3$ is hydrogen or, when $R^4$ and $R^5$ are each hydrogen, $R^3$ may be (lower)alkoxy;
$R^4$ is hydrogen, amino, lowerallylamino, acetamido or (lower)alkoxy;
$R^5$ is hydrogen, chloro, bromo, fluoro, trifluoromethyl, (lower)alkylthio, (lower)alkanesulfinyl, (lower)alkanesulfonyl, sulfamyl or

, or $R^4$ and $R^5$, taken together, may be —HN—N=N—;
$R^6$ is (lower)alkyl, (lower)alkenyl or (lower)alkynyl;
$R^1$ is

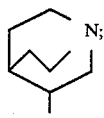

wherein
A is oxygen or

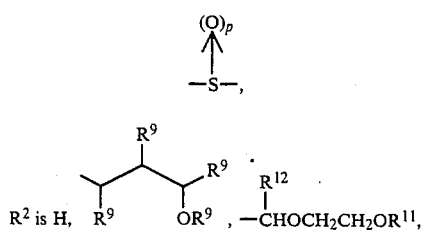

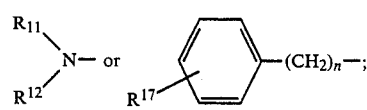

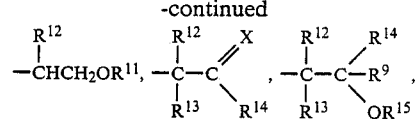

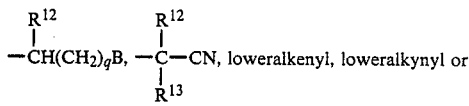

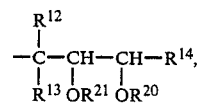

wherein
X is oxygen, sulfur or =$NOR^{16}$;
Z is —$(CH_2)_p$—, O, N or

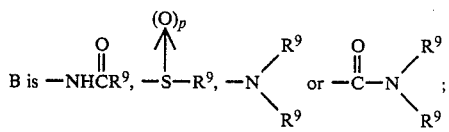

p is 0, 1 or 2;
q is an integer of from 0 to 4, inclusive;
$R^9$ is hydrogen or (lower)alkyl;
$R^{11}$, $R^{12}$, $R^{13}$, $R^{15}$, and $R^{16}$ are the same or different, and are hydrogen, (lower)alkyl, (lower)alkenyl, (lower)alkynyl, (lower)alkoxy(lower)alkyl, cycloalkyl containing from 5 to 7 carbon atoms, inclusive, or

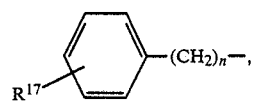

wherein
$R^{17}$ is hydrogen, halogen, hydroxy, (lower)alkyl or (lower)alkoxy; provided that, when $R^{11}$, $R^{15}$ or $R^{16}$ is (lower)alkenyl or (lower)alkynyl, the unsaturated carbon atom may not be directly attached to an oxygen or nitrogen atom;
$R^{15}$ can additionally be loweralkylcarbonyl;
$R^{14}$ is hydrogen, halogen, (lower)alkyl, (lower)alkenyl, (lower)alkynyl, cycloalkyl containing from 5 to 7 carbon atoms, inclusive, hydroxy, (lower)alkoxy, (lower)alkenyloxy, (lower)alkoxycarbonyl(lower)alkenyl, hydrazino, acetylhydrazino, thienyl, phenyl,

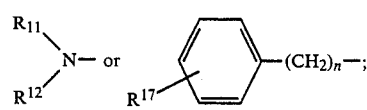

$R^{20}$ and $R^{21}$ are each hydrogen or $R^{12}$ and $R^{13}$, taken together with the carbon atom to which they are attached, may form a saturated ring of from 5 to 7 atoms, inclusive;

or R¹² and R¹⁴, taken together with the carbon atoms to which they are attached, may form a saturated or unsaturated ring of from 5 to 7 atoms, inclusive; or a nontoxic pharmaceutically acceptable salt, hydrate, solvate or quaternary ammonium salt thereof.

2. A compound of claim 1 having the formula

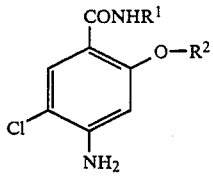   XXI wherein
R¹ is

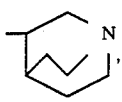

and wherein
R² is H,

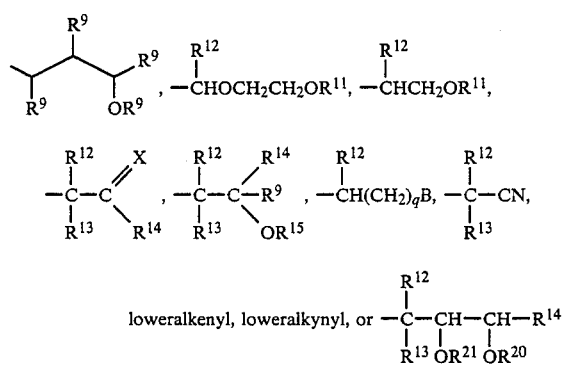

wherein
X is oxygen, sulfur or =NOR¹⁶;
Z is —(CH₂)$_p$—, O, N or

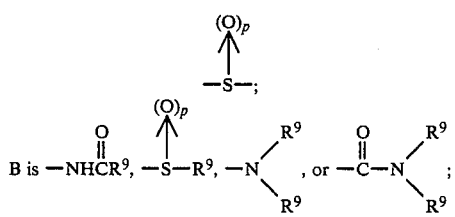

p is 0, 1 or 2;
q is an integer of from 0 to 4;
R⁹ is hydrogen or (lower)alkyl;
R¹¹, R¹², R¹³, R¹⁵ and R¹⁶ are the same or different, and are hydrogen, (lower)alkyl, (lower)alkenyl, (lower)alkynyl, (lower)alkoxy(lower)alkyl or cycloalkyl containing from 5 to 7 carbon atoms, inclusive, provided that, when R¹¹, R¹⁵ or R¹⁶ is (lower)alkenyl or (lower)alkynyl, the unsaturated carbon atom may not be directly attached to an oxygen or nitrogen atom;

R¹⁵ can additionally be loweralkylcarbonyl;
R¹⁴ is hydrogen, halogen, (lower)alkyl, (lower)alkenyl, (lower)alkynyl, cycloalkyl containing from 5 to 7 carbon atoms, inclusive, (lower)alkoxy, hydroxy, (lower)alkenyloxy, hydrazino, (lower)alkoxycarbonyl(lower)alkenyl, acetylhydrazino, thienyl, phenyl or

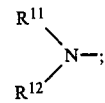

R²⁰ and R²¹ are each hydrogen
or R¹² and R¹⁴, taken together with the carbon atoms to which they are attached, may form a saturated or unsaturated ring of from 5 to 7 atoms, inclusive; or a nontoxic pharmaceutically acceptable salt, hydrate, solvate or quaternary ammonium salt thereof.

3. The compound of claim 1 wherein R² is loweralkenyl or loweralkynyl.

4. The compound of claim 1 wherein R² is butan-2-on-3-yl.

5. The compound of claim 1 which is 4-Amino-N-(1-azabicyclo[2.2.2]oct-3-yl)-5-chloro-2-hydroxybenzamide.

6. The compound of claim 1 which is 4-Amino-N-(1-azabicyclo[2.2.2.]oct-3-yl)-2-(butan-2-on-3-yl)oxy-5-chlorobenzamide.

7. The compound of claim 1 which is 2-Allyloxy-4-amino-N-(1-azabicyclo[2.2.2]oct-3-yl)-5-chlorobenzamide.

8. The compound of claim 1 which is 4-Amino-N-(1-azabicyclo[2.2.2]oct-3-yl)-5-chloro-2-propargyloxybenzamide 9. The compound of claim 1 which is 4-Amino-N-(1-azabicyclo[2.2.2]oct-3-yl)-5-chloro-2-[2-(methylsulfinyl)ethoxy]benzamide.

10. The compound of claim 1 which is N-1-Azabicyclo[2.2.2]oct-3-yl)-5-chloro-4-methylamino-2-hydroxybenzamide.

11. A pharmaceutical composition for the alleviation of nausea and vomiting, which commprises an effective antiemitic amount of at least one compound of Formula XXI of claim 1, or a salt, hydrate or solvate thereof, plus a pharmaceutically acceptable carrier.

12. A pharmaceutical composition for the treatment of disorders related to impaired gastric motility, which comprises an effective gastric motility facilitating amount of at least one compound of Formula XXI of claim 1, or a salt, hydrate or solvate thereof, and a pharmaceutically acceptable carrier.

13. A method of alleviating nausea and vomiting in a warm-blooded mammal in need thereof, which comprises administering to said mammal an effective antiemetic amount of at least one compound of Formula XXI of claim 1, or a salt, hydrate or solvate thereof, in a pharmaceutically acceptable carrier.

14. A method of treating disorders related to impaired gastric motility in a warm-blooded mammal, which comprises administering to said mammal an effective gastric motility facilitating amount of at least one compound of Formula XXI of claim 1, or a salt, hydrate or solvate thereof, in a pharmaceutically acceptable carrier.

* * * * *